United States Patent
Iwata et al.

(10) Patent No.: US 9,901,571 B2
(45) Date of Patent: Feb. 27, 2018

(54) TETRAHYDROPYRAZOLOPYRIDINE DERIVATIVES AS GHRELIN RECEPTOR AGONISTS

(71) Applicant: RaQualia Pharma Inc., Aichi (JP)

(72) Inventors: Yasuhiro Iwata, Aichi (JP); Kiyoshi Kawamura, Aichi (JP); Masaki Sudo, Aichi (JP); Kaoru Shimada, Aichi (JP); Shinichi Koizumi, Aichi (JP); Nobuyuki Takahashi, Aichi (JP); Keiko Obata, Aichi (JP); Makiko Kuroda, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 0 days.

(21) Appl. No.: 15/520,491

(22) PCT Filed: Nov. 2, 2015

(86) PCT No.: PCT/JP2015/005496
§ 371 (c)(1),
(2) Date: Apr. 20, 2017

(87) PCT Pub. No.: WO2016/067638
PCT Pub. Date: May 6, 2016

(65) Prior Publication Data
US 2017/0304277 A1 Oct. 26, 2017

Related U.S. Application Data

(60) Provisional application No. 62/073,836, filed on Oct. 31, 2014.

(51) Int. Cl.
*C07D 401/14* (2006.01)
*A61K 31/437* (2006.01)
*A61K 31/444* (2006.01)
*A61K 45/06* (2006.01)
*C07D 471/04* (2006.01)

(52) U.S. Cl.
CPC .......... *A61K 31/437* (2013.01); *A61K 31/444* (2013.01); *A61K 45/06* (2013.01); *C07D 471/04* (2013.01); *A61K 2300/00* (2013.01)

(58) Field of Classification Search
CPC .......................... C07D 401/14; A61K 31/437
USPC .......................................... 546/119; 514/303
See application file for complete search history.

(56) References Cited

U.S. PATENT DOCUMENTS

| | | | |
|---|---|---|---|
| 6,107,306 A | 8/2000 | Carpino et al. | |
| 6,110,932 A | 8/2000 | Carpino et al. | |
| 6,124,264 A | 9/2000 | Carpino et al. | |
| 2003/0100561 A1 | 5/2003 | Carpino et al. | |
| 2012/0302540 A1 | 11/2012 | Ambarkhane et al. | |
| 2012/0322821 A1 | 12/2012 | Shimada et al. | |
| 2015/0099709 A1 | 4/2015 | Takahashi et al. | |

FOREIGN PATENT DOCUMENTS

| | | |
|---|---|---|
| WO | 97/24369 | 7/1997 |
| WO | 98/58949 | 12/1998 |
| WO | 2012/164473 | 12/2012 |
| WO | 2013/175805 | 11/2013 |

OTHER PUBLICATIONS

International Search Report dated Jan. 26, 2016 in International Application No. PCT/JP2015/005496.
Written Opinion of the International Searching Authority dated Jan. 26, 2016 in International Application No. PCT/JP2015/005496.
Pedretti, A., "Modeling of human ghrelin receptor (hGHS-R1a) in its close state and validation by molecular docking", Bioorganic & Medicinal Chemistry, 2007, vol. 15, No. 8, pp. 3054-3064.
Christine Delporte, "Structure and Physiological Actions of Ghrelin", Scientifica 2013, Article ID 518909 (http://dx.doi.org/10.1155/2013/518909), 25 pages, 2013.
Jose M. Garcia et al., "Effect on Body Weight and Safety of RC-1291, a Novel Orally Available Ghrelin Mimetic and Growth Hormone Secretagogue: Results of a Phase I, Randomized, Placebo-Controlled, Multiple-Dose Study in Healthy Volunteers", The Oncologist 12, 594-600, 2007.
R. Northrup et al., "Effect of ghrelin and anamorelin (ONO-7643), a selective ghrelin receptor agonist, on tumor growth in a lung cancer mouse xenograft model", Support Care Cancer 21, 2409-2415, 2013.
G. J. Sanger et al., "Development of drugs for gastrointestinal motor disorders: translating science to clinical need", Neurogastroenterol Motil 20, 177-184, 2008.

(Continued)

*Primary Examiner* — Niloofar Rahmani
(74) *Attorney, Agent, or Firm* — Wenderoth, Lind & Ponack, L.L.P.

(57) ABSTRACT

The present invention relates to novel compounds of a formula (I) or a pharmaceutically acceptable salt or solvate thereof, processes for their preparation, pharmaceutical compositions comprising them and their use in therapy, for example as modulators of the growth hormone secretagogue receptor (also referred to as the ghrelin receptor or GHSR-1a receptor) and/or for the treatment and/or prophylaxis of a disorder mediated by the ghrelin receptor.

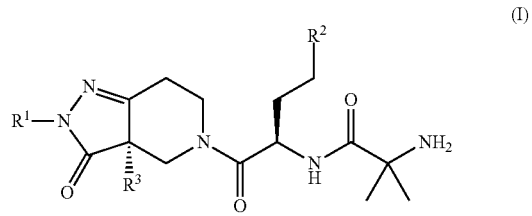

(I)

11 Claims, No Drawings

(56) References Cited

OTHER PUBLICATIONS

Jose M. Garcia et al., "Ghrelin Prevents Cisplatin-Induced Mechanical Hyperalgesia and Cachexia", Endocrinology 149, 455-460, 2008.

Keisuke Miki et al., "Effects of Ghrelin Treatment on Exercise Capacity in Underweight COPD Patients: a substudy of a multicenter, randomized, double-blind, placebo-controlled trial of ghrelin treatment", BMC Pulmonary Medicine 13, 37-46, 2013.

Nobuhiro Matsumoto et al., "Clinical Application of Ghrelin for Chronic Respiratory Diseases", Methods in Enzymology 514, 399-407, 2012.

Markus S. Anker et al., "Highlights of mechanistic and therapeutic cachexia and sarcopenia research 2010 to 2012 and their relevance for cardiology", Arch Med Sci 9, 166-171, 2013.

Mathieu Mequinion et al., "Ghrelin: central and peripheral implications in anorexia nervosa", Frontiers in Endocrinology 4, 1-27, 2013.

Ralf Nass, M.D., et al., "Effects on an Oral Ghrelin Mimetic on Body Composition and Clinical Outcomes in Healthy Older Adults: A Randomized, Controlled Trial", Ann intern Med 149, 601-611, 2008.

Shuji Takiguchi et al., "Clinical application of ghrelin administration for gastric cancer patients undergoing gastrectomy", Gastric Cancer 17, 200-205, 2014.

Konstantinos Karmiris et al., "Leptin, adiponectin, resistin, and ghrelin—Implications for inflammatory bowel disease", Mol. Nutr Food Res 52, 855-866, 2008.

N. Ejskjaer et al., "A phase 2a, randomized, double-blind 28-day study of TZP-102 a ghrelin receptor agonist for diabetic gastroparesis", Neurogastroenterol Motil 25, e140-e150, 2013.

Ichiro Kishimoto et al., "Ghrelin and cardiovascular diseases", Journal of Cardiology 59, 8-13, 2012.

Geetali Pradhan et al., "Ghrelin: much more than a hunger hormone", Curr Opin Clin Nutr Metab Care 16, 619-624, 2013.

Daryl O. Schwenke et al., "One Dose of Ghrelin Prevents the Acute and Sustained Increase in Cardiac Sympathetic Tone after Myocardial Infarction", Endocrinology 153, 2436-2443, 2012.

Itaru Kyoraku et al., "Ghrelin reverses experimental diabetic neuropathy in mice", Biochemical and Biophysical Research Communications 389, 405-408, 2009.

Elli Marakai et al., "The Role of Ghrelin, Neuropeptide Y and Leptin Peptides in Weight Gain after Deep Brain Stimulation for Parkinson's Disease", Stereotact Funct Neurosurg 90, 104-112, 2012.

Elham Eftekhari et al., "The relation between peptide hormones and sex hormone in patients with multiple sclerosis", Ir J neurol 12, 60-65, 2013.

Michael Ankersen et al., "Growth hormone secretagogues: recent advances and applications", Drug Discovery Today 4, 497-506, 1999.

A.D. Shafton et al., "Oral administration of a centrally acting ghrelin receptor agonist to conscious rats triggers defecation", Neurogastroenterol Motil 21, 71-77, 2009.

Pierre Poitras et al., "Gastrokinetic effect of ghrelin analog RC-1139 in the rat Effect on post-operative and on morphine induced ileus", Peptides 26, 1598-1601, 2005.

TETRAHYDROPYRAZOLOPYRIDINE DERIVATIVES AS GHRELIN RECEPTOR AGONISTS

TECHNICAL FIELD

The present invention relates to novel tetrahydropyrazolopyridine derivatives, processes for their preparation, intermediates usable in these processes, and pharmaceutical compositions containing the compounds. The present invention also relates to the use of the tetrahydropyrazolopyridine derivatives in therapy, for example as modulators of the growth hormone secretagogue receptor, also referred to as the ghrelin receptor or GHSR-1a and/or for the treatment and/or prophylaxis of cancer anorexia/cachexia; cachexia and anorexia by anti-cancer drugs; hyperalgesia by anti-cancer drugs; COPD (chronic obstructive pulmonary disease)/COPD cachexia; sarcopenia; eating disorders and neurological eating disorders; weight loss suppression; early postoperative recovery of cancer patients; chronic respiratory tract infection; inflammation; IBD (inflammatory bowel disease); FD (functional dyspepsia); constipation; diabetic gastroparesis and gastroparesis; heart failure; myocardial infarction; diabetic neuropathy; Parkinson's disease; multiple sclerosis; diagnosis and treatment of growth hormone deficiency; elderly QOL (quality of life) improvement; bowel movement disturbance of spinal cord injury patients; post-operative ileus; and morphine induced ileus.

BACKGROUND ART

Ghrelin is the endogenous ligand for the growth hormone (GH) secretagogue receptor. It was originally purified from stomach and is a 28 amino acid peptide hormone in which the serine at position 3 is n-octanoylated. It has potent GH releasing activity and thus is believed to play an important role in maintaining GH release and energy homeostasis (Non-patent literature, NPL 1). In particular, it appears to exert potent appetite-stimulating activities. Then it has been known that a ghrelin agonist is useful for the treatment and/or prophylaxis of cancer anorexia/cachexia (NPL 2, 3 and 4); cachexia and anorexia by anti-cancer drugs (NPL 4 and 5); hyperalgesia by anti-cancer drugs (NPL 5); COPD/COPD cachexia (NPL 6 and 7); sarcopenia (NPL 8); eating disorders and neurological eating disorders (NPL 9); weight loss suppression (NPL 10); early postoperative recovery of cancer patients (NPL 11); chronic respiratory tract infection (NPL 7); inflammation (NPL 12); IBD (NPL 12); FD (NPL 4); constipation (NPL 9); diabetic gastroparesis and gastroparesis (NPL 4 and 13); heart failure (NPL 14, 15 and 16); myocardial infarction (NPL 14, 15 and 16); diabetic neuropathy (NPL 17); Parkinson's disease (NPL 18); multiple sclerosis (NPL 19); diagnosis and treatment of growth hormone deficiency (NPL 20); elderly QOL improvement (NPL 20); bowel movement disturbance of spinal cord injury patients (NPL 21); postoperative ileus (NPL 4 and 22); and morphine induced ileus (NPL 22).

CITATION LIST

Non Patent Literature

{NPL 1} Scientifica 2013, Article ID 518909 (http://dx.doi.org/10.1155/2013/518909), 25 pages, 2013
{NPL 2} The Oncologist 12, 594-600, 2007
{NPL 3} Support Care Cancer 21, 2409-2415, 2013
{NPL 4} Neurogastroenterol Motil 20, 177-184, 2008
{NPL 5} Endocrinology 149, 455-460, 2008
{NPL 6} BMC Pulmonary Medicine 13, 37-46, 2013
{NPL 7} Methods in Enzymology 514, 399-407, 2012
{NPL 8} Arch Med Sci 9, 166-171, 2013
{NPL 9} Frontiers in Endocrinology 4, 1-27, 2013
{NPL 10} Ann intern Med 149, 601-611, 2008
{NPL 11} Gastric Cancer 17, 200-205, 2014
{NPL 12} Mol Nutr Food Res 52, 855-866, 2008
{NPL 13} Neurogastroenterol Motil 25, e140-e150, 2013
{NPL 14} Journal of Cardiology 59, 8-13, 2012
{NPL 15} Curr Opin Clin Nutr Metab Care 16, 619-624, 2013
{NPL 16} Endocrinology 153, 2436-2443, 2012
{NPL 17} Biochemical and Biophysical Research Communications 389, 405-408, 2009
{NPL 18} Stereotact Funct Neurosurg 90, 104-112, 2012
{NPL 19} Ir J neurol 12, 60-65, 2013
{NPL 20} Drug Discovery Today 4, 497-506, 1999
{NPL 21} Neurogastroenterol Motil 21, 71-77, 2009
{NPL 22} Peptides 26, 1598-1601, 2005

SUMMARY OF INVENTION

Technical Problem

It is therefore desirable to find new compounds which modulate ghrelin receptor activity.

Solution to Problem

[1] The present invention provides a compound of the following formula (I):

[Chem. 1]

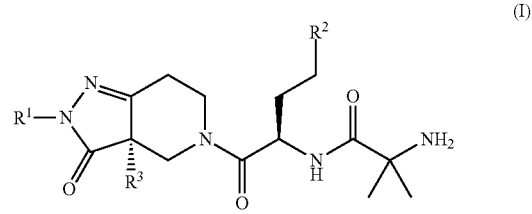

Wherein:
$R^1$ is $C_{1-6}$ alkyl, where the alkyl is unsubstituted or substituted with one to three substituents independently selected from halogen; more preferably $R^1$ is methyl or trifluoroethyl;
$R^2$ is selected from the group consisting of (1) phenyl, (2) $CH_2$-phenyl($CH_2OH$), and (3) $CH_2$-pyridyl; where the benzene ring or the pyridine ring is unsubstituted or substituted with one to two substituents independently selected from (1) halogen, (2) $C_{1-6}$ alkyl, which may have substituents selected from halogen, and hydroxyl, and (3) $C_{1-6}$ alkylsulfonyl; preferably, (1) halogen, (2) methyl, (3) difluoromethyl, (4) trifluoromethyl, (5) hydroxymethyl, and (6) methanesulfonyl;
when $R^2$ is (1) phenyl, a compound where the benzene ring is unsubstituted or substituted with one to two substituents independently selected from halogen and hydroxymethyl is more preferable; when $R^2$ is (2) $CH_2$-phenyl($CH_2OH$), a compound where the benzene ring is unsubstituted is more preferable; when $R^2$ is (3) $CH_2$-pyridyl, a compound where the pyridine ring is unsubstituted or substituted with one to two substituents independently selected from difluoromethyl and trifluoromethyl is more preferable;

R³ is (1) benzyl or (2) CH₂-(2-pyridyl), where the benzene ring or the pyridine ring is unsubstituted or substituted with one to two substituents independently selected from (1) halogen and (2) C$_{1-6}$ alkyl, which may have substituents selected from halogen, hydroxyl, and C$_{1-6}$ alkylsulfonyl; a compound where the benzene ring or the pyridine ring is unsubstituted is more preferable;

or a pharmaceutically acceptable salt thereof.

[2] This invention provides a compound represented by the above formula (I) according to [1],
wherein:
R¹ is methyl or trifluoroethyl;
or a pharmaceutically acceptable salt thereof.

[3] This invention provides a compound according to [1] or [2] wherein HLM CLint of the compound is lower than 65 mL/min/kg
or a pharmaceutically acceptable salt thereof.

[4] Suitable individual compounds of the present invention are:

2-amino-N—((R)-1-((R)-3a-benzyl-2-methyl-3-oxo-3a,4,6,7-tetrahydro-2H-pyrazolo[4,3-c]pyridin-5(3H)-yl)-4-(2-(methylsulfonyl)phenyl)-1-oxobutan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-4-phenylbutan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-4-(2-chloro-4-(hydroxymethyl)phenyl)-1-oxobutan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-4-(2-fluoro-4-(hydroxymethyl)phenyl)-1-oxobutan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-4-(2-fluoro-5-(hydroxymethyl)phenyl)-1-oxobutan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-4-(2-(hydroxymethyl)phenyl)-1-oxobutan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-5-(3-(hydroxymethyl)phenyl)-1-oxopentan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-5-(2-(hydroxymethyl)phenyl)-1-oxopentan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-5-(pyridin-2-yl)pentan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-5-(6-(trifluoromethyl)pyridin-2-yl)pentan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-5-(5-fluoropyridin-2-yl)-1-oxopentan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-5-(6-methylpyridin-2-yl)-1-oxopentan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-5-(6-(difluoromethyl)pyridin-2-yl)-1-oxopentan-2-yl)-2-methylpropanamide;

2-amino-2-methyl-N—((R)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)-4-phenylbutan-2-yl) propanamide;

2-amino-2-methyl-N—((R)-4-(2-(methylsulfonyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)propanamide;

2-amino-N—((R)-4-(4-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide;

2-amino-N—((R)-4-(4-(fluoromethyl)-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide;

2-amino-N—((R)-4-(3-fluoro-4-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide; and 2-amino-N—((R)-4-(5-fluoro-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide;

or a pharmaceutically acceptable salt thereof.

[5] More suitable individual compounds of the present invention are:

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-4-phenylbutan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-4-(2-chloro-4-(hydroxymethyl)phenyl)-1-oxobutan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-4-(2-fluoro-4-(hydroxymethyl)phenyl)-1-oxobutan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-4-(2-fluoro-5-(hydroxymethyl)phenyl)-1-oxobutan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-5-(3-(hydroxymethyl)phenyl)-1-oxopentan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-5-(2-(hydroxymethyl)phenyl)-1-oxopentan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-5-(pyridin-2-yl)pentan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-5-(6-(trifluoromethyl)pyridin-2-yl)pentan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-5-(6-(difluoromethyl)pyridin-2-yl)-1-oxopentan-2-yl)-2-methylpropanamide;

2-amino-2-methyl-N—((R)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)-4-phenylbutan-2-yl) propanamide; and 2-amino-N—((R)-4-(4-(fluoromethyl)-2-(hydroxymethyl) phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide;

or a pharmaceutically acceptable salt thereof.

[6] The present invention provides a pharmaceutical composition comprising a compound or a pharmaceutically acceptable salt thereof, as described in any one of [1] to [5], and a pharmaceutically acceptable carrier.

[7] The present invention provides the pharmaceutical composition as described in [6], further comprising another pharmacologically active agent.

[8] The present invention provides a method of treatment of an animal including human suffering from a condition or disorder mediated by the ghrelin receptor, which comprises administering to said subject an effective amount of a compound of formula (I) or a pharmaceutically acceptable salt according to any one of [1] to [5].

[9] The present invention provides the method as described in [8], wherein the said condition or disorder is selected from the group consisting of: cancer anorexia/cachexia; cachexia and anorexia by anti-cancer drugs; hyperalgesia by anti-cancer drugs; COPD/COPD cachexia; sarcopenia; eating disorders and neurological eating disorders; weight loss suppression; early postoperative recovery of cancer patients; chronic respiratory tract infection; inflammation; IBD; FD; constipation; diabetic gastroparesis and gastroparesis; heart failure; myocardial infarction; diabetic neuropathy; Parkinson's disease; multiple sclerosis; diagnosis and treatment of growth hormone deficiency; elderly QOL improvement; bowel movement disturbance of spinal cord injury patients; postoperative ileus; and morphine induced ileus;

and combinations thereof.

[10] The present invention provides a use of a compound described in any one of [1] to [5] or a pharmaceutically acceptable salt, or composition thereof for the manufacture of a medicament for the treatment of a condition or disorder mediated by the ghrelin receptor.

[11] The present invention provides the use as described in [10], wherein the said condition or disorder is selected from the group consisting of: cancer anorexia/cachexia; cachexia and anorexia by anti-cancer drugs; hyperalgesia by anti-cancer drugs; COPD/COPD cachexia; sarcopenia; eating disorders and neurological eating disorders; weight loss suppression; early postoperative recovery of cancer patients; chronic respiratory tract infection; inflammation; IBD; FD; constipation; diabetic gastroparesis and gastroparesis; heart failure; myocardial infarction; diabetic neuropathy; Parkinson's disease; multiple sclerosis; diagnosis and treatment of growth hormone deficiency; elderly QOL improvement; bowel movement disturbance of spinal cord injury patients; postoperative ileus; and morphine induced ileus;

and combinations thereof.

[12] The present invention provides a compound described in any one of [1] to [5] a pharmaceutically acceptable salt for use in the treatment of a condition or disorder mediated by the ghrelin receptor.

[13] The present invention provides a process for preparing a pharmaceutical composition comprising mixing a compound described in any one of [1] to [5] or a pharmaceutically acceptable salt thereof with a pharmaceutically acceptable carrier, diluent or excipient.

[14] The present invention provides a compound of the formula (I):
wherein:
$R^1$ is $C_{1-6}$ alkyl, where the alkyl is unsubstituted or substituted with one to three substituents independently selected from halogen;
$R^2$ is selected from the group consisting of (1) phenyl, (2) $CH_2$-phenyl($CH_2OH$), and (3) $CH_2$-pyridyl; where the benzene ring or the pyridine ring is unsubstituted or substituted with one to two substituents independently selected from (1) halogen, (2) $C_{1-6}$ alkyl, which may have substituents selected from halogen, and hydroxyl, and (3) $C_{1-6}$ alkylsulfonyl; preferably (1) halogen, (2) methyl, (3) difluoromethyl, (4) trifluoromethyl, (5) hydroxymethyl, and (6) methanesulfonyl;
$R^3$ is (1) benzyl, or (2) $CH_2$-(2-pyridyl); where the benzene ring or the pyridine ring is unsubstituted or substituted with one to two substituents independently selected from (1) halogen and (2) $C_{1-6}$ alkyl, which may have substituents selected from halogen, hydroxyl, and $C_{1-6}$ alkylsulfonyl;
or a pharmaceutically acceptable salt thereof.

[15] The compound represented by the above formula (I) according to [14], wherein:
$R^1$ is methyl or trifluoroethyl;
or a pharmaceutically acceptable salt thereof.

[16] The compound represented by the above formula (I) according to [14] or [15],
wherein:
$R^1$ is methyl or trifluoroethyl;
$R^2$ is selected from the group consisting of (1) phenyl, (2) $CH_2$-phenyl($CH_2OH$), and (3) $CH_2$-pyridyl; where the benzene ring or the pyridine ring is unsubstituted or substituted with one to two substituents independently selected from (1) halogen, (2) methyl, (3) difluoromethyl, (4) trifluoromethyl, (5) hydroxymethyl, and (6) methanesulfonyl;
$R^3$ is (1) benzyl or (2) $CH_2$-(2-pyridyl), where the benzene ring or the pyridine ring is unsubstituted;
or a pharmaceutically acceptable salt thereof.

[17] The compound represented by the above formula (I) according to any one of [14] to [16],
wherein:
$R^1$ is methyl or trifluoroethyl;
when $R^2$ is (1) phenyl, a compound where the benzene ring is unsubstituted or substituted with one to two substituents independently selected from halogen and hydroxymethyl is more preferable; when $R^2$ is (2) $CH_2$-phenyl ($CH_2OH$), a compound where the benzene ring is unsubstituted is more preferable; when $R^2$ is (3) $CH_2$-pyridyl, a compound where the pyridine ring is unsubstituted or substituted with one to two substituents independently selected from difluoromethyl and trifluoromethyl is more preferable;
$R^3$ is (1) benzyl or (2) $CH_2$-(2-pyridyl) where the benzene ring or the pyridine ring is unsubstituted;
or a pharmaceutically acceptable salt thereof.

[18] The compound represented by the above formula (I) according to any one of [14] to [17],
wherein HLM CLint of the compound is lower than 65 mL/min/kg
or a pharmaceutically acceptable salt thereof.

[19] According to any one of [14] to [18], the compounds selected from the group consisting of:
2-amino-N—((R)-1-((R)-3a-benzyl-2-methyl-3-oxo-3a,4,6,7-tetrahydro-2H-pyrazolo[4,3-c]pyridin-5(3H)-yl)-4-(2-(methylsulfonyl)phenyl)-1-oxobutan-2-yl)-2-methylpropanamide;

2-amino-N—((R)-1-((R)-3a-benzyl-2-methyl-3-oxo-3a,4,6,
7-tetrahydro-2H-pyrazolo[4,3-c]pyridin-5(3H)-yl)-1-
oxo-4-phenylbutan-2-yl)-2-methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-4-(2-
chloro-4-(hydroxymethyl)phenyl)-1-oxobutan-2-yl)-2-
methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-4-(2-
fluoro-4-(hydroxymethyl)phenyl)-1-oxobutan-2-yl)-2-
methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-4-(2-
fluoro-5-(hydroxymethyl)phenyl)-1-oxobutan-2-yl)-2-
methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-4-(2-
(hydroxymethyl)phenyl)-1-oxobutan-2-yl)-2-methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-5-(3-
(hydroxymethyl)phenyl)-1-oxopentan-2-yl)-2-methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-5-(2-
(hydroxymethyl)phenyl)-1-oxopentan-2-yl)-2-methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-1-
oxo-5-(pyridin-2-yl)pentan-2-yl)-2-methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-1-
oxo-5-(6-(trifluoromethyl)pyridin-2-yl)pentan-2-yl)-2-
methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-5-(5-
fluoropyridin-2-yl)-1-oxopentan-2-yl)-2-methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-5-(6-
methylpyridin-2-yl)-1-oxopentan-2-yl)-2-methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-5-(6-
(difluoromethyl)pyridin-2-yl)-1-oxopentan-2-yl)-2-methylpropanamide;
2-amino-2-methyl-N—((R)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)-4-phenylbutan-2-yl) propanamide;
2-amino-2-methyl-N—((R)-4-(2-(methylsulfonyl)phenyl)-
1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)propanamide;
2-amino-N—((R)-4-(4-(hydroxymethyl)phenyl)-1-oxo-1-
((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide;
2-amino-N—((R)-4-(4-(fluoromethyl)-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide;
2-amino-N—((R)-4-(3-fluoro-4-(hydroxymethyl)phenyl)-1-
oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide; and 2-amino-N—((R)-4-(5-fluoro-2-(hydroxymethyl)phenyl)-1-
oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide;
or a pharmaceutically acceptable salt thereof.

[20] According to any one of [14] to [19], the compounds selected from the group consisting of:
2-amino-N—((R)-1-((R)-3a-benzyl-2-methyl-3-oxo-3a,4,6,
7-tetrahydro-2H-pyrazolo[4,3-c]pyridin-5(3H)-yl)-1-
oxo-4-phenylbutan-2-yl)-2-methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-4-(2-
chloro-4-(hydroxymethyl)phenyl)-1-oxobutan-2-yl)-2-
methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-4-(2-
fluoro-4-(hydroxymethyl)phenyl)-1-oxobutan-2-yl)-2-
methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-4-(2-
fluoro-5-(hydroxymethyl)phenyl)-1-oxobutan-2-yl)-2-
methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-5-(3-
(hydroxymethyl)phenyl)-1-oxopentan-2-yl)-2-methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-5-(2-
(hydroxymethyl)phenyl)-1-oxopentan-2-yl)-2-methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-1-
oxo-5-(pyridin-2-yl)pentan-2-yl)-2-methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-1-
oxo-5-(6-(trifluoromethyl)pyridin-2-yl)pentan-2-yl)-2-
methylpropanamide;
2-amino-N—((R)-1-((R)-3a-benzyl-2-methyl-3-oxo-3a,4,6,
7-tetrahydro-2H-pyrazolo[4,3-c]pyridin-5(3H)-yl)-5-(6-
(difluoromethyl)pyridin-2-yl)-1-oxopentan-2-yl)-2-methylpropanamide;
2-amino-2-methyl-N—((R)-1-oxo-1-((R)-3-oxo-3a-(pyridin-2-ylmethyl)-2-(2,2,2-trifluorotheyl)-3a,4,6,7-tetrahydro-2H-pyrazolo[4,3-c]pyridin-5(3H)-yl)-4-phenylbutan-2-yl) propanamide; and
2-amino-N—((R)-4-(4-(fluoromethyl)-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide;
or a pharmaceutically acceptable salt thereof.

[21] A pharmaceutical composition comprising a compound or a pharmaceutically acceptable salt thereof, as described in any one of [14] to [20], and a pharmaceutically acceptable carrier.

[22] The pharmaceutical composition as described in [21], further comprising another pharmacologically active agent.

[23] A method of treatment of an animal including human suffering from a condition or disorder mediated by the ghrelin receptor, which comprises administering to the said subject an effective amount of a compound of the formula (I) or a pharmaceutically acceptable salt according to any one of [14] to [20].

[24] The method as described in [23], wherein the said condition or disorder is selected from the group consisting of: cancer anorexia/cachexia; cachexia and anorexia by anti-cancer drugs; hyperalgesia by anti-cancer drugs;

COPD/COPD cachexia; sarcopenia; eating disorders and neurological eating disorders; weight loss suppression; early postoperative recovery of cancer patients; chronic respiratory tract infection; inflammation; IBD; FD; constipation; diabetic gastroparesis and gastroparesis; heart failure; myocardial infarction; diabetic neuropathy; Parkinson's disease; multiple sclerosis; diagnosis and treatment of growth hormone deficiency; elderly QOL improvement; bowel movement disturbance of spinal cord injury patients; postoperative ileus; and morphine induced ileus.
and combinations thereof.

[25] A use of a compound described in any one of [14] to [20] or a pharmaceutically acceptable salt, or composition thereof for the manufacture of a medicament for the treatment of a condition or disorder mediated by the ghrelin receptor.

[26] The use as described in [25], wherein the said condition or disorder is selected from the group consisting of: cancer anorexia/cachexia; cachexia and anorexia by anti-cancer drugs; hyperalgesia by anti-cancer drugs; COPD/COPD cachexia; sarcopenia; eating disorders and neurological eating disorders; weight loss suppression; early post-operative recovery of cancer patients; chronic respiratory tract infection; inflammation; IBD; FD; constipation; diabetic gastroparesis and gastroparesis; heart failure; myocardial infarction; diabetic neuropathy; Parkinson's disease; multiple sclerosis; diagnosis and treatment of growth hormone deficiency; elderly QOL improvement; bowel movement disturbance of spinal cord injury patients; postoperative ileus; and morphine induced ileus;
and combinations thereof.

[27] A compound described in any one of [14] to [20] a pharmaceutically acceptable salt for the use in the treatment of a condition or disorder mediated by the ghrelin receptor.

[28] A process for preparing a pharmaceutical composition comprising mixing a compound described in any one of [14] to [20] or a pharmaceutically acceptable salt thereof with a pharmaceutically acceptable carrier, diluent or excipient.

Advantageous Effects of Invention

The tetrahydropyrazolopyridine derivatives of the present invention are ghrelin receptor agonists and have a number of therapeutic applications, particularly in the treatment of cancer anorexia/cachexia; cachexia and anorexia by anticancer drugs; hyperalgesia by anti-cancer drugs; COPD/COPD cachexia; sarcopenia; eating disorders and neurological eating disorders; weight loss suppression; early postoperative recovery of cancer patients; chronic respiratory tract infection; inflammation; IBD; FD; constipation; diabetic gastroparesis and gastroparesis; heart failure; myocardial infarction; diabetic neuropathy; Parkinson's disease; multiple sclerosis; diagnosis and treatment of growth hormone deficiency; elderly QOL improvement; bowel movement disturbance of spinal cord injury patients; postoperative ileus; and morphine induced ileus.

As illustrated in the following Scheme I, the present invention is characterized by amino acid moiety in the center parts. Pfizer Inc., discloses ghrelin receptor agonist in WO97/24369, which is regarded as a structurally close art. The closest compound is thought to be a compound of the example 180 in the WO97/24369, wherein $R^2$ is $CH_2$-phenyl illustrated in Scheme II. The tetrahydropyrazolopyridine derivatives of the present invention are much better metabolic stability in human liver microsomes (hereafter this may be called HLM).

As shown in Table 6, in the present invention, when $R^2$ is phenyl, $CH_2$-phenyl ($CH_2OH$), and $CH_2$-pyridyl, the metabolic stability has been dramatically improved. In particular, when $R^2$ is $CH_2$-phenyl, introducing —$CH_2OH$ group to the phenyl ring surprisingly leads to improve the metabolic stability in HLM comparing with the compound disclosed in WO97/24369, while the ghrelin receptor agonistic activities of the present invention are similar to those in the closest known compound.

Scheme I: tetrahydropyrazolopyridine derivative

[Chem. 2]

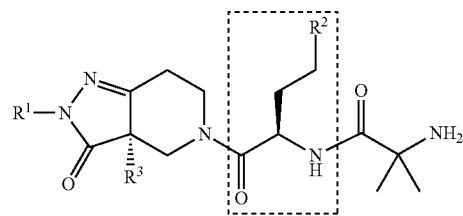

Scheme II: Compound in WO97/24369 ( R = $CH_2$-phenyl)

[Chem. 3]

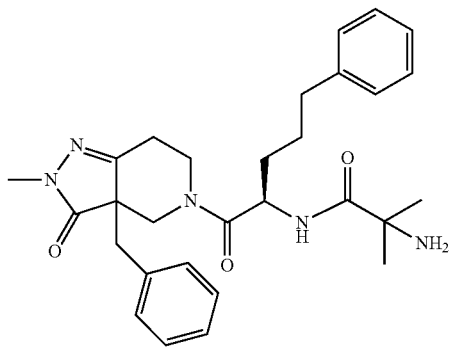

With respect to other compounds disclosed in the art, the compounds of the present invention can show less toxicity, good absorption and distribution, good solubility, less plasma protein binding, less drug-drug interaction, good metabolic stability, reduced inhibitory activity at HERG (human Ether-a-go-go-Related Gene) channel, and/or reduced QT prolongation.

DESCRIPTION OF EMBODIMENTS

As appreciated by those of skill in the art, "halogen" or "halo" as used herein is intended to include fluoro, chloro, bromo and iodo. Similarly, 1-6, as in $C_{1-6}$ is defined to identify the number as having 1, 2, 3, 4, 5 or 6. According to the definition, for example, $C_{1-6}$, as in $C_{1-6}$ alkyl is defined to identify the alkyl group as having 1, 2, 3, 4, 5 or 6 carbons. A group which is designated as being independently substituted with substituents may be independently substituted with multiple numbers of such substituents.

The term "alkyl", as used herein, means a linear saturated monovalent hydrocarbon radical or a branched saturated monovalent hydrocarbon radical, e.g., methyl, ethyl, propyl, 2-propyl, butyl (including all isomeric forms), pentyl (including all isomeric forms), and the like.

As used herein, the term "treatment" refers to alleviating the specified condition, eliminating or reducing the symptoms of the condition, slowing or eliminating the progression of the condition, and preventing or delaying the reoccurrence of the condition in a previously afflicted patient or subject.

As used herein, the term "evening" refers to from around 16:00 to 24:00, preferably from around 17:00 to 20:00.

As used herein, the article "a" or "an" refers to both the singular and plural form of the object to which it refers unless indicated otherwise.

The term "animal," as used herein, includes a mammalian subject or a non-mammalian subject. Examples of suitable mammalian subject may include, without limit, human, rodents, companion animals, livestock, and primates. Suitable rodents may include, but are not limited to, mice, rats, hamsters, gerbils, and guinea pigs. Suitable companion animals may include, but are not limited to, cats, dogs, rabbits, and ferrets. Suitable livestock may include, but are not limited to, horses, goats, sheep, swine, cattle, llamas, and alpacas. Suitable primates may include, but are not limited to, chimpanzees, lemurs, macaques, marmosets, spider monkeys, squirrel monkeys, and vervet monkeys. Examples of suitable non-mammalian subject may include, without limit, birds, reptiles, amphibians, and fish. Non-limiting examples of birds include chickens, turkeys, ducks, and geese. The preferred mammalian subject is a human.

Salts of the compounds of the present invention are also encompassed within the scope of the present invention. Because of their potential use in medicine, the salts of the compounds of formula (I) are preferably pharmaceutically acceptable. Suitable pharmaceutically acceptable salts can include acid addition salts. A pharmaceutically acceptable acid addition salt can be formed by reaction of a compound of formula (I) with a suitable inorganic or organic acid (such as hydrobromic, hydrochloric, hydroiodic, sulfuric, nitric, phosphoric, p-toluenesulfonic, methanesulfonic or naphthalenesulfonic acid), optionally in a suitable solvent such as an organic solvent, to give the salt which is usually isolated for example, by crystallisation and filtration. Examples of pharmaceutically acceptable acid addition salts of a compound of formula (I) include HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate salts. For reviews on suitable pharmaceutical salts, see Berge et al, J. Pharm, ScL, 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497. Other salts which are not pharmaceutically acceptable, for example the trifluoroacetate salt, may be useful in the preparation of compounds of the present invention and these form a further aspect of the present invention. The present invention includes within its scope all possible stoichiometric and non-stoichiometric forms of the salts of the compounds of formula (I).

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the present invention are within the scope of the invention.

Salts and solvates having non-pharmaceutically acceptable counter-ions or associated solvents are within the scope of the present invention, for example, for use as intermediates in the preparation of other compounds of formula (I) and their pharmaceutically acceptable salts.

Compounds of formula (I) may have polymorphs in crystalline form, which are within the scope of the present invention.

Also within the scope of the invention are so-called "prodrugs" of the compounds of formula (I). Thus certain derivatives of compounds of formula (I) which may have little or no pharmacological activity themselves, when they are administered into or onto the body, can be converted into compounds of formula (I) having the desired activity, for example, by hydrolytic or hydrolysis cleavage. Such derivatives are referred to as "prodrugs". Further information on the use of prodrugs may be found in Pro-drugs as Novel Delivery Systems, Vol. 14, ACS Symposium Series (T Higuchi and W Stella) and Bioreversible Carriers in Drug Design, Pergamon Press, 1987 (ed. E B Roche, American Pharmaceutical Association).

Prodrugs in accordance with the present invention for example, can be produced by replacing appropriate functionalities presenting in the compounds of formula (I) with certain moieties known to those skilled in the art as 'promoieties' as described, for example, in Design of Prodrugs by H. Bundgaard (Elsevier, 1985). Some examples of prodrugs in accordance with the present invention include:

(i) where the compound of formula (I) contains an alcohol functionality (—OH), compounds wherein the hydroxy group is replaced with a moiety convertible in vivo into the hydroxy group. The said moiety convertible in vivo into the hydroxy group means a moiety transformable in vivo into a hydroxy group by e.g. hydrolysis and/or by an enzyme, e.g. an esterase. Examples of the said moiety include, but are not limited to, ester and ether groups which may be hydrolyzed easily in vivo. Preferred are the moieties replaced the hydrogen of hydroxy group with acyloxyalkyl, 1-(alkoxycarbonyloxy)alkyl, phthalidyl and acyloxyalkyloxycarbonyl such as pivaloyloxymethyloxycarbonyl; and (ii) where the compound of the formula (I) contains an amino group, a pyrrolopyridinone derivative prepared by reacting with a suitable acid halide or a suitable acid anhydride is exemplified as a prodrug. A particularly preferred pyrrolopyridinone derivative as a prodrug is —NHCO(CH$_2$)$_2$OCH$_3$, —NHCOCH(NH$_2$)CH$_3$ or the like.

Further examples of replacement groups in accordance with the foregoing examples and examples of other prodrug types may be found in the aforementioned references.

Additionally, the compounds of formula (I) may be administered as prodrugs. As used herein, a "prodrug" of a compound of formula (I) is a functional derivative of the compound, upon administration to a patient, which eventually liberates the compound of formula (I) in vivo. Administration of a compound of formula (I) as a prodrug may enable the skilled artisan to do one or more of the following: (a) to modify the onset of action of the compound in vivo; (b) to modify the duration of action of the compound in vivo; (c) to modify the transportation or distribution of the compound in vivo; (d) to modify the solubility of the compound in vivo; and (e) to overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In certain of the compounds of formula (I), there may be one or more chiral carbon atoms. In such cases, the compounds of formula (I) may exist as stereoisomers. The invention may be extended to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

The certain of the compounds herein can exist in various tautomeric forms and it is to be understood that the invention encompasses all of such tautomeric forms.

The present invention also includes all suitable isotopic variations of a compound of the invention. An isotopic variation of a compound of the invention is defined as the one in which at least one atom is replaced by an atom having the same atomic number but an atomic mass different from the atomic mass usually found in nature. Examples of isotopes that can be incorporated into compounds of the present invention include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$, and $^{36}Cl$, respectively. Certain isotopic variations of the present invention, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of the invention can be generally prepared by any conventional procedures such as by the illustrative methods or by the preparations described in the compounds hereafter using any appropriate isotopic variations of suitable reagents.

In a further embodiment the present invention also provides the compounds of formula (I) and pharmaceutically acceptable salts or solvates thereof, for use in medical therapy, and particularly in the treatment of disorders mediated by the ghrelin receptor.

In a further embodiment the present invention is directed to methods of modulating ghrelin receptor activity for the present prevention and/or treatment of disorders mediated by the ghrelin receptor.

In a further embodiment the present invention provides a method of treatment of an animal including human suffering from a disorder mediated by the ghrelin receptor, which comprises administering to the said subject an effective amount of a compound of formula (I) or a pharmaceutically acceptable salt or solvate thereof. Such treatment comprises the step of administering a therapeutically effective amount of the compound of formula (I), including a pharmaceutically acceptable salt or solvate thereof. Such treatment can also comprise the step of administering a therapeutically effective amount of a pharmaceutical composition containing a compound of formula (I), including a pharmaceutically acceptable salt or solvate thereof.

A further embodiment of the present invention provides the use of a compound of formula (I), or a pharmaceutically acceptable salt or solvate thereof, in the preparation of a medicament for the treatment of a disorder mediated by the ghrelin receptor.

The action of the endogenous ligand ghrelin at the ghrelin receptor has been shown to result in potent growth-hormone releasing activity, appetite stimulation, stimulation of gastric motility and acid secretion, positive cardiovascular effects and direct action on bone formation. Thus, a ghrelin receptor modulator may achieve a beneficial effect in the treatment of growth-hormone deficiencies, eating disorders, gastrointestinal diseases, cardiovascular diseases, osteoporosis, aging and catabolic states or chronic wasting syndromes (Kojima and Kangawa, Nature Clinical Practice, February 2006, Vol. 2, No. 2, 80-88). A ghrelin receptor modulator may also achieve a beneficial effect in the treatment of sleep disorders (Brain Research, 1088 (2006) 131-140).

Particular disorders which are associated with the ghrelin receptor and thus may be mediated by the ghrelin receptor such that a ghrelin receptor modulator may achieve a beneficial effect include obesity and risk factors associated with obesity, including but not limited to diabetes, complications associated with diabetes, metabolic syndromes, and cardiovascular disorders (including atherosclerosis and dyslipidemia).

Other diseases and/or conditions mediated by the ghrelin receptor wherein a ghrelin include the following, treating a growth hormone deficient state, increasing muscle mass, increasing bone density, treating sexual dysfunction in males and females, facilitating a weight gain, facilitating weight maintenance, facilitating appetite increase (for example facilitating weight gain, maintenance or appetite increase is useful in a patient having a disorder, or undergoing a treatment, accompanied by weight loss). Examples of diseases or disorders accompanied by weight loss include anorexia, bulimia, cancer cachexia, AIDS, wasting, cachexia and wasting in frail elderly. Examples of treatments accompanied by weight loss include chemotherapy, radiation therapy, temporary or permanent immobilisation, and dialysis.

Further diseases or conditions include sleep disorders, congestive heart failure, metabolic disorder, improvements in memory function, breast cancer, thyroid cancer, ameliorating ischemic nerve or muscle damage.

The compounds of the present invention function by modulating the activity of the ghrelin receptor. They may activate/inactivate the receptor by acting as an agonist, partial agonist, inverse agonist, antagonist or partial antagonist.

Eating disorders include Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50). [The numbers in brackets after the listed diseases above refer to the classification code in Diagnostic and Statistical Manual of Mental Disorders, 4th Edition, published by the American Psychiatric Association (DSM-IV) and/or the International Classification of Diseases, 10th Edition (ICD-10)].

In a further embodiment the present invention provides the use of a compound of formula (I), or a pharmaceutically acceptable salt or solvate thereof, in the preparation of a medicament for the treatment of an eating disorder.

In a further embodiment the present invention provides a method of treatment of an animal including human suffering from an eating disorder which comprises administering to the said subject an effective amount of a compound of formula (I) or a pharmaceutically acceptable salt or solvate thereof.

Gastrointestinal diseases include gastric ileus, gastric ulcer and inflammatory bowel diseases such as Crohn's disease and ulcerative colitis. The compounds of the present invention may also be useful for treatments to alleviate symptoms associated with gastro-esophageal reflux and/or with dyspepsia, with or without appetite/metabolic-related cachexia, and in the treatment of paralytic ileus or pseudo obstruction, and of conditions associated with constipation, such as constipation-pre-dominant irritable bowel syndrome.

Cardiovascular diseases include heart failure and dilated cardiomyopathy.

Catabolic states or chronic wasting syndromes may be seen in post-operative patients and also include AIDS-associated and cancer-associated wasting syndromes, such as cancer cachexia.

While it is possible that, for use in therapy a therapeutically effective amount of a compound of formula (I), or a pharmaceutically acceptable salt or solvate thereof, may be administered as the raw chemical, it is possible to present the active ingredient as a pharmaceutical composition. Thus, in a further embodiment the present invention provides a pharmaceutical composition comprising a compound of formula (I), or a pharmaceutically acceptable salt or solvate thereof, in the mixture with one or more pharmaceutically acceptable carriers, diluents, or excipients. The carrier(s), diluent(s) or excipient(s) is preferably be acceptable in the sense of being compatible with the other ingredients of the formulation and not deleterious to the recipient thereof. In a further embodiment the present invention also provides a process for the preparation of a pharmaceutical composition including mixing a compound of the formula (I), or a pharmaceutically acceptable salt or solvate thereof, with one or more pharmaceutically acceptable carriers, diluents or excipients.

Pharmaceutical compositions of the present invention may be formulated for administration by any appropriate route, for example by the oral including buccal or sublingual, rectal, nasal, topical including buccal, sublingual or transdermal, vaginal or parenteral including subcutaneous, intramuscular, intravenous or intradermal routes. Therefore, the pharmaceutical compositions of the present invention may be formulated, for example, as tablets, capsules, powders, granules, lozenges, creams or liquid preparations, such as oral or sterile parenteral solutions or suspensions. Such pharmaceutical formulations may be prepared by any methods known in the art of pharmacy, for example by bringing into association the active ingredient with the carrier(s) or excipient(s).

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example; lactose, sugar, maize-starch, calcium phosphate, sorbitol or glycine; tableting lubricants, for example; magnesium stearate, talc, polyethylene glycol or silica; disintegrants, for example; potato starch; or acceptable wetting agents such as sodium lauryl sulphate. The tablets may be coated according to any methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan monooleate, or acacia; non-aqueous vehicles which may include edible oils, for example, almond oil, oily esters such as glycerine, propylene glycol or ethyl alcohol; preservatives, for example methyl or propyl p-hydroxybenzoate or sorbic acid, and, if desired, conventional flavouring or colouring agents.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules, and tablets.

Pharmaceutical formulations adapted for rectal administration may be presented as suppositories or as enemas.

Pharmaceutical formulations adapted for nasal administration wherein the carrier is a solid may include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as nasal sprays or as nasal drops, include aqueous or oil solutions of the active ingredients.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

It should be understood that in addition to the ingredients particularly mentioned above, the formulations may include other agents conventional in the art having regard to the type of formulation in question.

A therapeutically effective amount of a compound of formula (I), or a pharmaceutically acceptable salt or solvate thereof will depend upon a number of factors including, for example, the age and weight of the human or other animal, the precise condition requiring treatment and its severity, the nature of the formulation, and the route of administration, and will be ultimately at the discretion of the attendant physician or veterinarian. However, an effective amount of a compound of formula (I) for the treatment of disorders mediated by the ghrelin receptor will generally be in the range of 0.1 to 100 mg/kg body weight of recipient (animal) per day and more usually in the range of 1 to 10 mg/kg body weight per day. Thus, for a 70 kg adult animal, the actual amount per day would be usually from 70 to 700 mg and this amount may be given in a single dose per day or more usually in a number (such as two, three, four, five or six) of sub-doses per day such that the total daily dose is the same.

An effective amount of a pharmaceutically acceptable salt or solvate thereof, may be determined as a proportion of the effective amount of the compound of formula (I) per se.

A compound of formula (I), or a pharmaceutically acceptable salt or solvate thereof for use in the instant invention may be used in combination with one or more other therapeutic agents. The present invention thus provides in a further embodiment a combination comprising a compound of formula (I), or a pharmaceutically acceptable salt or solvate thereof together with a further therapeutic agent, which may be for example an additional anti-obesity agent. In a yet further embodiment the present invention also provides the use of a combination comprising a compound of formula (I), or a pharmaceutically acceptable salt or solvate thereof with a further therapeutic agent in the treatment of disorders mediated by the ghrelin receptor.

When a compound of formula (I), or a pharmaceutically acceptable salt or solvate thereof is used in combination with one or more other therapeutic agents, the compounds may be administered either sequentially or simultaneously by any convenient route.

The combinations referred to the above may be conveniently presented for use in the form of a pharmaceutical formulation and thus pharmaceutical formulations comprising a combination as the defined above optimally together with a pharmaceutically acceptable carrier or excipient comprise a further embodiment of the present invention. The individual components of such combinations may be administered either sequentially or simultaneously in separate or combined pharmaceutical formulations.

When combined in the same formulation, it will be appreciated that the two compounds must be stable and compatible with each other and the other components of the formulation and may be formulated for administration. When formulated separately, they may be provided in any convenient formulation, conveniently in such a manner as are known for such compounds in the art.

When a compound is used in combination with a second therapeutic agent active against the same disease, the dose of each compound may differ from that when the compound is used alone. Appropriate doses will be readily appreciated by those skilled in the art.

The compounds of the present invention may be usefully combined with another pharmacologically active compound, or with two or more other pharmacologically active compounds, particularly in the treatment of a disorder mediated by the ghrelin receptor. For example, a ghrelin receptor agonist, particularly a compound of formula (I), or a prodrug thereof or a pharmaceutically acceptable salt or solvate thereof, as defined above, may be administered simultaneously, sequentially or separately in combination with one or more agents selected from;

- an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;
- a nonsteroidal antiinflammatory drug (NSAID), e.g. aspirin, diclofenac, diflunisal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;
- a barbiturate sedative, e.g. amobarbital, aprobarbital, butabarbital, butalbital, mephobarbital, metharbital, methohexital, pentobarbital, phenobartital, secobarbital, talbutal, thiamylal or thiopental;
- a benzodiazepine having a sedative action, e.g. chlordiazepoxide, clorazepate, diazepam, flurazepam, lorazepam, oxazepam, temazepam or triazolam;
- an H1 antagonist having a sedative action, e.g. diphenhydramine, pyrilamine, promethazine, chlorpheniramine or chlorcyclizine;
- a sedative such as glutethimide, meprobamate, methaqualone or dichloralphenazone;
- a skeletal muscle relaxant, e.g. baclofen, carisoprodol, chlorzoxazone, cyclobenzaprine, methocarbamol or orphrenadrine;
- an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex(registered trademark), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl}-3,4-dihydro-2(1H)-quinolinone;
- an alpha-adrenergic, e.g. doxazosin, tamsulosin, clonidine, guanfacine, dexmedetomidine, modafinil, or 4-amino-6,7-dimethoxy-2-(5-methane-sulfonamido-1, 2,3,4-tetrahydroisoquinol-2-yl)-5-(2-pyridyl) quinazoline;
- a tricyclic antidepressant, e.g. desipramine, imipramine, amitriptyline or nortriptyline;
- an anticonvulsant, e.g. carbamazepine, lamotrigine, topiramate or valproate;
- a tachykinin (NK) antagonist, particularly an NK-3, NK-2 or NK-1 antagonist, e.g. (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637) 5-[[(2R,3S)-2-R1R)-1-[3,5-bis(trifluoromethyl)phenyl] ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy) phenyl]-methylamino]-2-phenylpiperidine (2S,3S);
- a muscarinic antagonist, e.g. oxybutynin, tolterodine, propiverine, trospium chloride, darifenacin, solifenacin, temiverine and ipratropium;
- a COX-2 selective inhibitor, e.g. celecoxib, rofecoxib, parecoxib, valdecoxib, deracoxib, etoricoxib, or lumiracoxib;
- a coal-tar analgesic, in particular paracetamol;
- a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion (registered trademark) or sarizotan;
- a vanilloid receptor agonist (e.g. resiniferatoxin) or antagonist (e.g. capsazepine);
- a transient receptor potential cation channel subtype (V1, V2, V3, V4, M8, A1) agonist or antagonist;

a beta-adrenergic such as propranolol;
a local anaesthetic such as mexiletine;
a corticosteroid such as dexamethasone;
a 5-HT receptor agonist or antagonist, particularly a 5-HT1B/1D agonist such as eletriptan, sumatriptan, naratriptan, zolmitriptan or rizatriptan;
a 5-HT2A receptor antagonist such as R(+)-alpha-(2,3-dimethoxy-phenyl)-1-[2-(4-fluorophenylethyl)]-4-piperidinemethanol (MDL-100907);
a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;
Tramadol(registered trademark);
a PDEV inhibitor, such as
5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil),
(6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil),
2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil),
5-(5-acetyl-2-butoxy-3-pyridinyl)-3-ethyl-2-(1-ethyl-3-azetidinyl)-2,6-dihydro-7H-pyrazolo[4,3-d]pyrimidin-7-one,
5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one,
5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one,
4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide,
3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;
an alpha-2-delta ligand such as gabapentin, pregabalin, 3-methylgabapentin, (1alpha,3alpha,5alpha)(3-aminomethyl-bicyclo[3.2.0]hept-3-yl)-acetic acid,
(3S,5R)-3aminomethyl-5 methyl-heptanoic acid, (3S,5R)-3amino-5 methyl-heptanoic acid, (3S,5R)-3amino-5 methyl-octanoic acid, (2S,4S)-4-(3-chlorophenoxy)proline, (2S,4S)-4-(3-fluorobenzyl)-proline,
[(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine,
(3S,4S)-(1-aminomethyl-3,4-dimethyl-cyclopentyl)-acetic acid, (3S,5R)-3 aminomethyl-5 methyl-octanoic acid, (3S,5R)-3amino-5 methyl-nonanoic acid,
(3S,5R)-3amino-5 methyl-octanoic acid, (3R,4R,5R)-3-amino-4,5-dimethyl-heptanoic acid and (3R,4R,5R)-3-amino-4,5-dimethyl-octanoic acid;
a cannabinoid;
a metabotropic glutamate subtype 1 receptor (mGluR1) antagonist;
a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;
a noradrenaline (norepinephrine) reuptake inhibitor, such as maprotiline, lofepramine, mirtazapine, oxaprotiline, fezolamine, tomoxetine, mianserin, buprorion, buprorion metabolite hydroxybuprorion, nomifensine and viloxazine (Vivalan (registered trademark)), especially a selective noradrenaline reuptake inhibitor such as reboxetine, in particular (S,S)-reboxetine;
a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;
an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thiol]-5-chloro-3-pyridinecarbonitrile; 2-[[(1R,3S)-3-amino-4-hydroxy-1-(5-thiazolyl)butyl]thiol]-4-chlorobenzonitrile, (2S,4R)-2-amino-4-[[2-chloro-5-(trifluoromethyl)phenyl] thiol]-5-thiazolebutanol,
2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl] thiophene-2-carboxamidine, or guanidinoethyldisulfide;
an acetylcholinesterase inhibitor such as donepezil;
a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or
4-[(1S)-1-({[5-chloro-2-(3-fluorophenoxy)pyridin-3-yl]carbonyl}amino)ethyl]benzoic acid;
a leukotriene B4 antagonist; such as
1-(3-biphenyl-4-ylmethyl-4-hydroxy-chroman-7-yl)-cyclopentanecarboxylic acid (CP-105696),
5-[2-(2-Carboxyethyl)-3-[6-(4-methoxyphenyl)-5E-hexenyl]oxyphenoxy]-valeric acid (ONO-4057) or DPC-11870,
a 5-lipoxygenase inhibitor, such as zileuton,
6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504);
a sodium channel blocker, such as lidocaine;
a calcium channel blocker, such as ziconotide, zonisamide, mibefradil;
a 5-HT3antagonist, such as ondansetron;
a chemotherapy drug such as oxaliplatin, 5-fluorouracil, leucovorin, paclitaxel;
a calcitonin gene related peptide (CGRP) antagonist;
a bradykinin (BK1 and BK2) antagonist;
a voltage gated sodium dependent channel blocker ($Na_{v1.3}$, $Na_{v1.7}$, $Na_{v1.8}$);
a voltage dependent calcium channel blocker (N-type, T-type);
a P2X (ion channel type ATP receptor) antagonist;
an acid-sensing ion channel (ASIC1a, ASIC3) antagonist;
an Angiotensin AT2 antagonist;
a Chemokine CCR2B receptor antagonist;
a Cathepsin (B, S, K) inhibitor;
a signal receptor agonist or antagonist;
and the pharmaceutically acceptable salts and solvates thereof.

Such combinations offer significant advantages, including synergistic activity, in therapy.

All publications, including but not limited to patents and patent applications, cited in this specification are herein incorporated by reference as if each individual publication was specifically and individually indicated to be incorporated by reference herein as though fully set forth.

General Synthesis

Throughout the instant application, the following abbreviations are used with the following meanings:

DCM Dichloromethane
DMA N,N-dimethylacetamide
DME 1,2-dimethoxyethane
DMF N,N-dimethylformamide
DMSO Dimethyl sulfoxide
EDC 1-Ethyl-3-(3-dimethylaminopropyl)carbodiimide Hydrochloride
EtOAc Ethyl acetate
EtOH ethanol
ESI Electrospray ionization
HOBT 1-Hydroxybenztriazole
HBTU O-(Benzotriazol-1-yl)-N,N,N',N'-tetramethyluronium Hexafluorophosphate
HPLC High pressure liquid chromatography
LC liquid chromatography
LG Leaving group
MeCN Acetonitrile
MeOH methanol
MHz Megahertz
MS Mass spectrometry
NMR Nuclear magnetic resonance
PG Protecting group
T3P 2,4,6-tripropyl-1,3,5,2,4,6-trioxatriphosphinane 2,4,6-trioxide
TBME Methyl tert-butyl ether
TFA Trifluoroacetic acid
THF Tetrahydrofuran
TLC Thin layer chromatography
tR Retention time
UV Ultraviolet The term of "base" is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, potassium phosphate, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, triethylamine, diisopropylethylamine, DBU, DBN, DABCO, pyridine, lutidine, colidine, sodium carbonate, sodium hydrogencarbonate, sodium hydroxide, potassium carbonate, potassium hydrogencarbonate, potassium hydroxide, potassium phosphate, barium hydroxide, and cesium carbonate are preferred.

The reactions are normally and preferably effected in the presence of inert solvents. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as dichloromethane, chloroform, carbon tetrachloride, and dichloroethane; ethers, such as diethyl ether, diisopropyl ether, THF, and dioxane; aromatic hydrocarbons, such as benzene, toluene and nitrobenzene; amides, such as, DMF, N,N-dimethylacetamide (DMA), and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; alcohols, such as methanol, ethanol, propanol, isopropanol, and butanol; nitriles, such as acetonitrile and benzonitrile; sulfoxides, such as dimethyl sulfoxide (DMSO) and sulfolane; ketones, such as acetone and diethylketone. Of these solvents, including but not limited to DMF, DMA, DMSO, THF, diethylether, diisopropylether, dimethoxyethane, acetonitrile, dichloromethane, dichloroethane and chloroform are preferred.

EXAMPLES

The present invention is illustrated in the following non-limiting examples in which, unless stated otherwise: all reagents are commercially available, all operations are carried out at room or ambient temperature, that is, in the range of about 18-25° C.; evaporation of solvent is carried out using a rotary evaporator under reduced pressure with a bath temperature of up to about 60° C.; reactions are monitored by thin layer chromatography (TLC) or LC-MS (low-resolution mass spectrum) and reaction times are given for illustration only; the structure and purity of all isolated compounds are assured by at least one of the following techniques: TLC (Merck silica gel 60 $F_{254}$ precoated TLC plates or Merck NH2 $F_{254}$ precoated HPTLC plates), mass spectrometry or NMR. Yields are given for illustrative purposes only. Flash column chromatography is carried out using Wakogel (registered trademark) C-300HGT or Fuji Silysia Chromatorex (registered trademark) DM2035 (Amino Type, 30-50 micrometer) or Biotage silica (32-63 mm, KP-Sil) or Biotage amino bounded silica (35-75 mm, KP-NH). Low-resolution mass spectral data (ESI) are obtained by the following apparatus:

Apparatus; Waters Alliance 2695 HPLC system with UV2487 detector and ZQ2000 mass spectrometer.

The purification of compounds using HPLC (preparative LC-MS) is performed by the following apparatus and conditions.

Apparatus; Waters MS-trigger Auto-purification system,
Column; Waters XBridge C18, 19×50 mm, 5 micrometer particle size,
Condition A: Methanol or Acetonitrile/0.05% (v/v) Ammonia aqueous solution,
Condition B: Methanol or Acetonitrile/0.05% (v/v) Formic acid aqueous solution,
Conditions for determining HPLC retention time:
Method: QC1
Apparatus: Waters ACQUITY Ultra Performance LC with TUV detector and ZQ2000 mass spectrometer Column: Waters ACQUITY C18, 2.1×100 mm, 1.7 micrometer particle size
Column temperature: 60° C.
Flow rate: 0.7 mL/min
Run time: 3 min
UV detection: 210 nm
MS detection: ESI positive/negative mode
Mobile phases:
　A1: 10 mM Ammonium acetate
　B1: Acetonitrile
Table 1. Gradient program:

TABLE 1

| Time (min) | A1(%) | B1(%) |
|---|---|---|
| 0 | 95 | 5 |
| 0.1 | 95 | 5 |
| 1.8 | 5 | 95 |
| 2.3 | 95 | 5 |

Method: QC2
Apparatus: Waters Alliance2795 HPLC system with 2996PDA detector and ZQ2000 mass spectrometer
Column: XBridge C18, 4.6×50 mm, 3.5 micrometer particle size
Column temperature: 45° C.
Flow rate: 1.2 mL/min
Run time: 4.5 min
UV detection: 210-400 nm (scan range)
MS detection: ESI positive/negative mode
Mobile phases:
　A: Water
　B: Acetonitrile
　C: 1% Formic acid aqueous solution
　D: 1% Ammonia aqueous solution Table 2. Gradient program:

TABLE 2

| Time (min) | A (%) | B (%) | C (%) | D (%) |
|---|---|---|---|---|
| 0 | 85 | 10 | 2.5 | 2.5 |
| 0.2 | 85 | 10 | 2.5 | 2.5 |
| 3.2 | 0 | 95 | 2.5 | 2.5 |
| 3.7 | 0 | 95 | 2.5 | 2.5 |
| 3.71 | 85 | 10 | 2.5 | 2.5 |
| 4.5 | 85 | 10 | 2.5 | 2.5 |

NMR data are determined at 270 MHz (JEOL JNM-LA270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc. Chemical symbols have their usual meanings; M (mol(s) per liter), L (liter(s)), mL (milliliter(s)), g (gram(s)), mg (milligram(s)), mol (mole(s)), mmol (millimole(s)).

Each prepared compound is generally named by ChemBioDraw (Ultra, version 12.0, CambridgeSoft).

All of the tetrahydropyrazolopyridine derivatives of the formula (I) can be prepared by the procedures described in the general methods presented below or by the specific methods described in the Examples section and the Preparations section, or by routine modifications thereof. The present invention also encompasses any one or more of these processes for preparing the tetrahydropyrazolopyridine derivatives of formula (I), in addition to any novel intermediates used therein.

In the following general methods, descriptors are as previously defined for the tetrahydropyrazolopyridine derivatives of the formula (I) unless otherwise stated.

<Scheme A>

[Chem. 4]
R² is phenyl

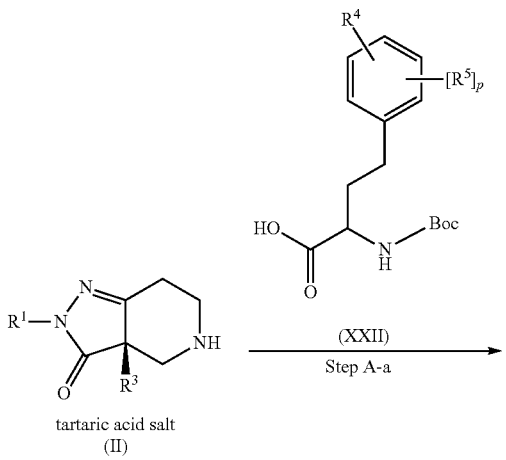

-continued

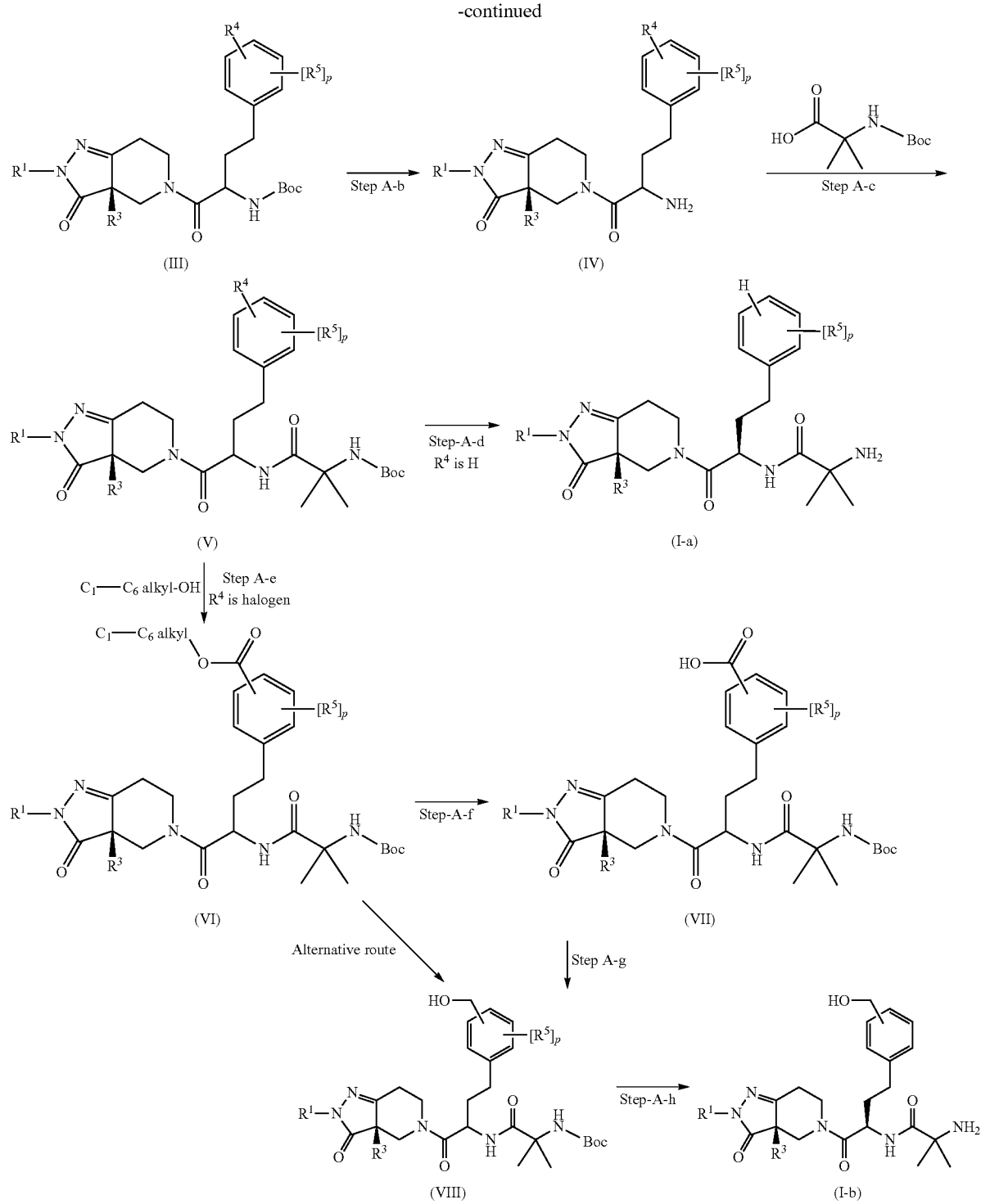

When R² is phenyl, a compound of formula (I-a) or (I-b) can be prepared as follows.

In Step A-a, a compound of formula (III) can be prepared from a tartarate compound of formula (II) by amidation with a compound of formula (XXII) using a suitable condensation reagent, but not limited to, such as T3P, HBTU and EDC-HOBT. The condensation can be carried out preferably under the presence of a base such as triethylamine and N,N-diisopropylethylamine in a suitable solvent such as EtOAc, THF, DMF, DMA and $CH_2Cl_2$ at a temperature from about −40 to 60° C. for about 1-24 hours.

In Step A-b, a compound of formula (IV) can be prepared from a compound of formula (III) by de-protection. De-protection can be conducted by the conventional methods known to those skilled in the art (typical amino protecting groups described in "Protective Groups in Organic Synthesis Fourth Edition" edited by T. W. Greene et al. (John Wiley & Sons, 2007)).

In Step A-c, a compound of formula (V) can be prepared from a compound of formula (IV) by amidation with 2-((tert-butoxycarbonyl)amino)-2-methylpropanoic acid using a suitable condensation reagent, but not limited to, such as T3P, HBTU and EDC-HOBT. The condensation can be carried out preferably under the presence of a base such as triethylamine and N,N-diisopropylethylamine in a suitable solvent such as EtOAc, THF, DMF, DMA and $CH_2Cl_2$ at a temperature from about 0 to 60° C. for about 1-24 hours.

In Step A-d, a compound of formula (I-a) can be prepared from a compound of formula (V) wherein $R^4$ is a H by de-protection reaction and purification using preparative LC-MS. De-protection can be conducted by the conventional methods known to those skilled in the art (typical amino protecting groups described in "Protective Groups in Organic Synthesis Fourth Edition" edited by T. W. Greene et al (John Wiley & Sons, 2007)). The compound of formula (I-a) can be isolated from a mixture of diastereomers by purification using preparative LC-MS.

In Step A-e, a compound of formula (VI) can be prepared from a compound of formula (V) wherein $R^4$ is a halogen by CO insertion reaction using a suitable catalysis, but not limited to, such as combination of palladium acetate (II) and 1,3-bis(diphenylphosphino)propane under CO atmosphere in the presence of alcohol in a suitable solvent such as EtOAc, THF, MeCN, DMF, DMA, EtOH, and MeOH. The reaction can be carried out at a temperature from about 0 to 150° C. for about 30 min to 72 hours. Alternatively, the reaction can be carried out with other carbon monoxide source such as phenyl formate/triethylamine and molybdenum hexacarbonyl.

In Step A-f, a compound of formula (VII) can be prepared by hydrolysis of the ester compound of formula (VI). The hydrolysis can be carried out by the conventional procedures. In a typical procedure, the hydrolysis is carried out under basic conditions, e.g. in the presence of sodium hydroxide, potassium hydroxide or lithium hydroxide. Suitable solvents include, but not limited to, water, MeOH, EtOH, propanol, butanol, 2-methoxyethanol, ethylene glycol, THF, DME, 1,4-dioxane, DMF, and DMA. The reaction can be carried out at a temperature from about 20 to 100° C. for from about 10 min to 24 hours.

In Step A-g, a compound of formula (VIII) can be prepared by reduction of the carboxylic acid compound of formula (VII) using a suitable reagent, but not limited to, such as $NaBH_4$-CDI and $BH_3$—THF. The reduction can be carried out in a suitable solvent, such as EtOAc, THF, DME, 1,4-dioxane, MeCN, DMF, DMA, EtOH, MeOH and water at a temperature from about −20 to 60° C. for about 5 min to 12 hours. Alternatively, a compound of formula (VIII) can be prepared by reduction of the ester compound formula (VI) with other reductant agent such as $LiBH_4$, $LiAH_4$ and diisobutylalminum hydride.

In Step A-h, a compound of formula (I-b) can be prepared from a compound of formula (VIII) by de-protection reaction and purification using preparative LC-MS. De-protection can be conducted by the conventional methods known to those skilled in the art (typical amino protecting groups described in "Protective Groups in Organic Synthesis Fourth Edition" edited by T. W. Greene et al (John Wiley & Sons, 2007)). The compound of formula (I-b) can be isolated from a mixture of diastereomers by purification using preparative LC-MS.

<Scheme B>

[Chem. 5]

$R^2$ is $CH_2$-phenyl($CH_2OH$) or $CH_2$-pyridyl

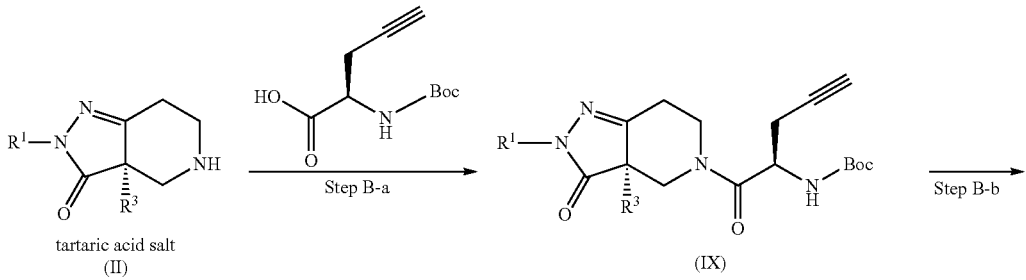

tartaric acid salt
(II)

Step B-a (IX)

Step B-b

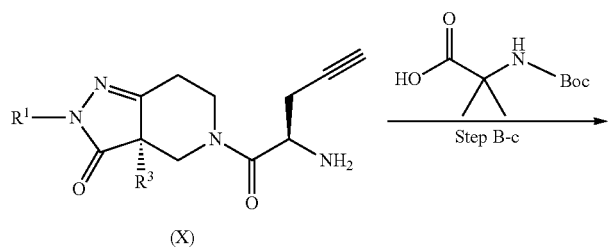

(X)

Step B-c

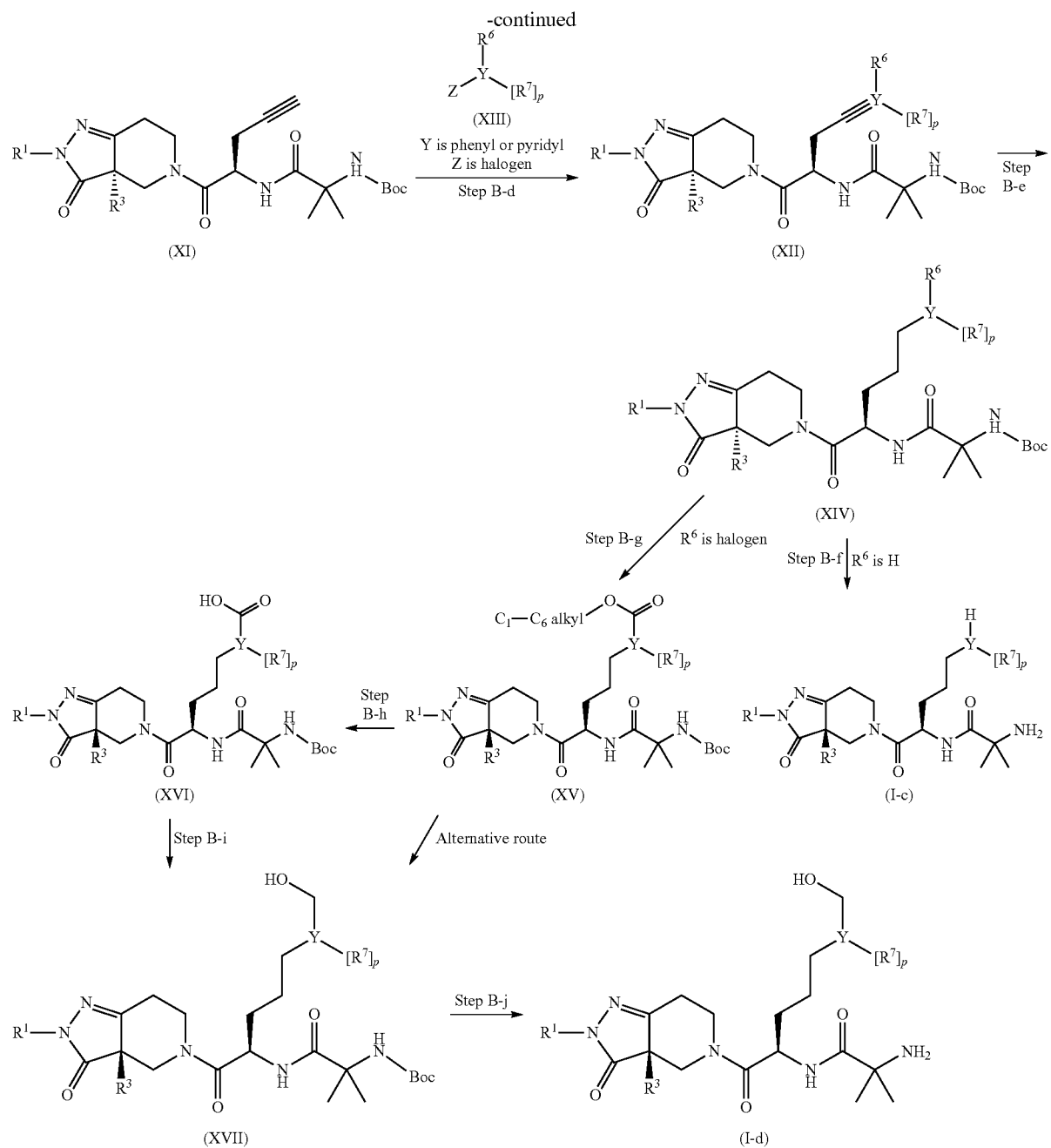

When $R^2$ is $CH_2$-phenyl($CH_2OH$) or $CH_2$-pyridyl, a compound of formula (I-c) or (I-d) can be prepared as follows.

In Step B-a, a compound of formula (IX) can be prepared from a tartarate compound of formula (II) by amidation with (R)-2-((tert-butoxycarbonyl)amino)pent-4-ynoic acid using a suitable condensation reagent, but not limited to, such as T3P, HBTU and EDC-HOBT. The condensation can be carried out preferably under the presence of a base such as triethylamine and N,N-diisopropylethylamine in a suitable solvent such as EtOAc, THF, DMF, DMA and $CH_2Cl_2$ at a temperature from about −40 to 60° C. for about 1-24 hours.

In Step B-b, a compound of formula (X) can be prepared from a compound of formula (IX) by de-protection. De-protection can be conducted by the conventional methods known to those skilled in the art (typical amino protecting groups described in "Protective Groups in Organic Synthesis Fourth Edition" edited by T. W. Greene et al (John Wiley & Sons, 2007)).

In Step B-c, a compound of formula (XI) can be prepared from a compound of formula (X) by amidation with 2-((tert-butoxycarbonyl)amino)-2-methylpropanoic acid using a suitable condensation reagent, but not limited to, such as T3P, HBTU and EDC-HOBT. The condensation can be carried out preferably under the presence of a base such as triethylamine and N,N-diisopropylethylamine in a suitable solvent such as EtOAc, THF, DMF, DMA and $CH_2Cl_2$ at a temperature from about 0 to 60° C. for about 1-24 hours.

In Step B-d, a compound of formula (XII) can be prepared by Sonogashira coupling reaction with a compound of formula (XI) and an aryl halide compound of formula (XIII)

The reaction can be carried out in the presence of a palladium catalysis, but not limited to, such as dichloro bis(triphenylphosphine) palladium, an additive such as copper (I) iodide and preferably under the presence of a base such as triethylamine and N,N-diisopropylethylamine in a suitable solvent such as EtOAc, MeCN, DME, THF, DMF, DMA, toluene and $CH_2Cl_2$ at a temperature from about −20 to 120° C. for about 30 min to 24 hours.

In Step B-e, a compound of formula (XIV) can be prepared by hydrogenation of the acetylene compound of formula (XII). The reaction can be carried out in the presence of a metal catalysis such as platinum (IV) oxide, palladium on carbon and palladium (II) hydroxide on carbon under hydrogen atmosphere in a suitable solvent such as EtOAc, DME, THF, EtOH and MeOH at a temperature from about 0 to 70° C. for about 1-24 hours. The reaction can be carried out with other hydrogen source such as formic acid, ammonium formate and 1,4-cyclohexadiene in a suitable solvent such as EtOH and MeOH.

In Step B-f, a compound of formula (I-c) can be prepared from a compound of formula (XIV) wherein $R^6$ is H by de-protection. De-protection can be conducted by the conventional methods known to those skilled in the art (typical amino protecting groups described in "Protective Groups in Organic Synthesis Fourth Edition" edited by T. W. Greene et al (John Wiley & Sons, 2007)).

In Step B-g, a compound of formula (XV) can be prepared from a compound of formula (XIV) wherein $R^6$ is a halogen by CO insertion reaction using a suitable catalysis, but not limited to, such as combination of palladium acetate (II) and 1,3-bis(diphenylphosphino)propane under CO atmosphere in the presence of alcohol in a suitable solvent such as EtOAc, THF, MeCN, DMF, DMA, EtOH, and MeOH. The reaction can be carried out at a temperature from about 0 to 150° C. for about 30 min to 72 hours. Alternatively, the reaction can be carried out with other carbon monoxide source such as phenyl formate/triethylamine and molybdenum hexacarbonyl.

In Step B-h, a compound of formula (XVI) can be prepared by hydrolysis of the ester compound of formula (XV). The hydrolysis can be carried out by the conventional procedures. In a typical procedure, the hydrolysis is carried out under basic conditions, e.g. in the presence of sodium hydroxide, potassium hydroxide or lithium hydroxide. Suitable solvents include, but not limited to, water, MeOH, EtOH, propanol, butanol, 2-methoxyethanol, ethylene glycol, THF, DME, 1,4-dioxane, DMF, and DMA. The reaction can be carried out at a temperature from about 20 to 100° C. for from about 10 min to 24 hours.

In Step B-i, a compound of formula (XVII) can be prepared by reduction of the carboxylic acid compound of formula (XVI) using a suitable reagent, but not limited to, such as $NaBH_4$—CDI and $BH_3$—THF. The reduction can be carried out in a suitable solvent, such as EtOAc, THF, DME, 1,4-dioxane, MeCN, DMF, DMA, EtOH, MeOH and water at a temperature from about −20 to 60° C. for about 5 min to 12 hours. Alternatively, a compound of formula (XVII) can be prepared by reduction of the ester compound formula (XV) with other reductant agent such as $LiBH_4$, $LiAH_4$ and diisobutylalminum hydride.

In Step B-j, a compound of formula (I-d) can be prepared from a compound of formula (XVII) by de-protection. De-protection can be conducted by the conventional methods known to those skilled in the art (typical amino protecting groups described in "Protective Groups in Organic Synthesis Fourth Edition" edited by T. W. Greene et al. (John Wiley & Sons, 2007)).

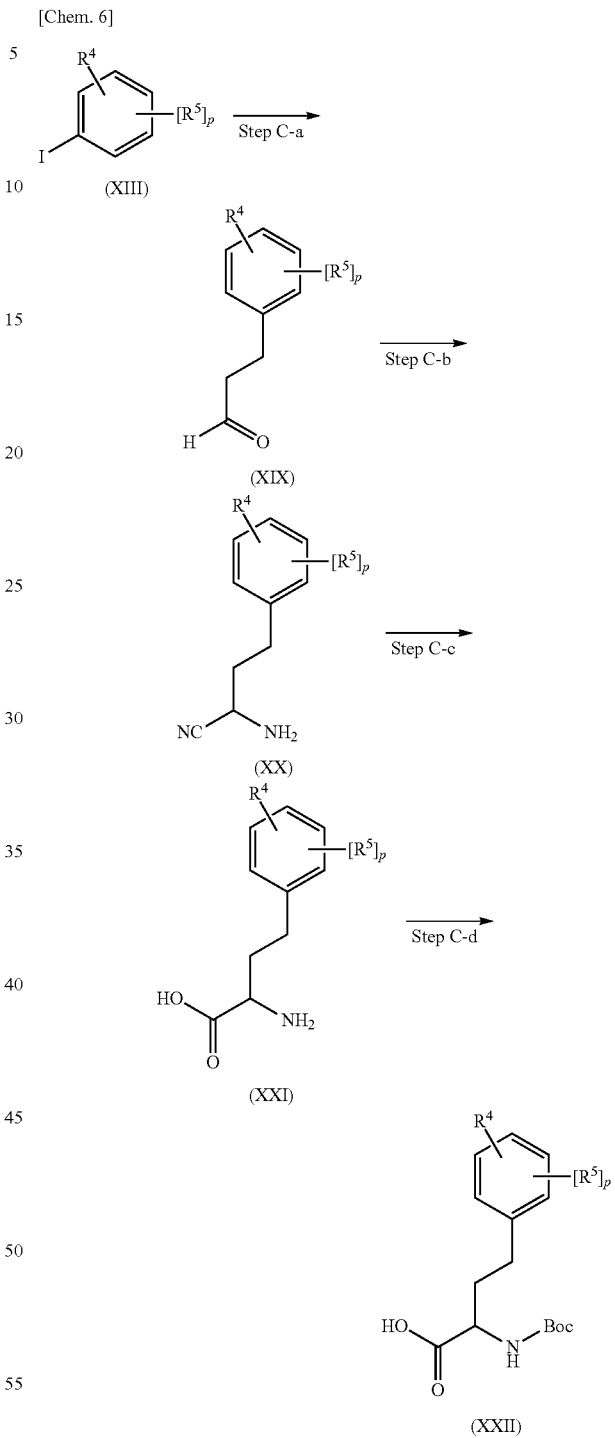

<Scheme C>

[Chem. 6]

In Step C-a, a compound of formula (XIX) can be prepared from a compound of formula (XIII) by Heck reaction with allylic alcohol. The reaction can be carried out in the presence of a palladium catalyst, but not limited to, such as palladium (II) acetate and tetrakis(triphenylphosphine)palladium and a base such as sodium bicarbonate, sodium carbonate, potassium carbonate, triethylamine and N,N-diisopropylethylamine. Preferably, an additive such as tetrabutylammonium chloride, benzyltrimethylammonium chloride and tetrabutylammonium bromide can be used for the reaction. Suitable solvents are DMF, DMA, THF, DME, 1,4-dioxane and triethylamine. The reaction can be carried out at a temperature from about 20 to 150° C. for about 1 to 48 hours.

In Step C-b, a compound of formula (XX) can be prepared from a compound of formula (XIX) by Strecker reaction. The reaction can be carried out in the presence of a cyanide source such as lithium cyanide, sodium cyanide, potassium cyanide and trimethylsilyl nitrile and ammonia in a suitable solvent such as THF, EtOH, MeOH and water at temperature from about 20 to 60° C. for about 1 to 24 hours.

In Step C-c, a compound of formula (XXI) can be prepared by hydrolysis reaction of the nitrile compound of formula (XX). The hydrolysis can be carried out by the conventional procedures. In a typical procedure, the hydrolysis is carried out under acidic conditions, e.g. in the presence of HCl and $H_2SO_4$ in a suitable solvent such as water, THF, DME and 1,4-dioxane. The reaction can be carried out at a temperature from about 20 to 100° C. for from about 10 min to 24 hours.

In Step C-d, compound of formula (XXII) can be prepared from a compound of formula (XXI) by protection of amino moiety. Protection can be carried out by the conventional methods known to those skilled in the art (typical amino protecting groups described in "Protective Groups in Organic Synthesis Fourth Edition" edited by T. W. Greene et al (John Wiley & Sons, 2007)).

All starting materials in the following general syntheses may be commercially available or obtained by the conventional methods known to those skilled in the art, otherwise noted in the intermediate synthesis part.

Nucleus Synthesis Part

Nucleus compounds are prepared according to WO97/24369. Names and structures of the nucleus compounds are shown in Table 3.

TABLE 3

| Nucleus | Name | Structure |
|---|---|---|
| 1 | (R)-3a-benzyl-2-methyl-4,5,6,7-tetrahydro-2H-pyrazolo[4,3-c]pyridin-3(3aH)-one (2R,3R)-2,3-dihydroxysuccinate | 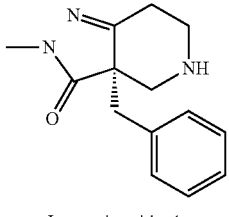<br>L-tartaric acid salt |
| 2 | (R)-3a-(pyridin-2-ylmethyl)-2-(2,2,2-trifluoroethyl)-4,5,6,7-tetrahydro-2H-pyrazolo[4,3-c]pyridin-3(3aH)-one (2S,3S)-2,3-dihydroxysuccinate | 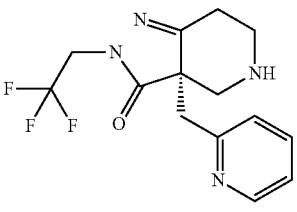<br>D-tartaric acid salt |

Intermediate Synthesis Part

Intermediate compounds are prepared as follows. Names and structures of the intermediate compounds are shown in Table 4.

Intermediate 1: 2-((tert-butoxycarbonyl) amino)-4-(2-(methylsulfonyl) phenyl) butanoic acid Step 1: 3-(2-(methylsulfonyl)phenyl)propanal Allyl alcohol (0.47 mL, 6.9 mmol), 1-iodo-2-(methylsulfonyl)benzene (1.3 g, 4.6 mmol), palladium (II) acetate (21 mg, 0.092 mmol), tetrabutylammonium chloride (1.3 g, 4.6 mmol) and sodium bicarbonate (0.97 g, 12 mmol) are dissolved in DMF (13 mL) in a flask. And then, the flask is replaced with nitrogen gas. The mixture is stirred at 40° C. The color of the mixture turned to dark red. After stirring for 18 hours, the mixture is diluted with water (30 mL) and EtOAc (100 mL) for separation. The organic layer is washed with water (40 mL×2), and dried over $Na_2SO_4$. After filtration, the filtrate is concentrated in vacuo. The residue is purified by column chromatography (silica gel, 5-30% EtOAc in hexane) to give the titled compound as a colorless oil (0.69 g, 70% yield).
$^1$H-NMR (270 MHz, $CDCl_3$) delta 9.83 (1H, s), 8.05 (1H, d, J=7.9 Hz), 7.58 (1H, dd, J=6.6, 6.6 Hz), 7.46-7.38 (2H, m), 3.31 (2H, t, J=7.4 Hz), 3.18 (3H, s), 2.95 (2H, t, J=7.4 Hz).

Step 2: 2-amino-4-(2-(methylsulfonyl)phenyl)butanenitrile

To a mixture of 3-(2-(methylsulfonyl)phenyl)propanal (0.69 g, 3.2 mmol) and trimethylsilanecarbonitrile (0.65 mL, 4.8 mmol) in diethyl ether (1 mL) in a sealed tube is added zinc iodide (1 mg). After stirring for 15 min at room temperature, 7M ammonia in MeOH (2.8 mL, 19 mmol) is slowly added and the mixture is heated to 50° C. and stirred for 18 hours. The mixture is concentrated in vacuo to give the titled compound as a brown oil (0.84 g, >99% yield).
MS (ESI) m/z: 239 (M+H)$^+$.

Step 3: 2-((tert-butoxycarbonyl)amino)-4-(2-(methylsulfonyl)phenyl)butanoic acid A solution of 2-amino-4-(2-(methylsulfonyl)phenyl)butanenitrile (0.77 g, 3.2 mmol) in 12M hydrochloric acid (2.7 mL, 32 mmol) is heated at 100° C. with stirring for 7 hours. The mixture is cooled to room temperature and to the mixture is added 1,4-dioxane (3 mL). Then 10M aqueous NaOH is added to the mixture until the pH became greater than 10. To the solution is added di-tert-butyl dicarbonate (0.85 g, 3.9 mmol) at room temperature and the mixture is stirred at room temperature for 30 min. The mixture is diluted with hexane (40 mL) and water (20 mL) for separation. The aqueous layer is washed with hexane (40 mL) and then acidified by the addition of 2M hydrochloric acid (pH is adjusted to 1). The resulting aqueous suspension is extracted with DCM (30 mL×2). The combined organic layers are dried over $Na_2SO_4$. After filtration, the filtrate is concentrated in vacuo to give the titled compound as brown oil (0.74 g, 64% yield).
$^1$H-NMR (270 MHz, $CDCl_3$) delta 8.02 (1H, d, J=7.9 Hz), 7.58 (1H, dd, J=7.6, 7.6 Hz), 7.44-7.39 (2H, m), 5.45 (1H, d, J=7.2 Hz), 4.42-4.32 (1H, m), 3.21-3.01 (2H, m), 3.10 (3H, s), 2.31-2.08 (2H, m), 1.45 (9H, s). Hydrogen of COOH is not observed. MS (ESI) m/z: 258 (M-Boc+H)$^+$, 356 (M-H)$^-$.

Intermediate 2: 4-(4-bromo-2-chlorophenyl)-2-((tert-butoxycarbonyl)amino)butanoic acid Step 1: 3-(4-bromo-2-chlorophenyl)propanal The title compound is prepared in 86% yield (1.1 g, brown oil) from 4-bromo-2-chloro-1-iodobenzene (1.6 g, 5.0 mmol) in a similar manner to Step 1 of Intermediate 1.

¹H-NMR (270 MHz, CDCl₃) delta 9.80 (1H, s), 7.51 (1H, s), 7.31 (1H, d, J=8.6 Hz), 7.13 (1H, d, J=8.6 Hz), 3.01 (2H, t, J=8.6 Hz), 2.78 (2H, t, J=8.6 Hz).

Step 2:
2-amino-4-(4-bromo-2-chlorophenyl)butanenitrile

The title compound is prepared in >99% yield (1.2 g, brown oil) from 3-(4-bromo-2-chlorophenyl)propanal (1.1 g, 4.3 mmol) in a similar manner to Step 2 of Intermediate 1.

¹H-NMR (270 MHz, CDCl₃) delta 7.53 (1H, d, J=2.0 Hz), 7.34 (1H, dd, J=8.1, 2.0 Hz), 7.13 (1H, d, J=8.1 Hz), 3.66 (1H, t, J=7.3 Hz), 2.93-2.88 (2H, m), 2.04 (2H, dt, J=7.3, 7.3 Hz). Hydrogen of NH₂ is not observed.

MS (ESI) m/z: 273 (M+H)⁺.

Step 3: 4-(4-bromo-2-chlorophenyl)-2-((tert-butoxycarbonyl)amino)butanoic acid

The title compound is prepared in 98% yield (1.7 g, brown oil) from 2-amino-4-(4-bromo-2-chlorophenyl)butanenitrile (1.2 g, 4.4 mmol) in a similar manner to Step 3 of Intermediate 1.

¹H-NMR (270 MHz, CDCl₃) delta 7.50 (1H, d, J=2.0 Hz), 7.32 (1H, dd, J=8.1, 2.0 Hz), 7.11 (1H, d, J=8.1 Hz), 5.11 (1H, d, J=7.9 Hz), 4.44-4.30 (1H, m), 2.90-2.65 (2H, m), 2.21-1.84 (2H, m), 1.46 (9H, s). Hydrogen of COOH is not observed.

MS (ESI) m/z: 336 (M-ᵗBu+H)⁺, 390 (M−H)⁻.

Intermediate 3: 4-(4-bromo-2-fluorophenyl)-2-((tert-butoxycarbonyl)amino)butanoic acid Step 1:
2-amino-4-(4-bromo-2-fluorophenyl)butanenitrile The title compound is prepared in 94% yield (0.89 g, brown oil) from 3-(4-bromo-2-fluorophenyl)propanal (0.85 g, 3.7 mmol) in a similar manner to Step 2 of Intermediate 1.

MS (ESI) m/z: 257 (M+H)⁺.

Step 2: 4-(4-bromo-2-fluorophenyl)-2-((tert-butoxycarbonyl)amino)butanoic acid

The title compound is prepared in 78% yield (1.0 g, brown oil) from 2-amino-4-(4-bromo-2-fluorophenyl)butanenitrile (0.89 g, 3.5 mmol) in a similar manner to Step 3 of Intermediate 1.

MS (ESI) m/z: 320 (M-ᵗBu+H)⁺, 374 (M−H)⁻.

Intermediate 4: 4-(5-bromo-2-fluorophenyl)-2-((tert-butoxycarbonyl)amino)butanoic acid Step 1: 3-(5-bromo-2-fluorophenyl)propanal The title compound is prepared in 68% yield (0.79 g, brown oil) from 4-bromo-1-fluoro-2-iodobenzene (1.5 g, 5.0 mmol) in a similar manner to Step 1 of Intermediate 1.

¹H-NMR (270 MHz, CDCl₃) delta 9.78 (1H, s), 7.34-7.26 (2H, m), 6.94-6.85 (1H, m), 2.91 (2H, t, J=7.2 Hz), 2.78 (2H, t, J=7.2 Hz).

Step 2:
2-amino-4-(5-bromo-2-fluorophenyl)butanenitrile

The title compound is prepared in 99% yield (0.87 g, brown oil) from 3-(5-bromo-2-fluorophenyl)propanal (0.79 g, 3.4 mmol) in a similar manner to Step 2 of Intermediate 1.

¹H-NMR (270 MHz, CDCl₃) delta 7.41-7.25 (2H, m), 6.93 (1H, dd, J=9.0, 9.0 Hz), 3.65 (1H, t, J=7.2 Hz), 2.84 (2H, J=7.6 Hz), 2.08-2.01 (2H, m). Hydrogen of NH₂ is not observed.

MS (ESI) m/z: 257 (M+H)⁺.

Step 3: 4-(5-bromo-2-fluorophenyl)-2-((tert-butoxycarbonyl)amino)butanoic acid

The title compound is prepared in 48% yield (0.61 g, brown oil) from 2-amino-4-(5-bromo-2-fluorophenyl)butanenitrile (0.87 g, 3.4 mmol) in a similar manner to Step 3 of Intermediate 1.

¹H-NMR (270 MHz, CDCl₃) delta 7.36-7.23 (2H, m), 6.89 (1H, dd, J=9.2, 9.2 Hz), 5.14 (1H, d, J=7.3 Hz), 4.33-4.18 (1H, m), 2.78-2.63 (2H, m), 2.25-1.82 (2H, m), 1.47 (9H, s). Hydrogen of COOH is not observed.

MS (ESI) m/z: 275 (M-Boc+H)⁺, 374 (M−H)⁻.

Intermediate 5: 4-(2-bromophenyl)-2-((tert-butoxycarbonyl)amino)butanoic acid

Step 1: 2-amino-4-(2-bromophenyl)butanenitrile

The title compound is prepared in >99% yield (2.0 g, brown oil) from 3-(2-bromophenyl)propanal (1.7 g, 8.0 mmol) in a similar manner to Step 2 of Intermediate 1.

¹H-NMR (270 MHz, CDCl₃) delta 7.55 (1H, d, J=7.9 Hz), 7.30-7.17 (2H, m), 7.15-7.04 (1H, m), 3.68 (1H, t, J=7.2 Hz), 3.01-2.89 (2H, m), 2.17-2.01 (2H, m). Hydrogen of NH₂ is not observed.

MS (ESI) m/z: 239 (M+H)⁺.

Step 2: 4-(2-bromophenyl)-2-((tert-butoxycarbonyl)amino)butanoic acid

The title compound is prepared in 82% yield (2.4 g, brown gum) from 2-amino-4-(2-bromophenyl)butanenitrile (2.0 g, 8.2 mmol) in a similar manner to Step 3 of Intermediate 1.

¹H-NMR (270 MHz, CDCl₃) delta 7.51 (1H, d, J=7.9 Hz), 7.26-7.19 (2H, m), 7.11-7.02 (1H, m), 5.14 (1H, d, J=7.9 Hz), 4.45-4.32 (1H, m), 2.86-2.81 (2H, m), 2.30-1.88 (2H, m), 1.45 (9H, s). Hydrogen of COOH is not observed.

MS (ESI) m/z: 256 (M-Boc+H)+, 356 (M−H)⁻.

Intermediate 6: (R)-2-(2-((tert-butoxycarbonyl)amino)-2-methylpropanamido)-4-phenylbutanoic acid Step 1: (R)-methyl 2-(2-((tert-butoxycarbonyl)amino)-2-methylpropanamido)-4-phenylbutanoate A mixture of (R)-methyl 2-amino-4-phenylbutanoate hydrochloride (0.58 g, 2.5 mmol), 2-((tert-butoxycarbonyl)amino)-2-methylpropanoic acid (0.77 g, 3.8 mmol), 1-ethyl-3-(3-dimethylaminopropyl)carbodiimide hydrochloride (WSC, 0.58 g, 3.0 mmol), 1H-benzo[d][1,2,3]triazol-1-ol (HOBt, 0.21 g, 1.4 mmol), and triethylamine (0.94 mL, 6.8 mmol), and triethylamine (1.1 mL, 7.6 mmol) in DCM (3 mL) is stirred at room temperature for 3 hrs. The mixture is diluted with water (10 mL) and extracted with DCM (20 mL). The organic layer is washed with brine, and dried over $Na_2SO_4$.

After filtration, the filtrate is concentrated in vacuo. The residue is purified by column chromatography (silica gel, eluted with 30-70% EtOAc in hexane) to give the titled compound as a white solid (0.91 g, 95% yield).

MS (ESI) m/z: 379 (M+H)$^+$.

Step 2: (R)-2-(2-((tert-butoxycarbonyl)amino)-2-methylpropanamido)-4-phenylbutanoic acid To a solution of (R)-methyl 2-(2-((tert-butoxycarbonyl) amino)-2-methylpropanamido)-4-phenylbutanoate (0.91 g, 2.4 mmol) in THF (15 mL) is added a solution of LiOH monohydrate (0.30 g, 6.9 mmol) in water (3 mL) at room temperature. The reaction mixture is stirred at room temperature for 3 hours. The volatiles are removed in vacuo. The residue is diluted with water (10 mL) and EtOAc (20 mL). The aqueous layer is washed with EtOAc (20 mL), acidified with 2M hydrochloric acid and then extracted with EtOAc (30 mL). The organic layer is washed with brine, and dried over $Na_2SO_4$. After filtration, the filtrate is concentrated in vacuo to give the titled compound as a white solid (0.92 g, >99% yield).

MS (ESI) m/z: 365 (M+H)$^+$, 363 (M−H)$^−$.

Intermediate 7: 4-(4-bromophenyl)-2-((tert-butoxycarbonyl)amino)butanoic acid

Step 1: 2-amino-4-(4-bromophenyl)butanenitrile

The title compound is prepared in >99% yield (1.9 g, brown oil) from 3-(4-bromophenyl)propanal (1.7 g, 7.7 mmol) in a similar manner to Step 2 of Intermediate 1.

$^1$H-NMR (270 MHz, CDCl$_3$) delta 7.42 (2H, d, J=8.6 Hz), 7.08 (2H, d, J=8.6 Hz), 3.60 (1H, t, J=7.3 Hz), 2.91-2.70 (2H, m), 2.07-1.98 (2H, m). Hydrogen of NH is not observed.

Step 2: 4-(4-bromophenyl)-2-((tert-butoxycarbonyl) amino)butanoic acid

The title compound is prepared in 78% yield (2.2 g, brown gum) from 2-amino-4-(4-bromophenyl)butanenitrile (1.9 g, 7.9 mmol) in a similar manner to Step 3 of Intermediate 1.

$^1$H-NMR (270 MHz, CDCl$_3$) delta 7.40 (2H, d, J=8.9 Hz), 7.06 (2H, d, J=8.9 Hz), 5.05 (1H, br), 4.35-4.09 (1H, m), 2.71-2.61 (2H, m), 2.18-1.84 (2H, m), 1.44 (9H, s). Hydrogen of COOH is not observed.

MS (ESI) m/z: 257 (M−Boc+H)$^+$, 355 (M−H)$^−$.

Intermediate 8: 4-(2-bromo-4-fluorophenyl)-2-((tert-butoxycarbonyl)amino)butanoic acid

Step 1: 3-(2-bromo-4-fluorophenyl)propanal

The title compound is prepared in 79% yield (0.91 g, brown oil) from 2-bromo-4-fluoro-1-iodobenzene (1.5 g, 5.0 mmol) in a similar manner to Step 1 of Intermediate 1.

$^1$H-NMR (270 MHz, CDCl$_3$) delta 9.82 (1H, s), 7.31-7.20 (2H, m), 7.00-6.94 (1H, m), 3.04 (2H, t, J=7.6 Hz), 2.79 (2H, t, J=7.6 Hz).

Step 2: 2-amino-4-(2-bromo-4-fluorophenyl)butanenitrile

The title compound is prepared in >99% yield (1.0 g, brown oil) from 3-(2-bromo-4-fluorophenyl)propanal (0.91 g, 3.9 mmol) in a similar manner to Step 2 of Intermediate 1.

MS (ESI) m/z: 257 (M+H)$^+$.

Step 3: 4-(2-bromo-4-fluorophenyl)-2-((tert-butoxycarbonyl)amino)butanoic acid The title compound is prepared in 74% yield (1.1 g, brown oil) from 2-amino-4-(2-bromo-4-fluorophenyl)butanenitrile (1.0 g, 3.9 mmol) in a similar manner to Step 3 of Intermediate 1.

$^1$H-NMR (270 MHz, CDCl$_3$) delta 7.29-7.18 (2H, m), 6.99-6.92 (1H, m), 5.12 (1H, d, J=7.9 Hz), 4.43-4.14 (1H, m), 2.90-2.74 (2H, m), 2.27-1.83 (2H, m), 1.46 (9H, s). Hydrogen of COOH is not observed.

MS (ESI) m/z: 376 (M+H)$^+$, 374 (M−H)$^−$.

Intermediate 9: 4-(4-bromo-3-fluorophenyl)-2-((tert-butoxycarbonyl)amino)butanoic acid

Step 1: 3-(4-bromo-3-fluorophenyl)propanal

The title compound is prepared in 66% yield (0.76 g, brown oil) from 1-bromo-2-fluoro-4-iodobenzene (1.5 g, 5.0 mmol) in a similar manner to Step 1 of Intermediate 1.

$^1$H-NMR (270 MHz, CDCl$_3$) delta 9.81 (1H, s), 7.47-7.41 (1H, m), 7.02-6.83 (2H, m), 3.00-2.76 (4H, m).

Step 2: 2-amino-4-(4-bromo-3-fluorophenyl)butanenitrile

The title compound is prepared in 97% yield (0.82 g, brown oil) from 3-(4-bromo-3-fluorophenyl)propanal (0.76 g, 3.3 mmol) in a similar manner to Step 2 of Intermediate 1.

$^1$H-NMR (270 MHz, CDCl$_3$) delta 7.51-7.41 (1H, m), 7.01-6.83 (2H, m), 3.61 (1H, t, J=7.3 Hz), 2.97-2.64 (2H, m), 2.17-1.96 (2H, m). Hydrogen of NH$_2$ is not observed.

MS (ESI) m/z: 257 (M+H)$^+$.

Step 3: 4-(4-bromo-3-fluorophenyl)-2-((tert-butoxycarbonyl)amino)butanoic acid The title compound is prepared in 95% yield (1.1 g, brown oil) from 2-amino-4-(4-bromo-3-fluorophenyl)butanenitrile (0.82 g, 3.2 mmol) in a similar manner to Step 3 of Intermediate 1.

$^1$H-NMR (270 MHz, CDCl$_3$) delta 7.47-7.41 (1H, m), 6.99-6.85 (2H, m), 5.08 (1H, d, J=7.3 Hz), 4.41-4.08 (1H, m), 2.82-2.62 (2H, m), 2.28-1.88 (2H, m), 1.45 (9H, s). Hydrogen of COOH is not observed.

MS (ESI) m/z: 320 (M−$^t$Bu+H)$^+$, 374 (M−H)$^−$.

Intermediate 10: 4-(2-bromo-5-fluorophenyl)-2-((tert-butoxycarbonyl)amino)butanoic acid

Step 1: 2-amino-4-(2-bromo-5-fluorophenyl)butanenitrile

The title compound is prepared in >99% yield (1.3 g, orange colored oil) from 3-(2-bromo-5-fluorophenyl)propanal (1.1 g, 4.7 mmol) in a similar manner to Step 2 of Example 1.

¹H-NMR (270 MHz, CDCl₃) delta 7.53-7.48 (1H, m), 7.02-6.97 (1H, m), 6.88-6.81 (1H, m), 3.76-3.63 (1H, m), 2.94 (2H, t, J=7.6 Hz), 2.11-2.02 (2H, m). Hydrogen of NH$_2$ is not observed.

MS (ESI) m/z: 257 (M+H)⁺.

Step 2: 4-(2-bromo-5-fluorophenyl)-2-((tert-butoxycarbonyl)amino)butanoic acid

The title compound is prepared in 69% yield (1.3 g, brown gum) from 2-amino-4-(2-bromo-5-fluorophenyl) butanenitrile (1.3 g, 5.1 mmol) in a similar manner to Step 3 of Intermediate 1.

¹H-NMR (270 MHz, CDCl₃) delta 7.49-7.44 (1H, m), 6.99-6.95 (1H, m), 6.85-6.77 (1H, m), 5.12 (1H, d, J=7.2 Hz), 4.40-4.31 (1H, m), 2.85-2.76 (2H, m), 2.19-1.89 (2H, m), 1.45 (9H, s). Hydrogen of COOH is not observed.

MS (ESI) m/z: 376 (M+H)⁺, 374 (M−H)⁻.

TABLE 4

| Intermediate | Name | Structure |
|---|---|---|
| 1 | 2-((tert-butoxycarbonyl)amino)-\4-(2-(methylsulfonyl)phenyl)butanoic acid | 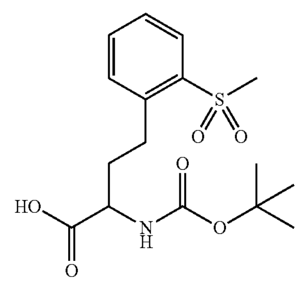 [SMILES: CC(C)(C)OC(=O)NC(CCc1ccccc1S(C)(=O)=O)C(=O)O] |
| 2 | 4-(4-bromo-2-chlorophenyl)-2-((tert-butoxycarbonyl)amino)butanoic acid | 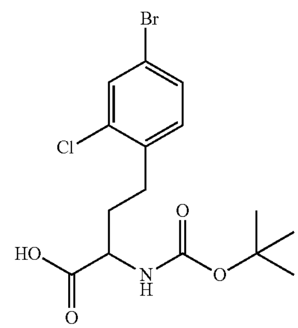 [SMILES: CC(C)(C)OC(=O)NC(CCc1ccc(Br)cc1Cl)C(=O)O] |
| 3 | 4-(4-bromo-2-fluorophenyl)-2-((tert-butoxycarbonyl)amino)butanoic acid | 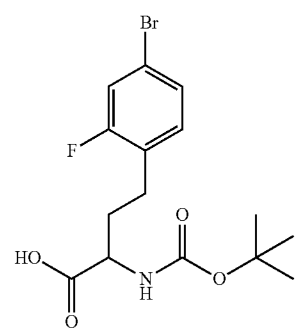 [SMILES: CC(C)(C)OC(=O)NC(CCc1ccc(Br)cc1F)C(=O)O] |
| 4 | 4-(5-bromo-2-fluorophenyl)-2-((tert-butoxycarbonyl)amino)butanoic acid | 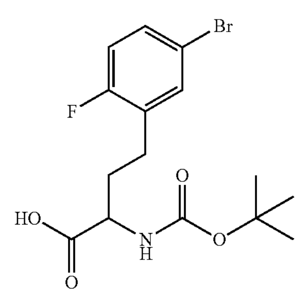 [SMILES: CC(C)(C)OC(=O)NC(CCc1cc(Br)ccc1F)C(=O)O] |

TABLE 4-continued

| Intermediate | Name | Structure |
|---|---|---|
| 5 | 4-(2-bromophenyl)-2-((tert-butoxycarbonyl)amino)butanoic acid | 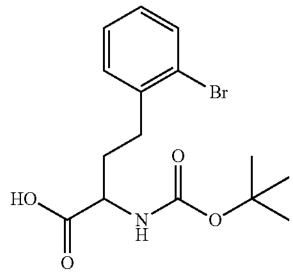 [SMILES: CC(C)(C)OC(=O)NC(CCc1ccccc1Br)C(=O)O] |
| 6 | (R)-2-(2-((tert-butoxycarbonyl)amino)-2-methylpropanamido)-4-phenylbutanoic acid | 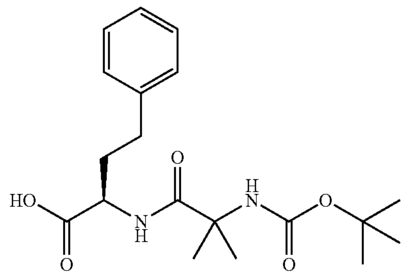 [SMILES: CC(C)(C)OC(=O)NC(C)(C)C(=O)N[C@H](CCc1ccccc1)C(=O)O] |
| 7 | 4-(4-bromophenyl)-2-((tert-butoxycarbonyl)amino)butanoic acid | 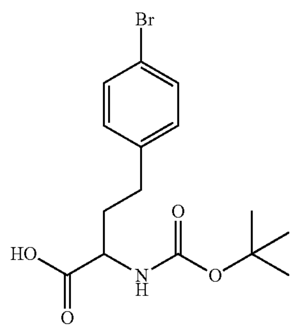 [SMILES: CC(C)(C)OC(=O)NC(CCc1ccc(Br)cc1)C(=O)O] |
| 8 | 4-(2-bromo-4-fluorophenyl)-2-((tert-butoxycarbonyl)amino)butanoic acid | 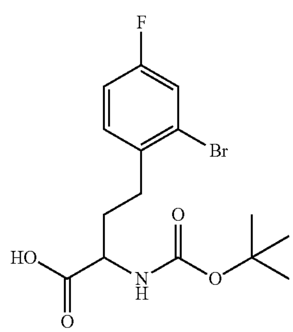 [SMILES: CC(C)(C)OC(=O)NC(CCc1ccc(F)cc1Br)C(=O)O] |
| 9 | 4-(4-bromo-3-fluorophenyl)-2-((tert-butoxycarbonyl)amino)butanoic acid | 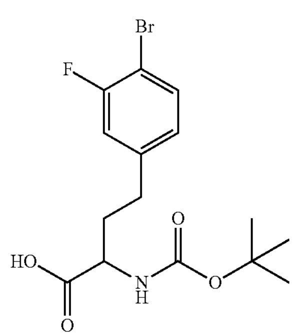 [SMILES: CC(C)(C)OC(=O)NC(CCc1ccc(Br)c(F)c1)C(=O)O] |

TABLE 4-continued

| Intermediate | Name | Structure |
|---|---|---|
| 10 | 4-(2-bromo-5-fluorophenyl)-2-((tert-butoxycarbonyl)amino)butanoic acid | 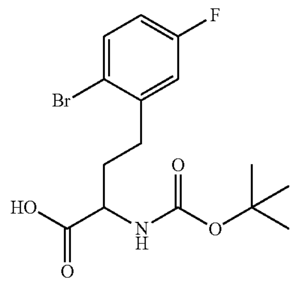 [SMILES: CC(C)(C)OC(=O)NC(CCc1cc(F)ccc1Br)C(=O)O] |

Example 1

2-amino-N—((R)-1-((R)-3a-benzyl-2-methyl-3-oxo-3a,4,6,7-tetrahydro-2H-pyrazolo[4,3-c]pyridin-5(3H)-yl)-4-(2-(methylsulfonyl)phenyl)-1-oxobutan-2-yl)-2-methylpropanamide

Step 1: tert-butyl (1-((R)-3a-benzyl-2-methyl-3-oxo-3a,4,6,7-tetrahydro-2H-pyrazolo[4,3-c]pyridin-5(3H)-yl)-4-(2-(methylsulfonyl)phenyl)-1-oxobutan-2-yl)carbamate A mixture of the (R)-3a-benzyl-2-methyl-4,5,6,7-tetrahydro-2H-pyrazolo[4,3-c]pyridin-3(3aH)-one (2R,3R)-2,3-dihydroxysuccinate (98 mg, 0.25 mmol) and 2-((tert-butoxycarbonyl)amino)-4-(2-(methylsulfonyl)phenyl)butanoic acid (0.11 g, 0.30 mmol, Step 3 of Intermediate 1) in EtOAc (3 mL) is cooled to −5° C. in an ice-bath water. To the mixture is added dropwise triethylamine (0.17 mL, 1.3 mmol) and 2,4,6-tripropyl-1,3,5,2,4,6-trioxatriphosphinane 2,4,6-trioxide (0.29 mL, 0.51 mmol; 1.7 M solution in EtOAc). After stirring for 1 hour at the same temperature, the mixture is quenched with saturated aqueous NaHCO₃ (1 mL) and diluted with EtOAc (1 mL) for separation. The aqueous layer is extracted with EtOAc (1 mL×2) and the combined organic layers are dried over Na₂SO₄. After filtration, the filtrate is concentrated. The residue is purified by column chromatography (silica gel, hexane-EtOAc, gradient) to give the titled compound as oil (64 mg, 39% yield).
MS (ESI) m/z: 583 (M+H)⁺.

Step 2: (3aR)-5-(2-amino-4-(2-(methylsulfonyl)phenyl)butanoyl)-3a-benzyl-2-methyl-4,5,6,7-tetrahydro-2H-pyrazolo[4,3-c]pyridin-3(3aH)-one A mixture of tert-butyl (1-((R)-3a-benzyl-2-methyl-3-oxo-3a,4,6,7-tetrahydro-2H-pyrazolo[4,3-c]pyridin-5(3H)-yl)-4-(2-(methylsulfonyl)phenyl)-1-oxobutan-2-yl)carbamate (65 mg, 0.11 mmol) and trifluoroacetic acid (1 mL) is stirred for 30 min at room temperature. The mixture is concentrated in vacuo. The residue is purified by a strong cation exchange cartridge (Isolute (registered trademark) SCX, 1 g/6 mL, Biotage) to give the titled compound as an oil (54 mg, 78% yield).
MS (ESI) m/z: 483 (M+H)⁺.

Step 3: 2-amino-N—((R)-1-((R)-3a-benzyl-2-methyl-3-oxo-3a,4,6,7-tetrahydro-2H-pyrazolo[4,3-c]pyridin-5(3H)-yl)-4-(2-(methylsulfonyl)phenyl)-1-oxobutan-2-yl)-2-methylpropanamide A mixture of (3aR)-5-(2-amino-4-(2-(methylsulfonyl)phenyl)butanoyl)-3a-benzyl-2-methyl-4,5,6,7-tetrahydro-2H-pyrazolo[4,3-c]pyridin-3(3aH)-one (42 mg, 0.087 mmol) and 2-((tert-butoxycarbonyl)amino)-2-methylpropanoic acid (27 mg, 0.13 mmol) in EtOAc (2 mL) is cooled to 0° C. To the mixture is added dropwise triethylamine (0.061 mL, 0.43 mmol) and 2,4,6-tripropyl-1,3,5,2,4,6-trioxatriphosphinane 2,4,6-trioxide (0.13 mL, 0.22 mmol; 1.7 M solution in EtOAc). After stirring for 1 hour at the same temperature, the mixture is concentrated in vacuo. Then, trifluoroacetic acid (2 mL) is added to the residue and the mixture is stirred for 30 min at room temperature. The mixture is concentrated in vacuo. The residue is purified by a strong cation exchange cartridge (Isolute (registered trademark) SCX, 1 g/6 mL, Biotage) to give a mixture of diastereomers. The mixture is further purified by preparative LC-MS to give 5 mg (9% yield) of the title compound. The desired diastereomer is collected as a more polar one under the preparative LC-MS condition. Condition for the preparative LC-MS and quality check (QC) method are shown in Table 1 and Table 2.

Example 2

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-4-phenylbutan-2-yl)-2-methylpropanamide

Step 1: tert-butyl ((R)-1-((R)-3a-benzyl-2-methyl-3-oxo-3a,4,6,7-tetrahydro-2H-pyrazolo[4,3-c]pyridin5(3H)-yl)-1-oxo-4-phenylbutan-2-yl)carbamate The title compound is prepared in 70% yield (0.63 g, white solid) from (R)-3a-benzyl-2-methyl-4,5,6,7-tetrahydro-2H-pyrazolo[4,3-c]pyridin-3(3aH)-one (2R,3R)-2,3-dihydroxysuccinate (0.71 g, 1.8 mmol) and (R)-2-((tert-butoxycarbonyl)amino)-4-phenylbutanoic acid (0.56 g, 2.0 mmol) in a similar manner to Step 1 of Example 1.
MS (ESI) m/z: 505 (M+H)⁺.

Step 2: (R)-5-((R)-2-amino-4-phenylbutanoyl)-3a-benzyl-2-methyl-4,5,6,7-tetrahydro-2H-pyrazolo[4,3-c]pyridin-3(3aH)-one The title compound is prepared in 90% yield (0.44 g, solid) from tert-butyl ((R)-1-((R)-3a-benzyl-2-methyl-3-oxo-3a,4,6,7-tetrahydro-2H-pyrazolo[4,3-c]pyridin-5(3H)-yl)-1-oxo-4-phenylbutan-2-yl)carbamate (0.61 g, 1.2 mmol) in a similar manner to Step 2 of Example 1.
MS (ESI) m/z: 405 (M+H)⁺.

Step 3: tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-4-phenylbutan-2-yl)amino)-2-methyl-1-oxopropan-2-yl)carbamate To a mixture of (R)-5-((R)-2-amino-4-phenylbutanoyl)-3a-benzyl-2-methyl-4,5,6,7-tetrahydro-2H-pyrazolo[4,3-c]pyridin-3(3aH)-one (0.44 g, 1.1 mmol) and 2-((tert-butoxycarbonyl)amino)-2-methylpropanoic acid (0.27 g, 1.3 mmol) in EtOAc (10 mL) is added dropwise triethylamine (0.46 mL, 3.3 mmol) and 2,4,6-tripropyl-1,3,5,2,4,6-trioxatriphosphinane 2,4,6-trioxide (1.3 mL, 2.2 mmol; 1.7 M solution in EtOAc). The mixture is stirred at room temperature overnight. The mixture is concentrated in vacuo. The residue is purified by column chromatography (silica gel, eluted with 30-100% EtOAc in hexane) to give the titled compound (0.60 g, 93%) as a solid MS (ESI) m/z: 590 (M+H)$^+$, 588 (M−H)$^−$.

Step 4: 2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-4-phenylbutan-2-yl)-2-methylpropanamide tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-4-phenylbutan-2-yl)amino)-2-methyl-1-oxopropan-2-yl)carbamate (72 mg, 0.12 mmol) is dissolved in 4N hydrogen chloride in dioxane (2 mL) at 0° C., and the mixture is stirred for 1 hour at the same temperature. The mixture is concentrated in vacuo. The residue is purified by a strong cation exchange cartridge (Isolute (registered trademark) SCX, 1 g/6 mL, Biotage), and then further purified by preparative LC-MS to give 5 mg (8% yield) of the title compound.

Example 3

2-amino-N—((R)-1-((R)-3a-benzyl-2-methyl-3-oxo-3a,4,6,7-tetrahydro-2H-pyrazolo[4,3-c]pyridin-5(3H)-yl)-4-(2-chloro-4-(hydroxymethyl)phenyl)-1-oxobutan-2-yl)-2-methylpropanamide

Step 1: tert-butyl (1-((R)-3a-benzyl-2-methyl-3-oxo-3a,4,6,7-tetrahydro-2H-pyrazolo[4,3-c]pyridin-5(3H)-yl)-4-(4-bromo-2-chlorophenyl)-1-oxobutan-2-yl)carbamate The title compound is prepared in 66% yield (0.20 g, oil) from (R)-3a-benzyl-2-methyl-4,5,6,7-tetrahydro-2H-pyrazolo[4,3-c]pyridin-3(3aH)-one (2R,3R)-2,3-dihydroxysuccinate (0.20 g, 0.50 mmol) and 4-(4-bromo-2-chlorophenyl)-2-((tert-butoxycarbonyl)amino)butanoic acid (0.24 g, 0.60 mmol, Step 3 of Intermediate 2) in a similar manner to Step 1 of Example 1.

MS (ESI) m/z: 617 (M+H)$^+$.

Step 2: (3aR)-5-(2-amino-4-(4-bromo-2-chlorophenyl)butanoyl)-3a-benzyl-2-methyl-4,5,6,7-tetrahydro-2H-pyrazolo[4,3-c]pyridin-3(3aH)-one The title compound is prepared in 74% yield (0.13 g, oil) from tert-butyl (1-((R)-3a-benzyl-2-methyl-3-oxo-3a,4,6,7-tetrahydro-2H-pyrazolo[4,3-c]pyridin-5(3H)-yl)-4-(4-bromo-2-chlorophenyl)-1-oxobutan-2-yl)carbamate (0.20 g, 0.33 mmol) in a similar manner to Step 2 of Example 1.

MS (ESI) m/z: 517 (M+H)$^+$.

Step 3: tert-butyl (1-((1-((R)-3a-benzyl-2-methyl-3-oxo-3a,4,6,7-tetrahydro-2H-pyrazolo[4,3-c]pyridin-5(3H)-yl)-4-(4-bromo-2-chlorophenyl)-1-oxobutan-2-yl)amino)-2-methyl-1-oxopropan-2-yl)carbamate The title compound is prepared in 79% yield (0.14 g, oil) from (3aR)-5-(2-amino-4-(4-bromo-2-chlorophenyl)butanoyl)-3a-benzyl-2-methyl-4,5,6,7-tetrahydro-2H-pyrazolo[4,3-c]pyridin-3(3aH)-one (0.13 g, 0.25 mmol) in a similar manner to Step 3 of Example 2.

MS (ESI) m/z: 704 (M+H)$^+$, 702 (M−H)$^−$.

Step 4: ethyl 4-(4-((R)-3a-benzyl-2-methyl-3-oxo-3a,4,6,7-tetrahydro-2H-pyrazolo[4,3-c]pyridin-5(3H)-yl)-3-(2-((tert-butoxycarbonyl)amino)-2-methylpropanamido)-4-oxobutyl)-3-chlorobenzoate A mixture of tert-butyl (1-((1-((R)-3a-benzyl-2-methyl-3-oxo-3a,4,6,7-tetrahydro-2H-pyrazolo[4,3-c]pyridin-5(3H)-yl)-4-(4-bromo-2-chlorophenyl)-1-oxobutan-2-yl)amino)-2-methyl-1-oxopropan-2-yl)carbamate (0.14 g, 0.19 mmol), palladium (II) acetate (4.3 mg, 0.019 mmol), 1,3-bis(diphenylphosphino)propane (8.0 mg, 0.019 mmol), triethylamine (0.054 mL, 0.39 mmol) in DMF (5 mL), and EtOH (2 mL) is heated at 100° C. under carbon monoxide atmosphere overnight. The mixture is cooled to room temperature and filtered through a pad of Celite (registered trademark). The filtrate is diluted with EtOAc (10 mL) and the solution is washed with water (10 mL×2) and brine (5 mL). The organic layer is dried over Na$_2$SO$_4$. After filteration, the filtrate is concentrated in vacuo. The residue is purified by column chromatography (silica gel, eluted with 20-100% EtOAc in hexane) to give the titled compound as an oil (0.16 g, >99% yield).

MS (ESI) m/z: 697 (M+H)$^+$, 695 (M−H)$^−$.

Step 5: 4-(4-((R)-3a-benzyl-2-methyl-3-oxo-3a,4,6,7-tetrahydro-2H-pyrazolo[4,3-c]pyridin-5(3H)-yl)-3-(2-((tert-butoxycarbonyl)amino)-2-methylpropanamido)-4-oxobutyl)-3-chlorobenzoic acid To a solution of ethyl 4-(4-((R)-3a-benzyl-2-methyl-3-oxo-3a,4,6,7-tetrahydro-2H-pyrazolo[4,3-c]pyridin-5(3H)-yl)-3-(2-((tert-butoxycarbonyl)amino)-2-methylpropanamido)-4-oxobutyl)-3-chlorobenzoate (0.16 g, 0.23 mmol) in THF (1 mL) is added LiOH monohydrate (14 mg, 0.34 mmol), and then water (0.2 mL) and MeOH (0.2 mL) are added. The mixture is stirred at room temperature overnight. The mixture is diluted with saturated aqueous NaHCO$_3$ (5 mL) and hexane for separation. The aqueous layer is acidified by the addition of 2N hydrochloric acid and the resulting suspension is extracted with dichloromethane (10 mL×2). The combined organic layers are washed with brine, and dried over Na$_2$SO$_4$ After filtration, the filtrate is concentrated to give the titled compound as a white solid (0.12 g, 78%).

MS (ESI) m/z: 668 (M+H)$^+$, 666 (M−H)$^−$.

Step 6: tert-butyl (1-((1-((R)-3a-benzyl-2-methyl-3-oxo-3a,4,6,7-tetrahydro-2H-pyrazolo[4,3-c]pyridin-5(3H)-yl)-4-(2-chloro-4-(hydroxymethyl)phenyl)-1-oxobutan-2-yl)amino)-2-methyl-1-oxopropan-2-yl)carbamate To a solution of 4-(4-((R)-3a-benzyl-2-methyl-3-oxo-3a,4,6,7-tetrahydro-2H-pyrazolo[4,3-c]pyridin-5(3H)-yl)-3-(2-

((tert-butoxycarbonyl)amino)-2-methylpropanamido)-4-oxobutyl)-3-chlorobenzoic acid (0.12 g, 0.18 mmol) in THF (1 mL) is added carbonyldiimidazole (CDI, 43 mg, 0.27 mmol) at room temperature, and the mixture is stirred at room temperature overnight. To the mixture is added a solution of NaBH$_4$ in water (0.3 mL) at 0° C. After stirring for 10 min, the reaction is quenched with 2N hydrochloric acid at 0° C. (5 drops) and the mixture is basified by the addition of saturated aqueous NaHCO$_3$. The mixture is extracted with EtOAc (2 mL×3) and the combined organic layers are dried over Na$_2$SO$_4$. After filtration, the filtrate is concentrated in vacuo. The residue is purified by column chromatography (silica gel, eluted with 50-100% EtOAc in hexane) to give the titled compound as a colorless oil (34 mg, 29% yield).

MS (ESI) m/z: 654 (M+H)$^+$, 652 (M−H)$^-$.

Step 7: 2-amino-N—((R)-1-((R)-3a-benzyl-2-methyl-3-oxo-3a,4,6,7-tetrahydro-2H-pyrazolo[4,3-c]pyridin-5(3H)-yl)-4-(2-chloro-4-(hydroxymethyl)phenyl)-1-oxobutan-2-yl)-2-methylpropanamide A mixture of tert-butyl (1-((1-((R)-3a-benzyl-2-methyl-3-oxo-3a,4,6,7-tetrahydro-2H-pyrazolo[4,3-c]pyridin-5(3H)-yl)-4-(2-chloro-4-(hydroxymethyl)phenyl)-1-oxobutan-2-yl)amino)-2-methyl-1-oxopropan-2-yl)carbamate (33 mg, 0.050 mmol) and trifluoroacetic acid (2 mL) is stirred for 30 min at room temperature. The mixture is concentrated in vacuo. The residue is purified by a strong cation exchange cartridge (Isolute (registered trademark) SCX, 1 g/6 mL, Biotage), and then further purified by preparative LC-MS to give 9 mg (32% yield) of the title compound. The desired diastereomer is collected as a more polar one under the preparative LC-MS condition.

Example 4

2-amino-N—((R)-1-((R)-3a-benzyl-2-methyl-3-oxo-3a,4,6,7-tetrahydro-2H-pyrazolo[4,3-c]pyridin-5(3H)-yl)-4-(2-fluoro-4-(hydroxymethyl)phenyl)-1-oxobutan-2-yl)-2-methylpropanamide Step 1: tert-butyl (1-((R)-3a-benzyl-2-methyl-3-oxo-3a,4,6,7-tetrahydro-2H-pyrazolo[4,3-c]pyridin-5(3H)-yl)-4-(4-bromo-2-fluorophenyl)-1-oxobutan-2-yl)carbamate The title compound is prepared in 63% yield (0.19 g, oil) from (R)-3a-benzyl-2-methyl-4,5,6,7-tetrahydro-2H-pyrazolo[4,3-c]pyridin-3(3aH)-one (2R,3R)-2,3-dihydroxysuccinate (0.20 g, 0.50 mmol) and 4-(4-bromo-2-fluorophenyl)-2-((tert-butoxycarbonyl)amino)butanoic acid (0.23 g, 0.60 mmol, Step 2 of Intermediate 3) in a similar manner to Step 1 of Example 1.

MS (ESI) m/z: 601 (M+H)$^+$.

Step 2: (3aR)-5-(2-amino-4-(4-bromo-2-fluorophenyl)butanoyl)-3a-benzyl-2-methyl-4,5,6,7-tetrahydro-2H-pyrazolo[4,3-c]pyridin-3(3aH)-one The title compound is prepared in 84% yield (0.13 g, oil) from tert-butyl (1-((R)-3a-benzyl-2-methyl-3-oxo-3a,4,6,7-tetrahydro-2H-pyrazolo[4,3-c]pyridin-5(3H)-yl)-4-(4-bromo-2-fluorophenyl)-1-oxobutan-2-yl)carbamate (0.19 g, 0.32 mmol) in a similar manner to Step 2 of Example 1.

MS (ESI) m/z: 501 (M+H)$^+$.

Step 3: tert-butyl (1-((1-((R)-3a-benzyl-2-methyl-3-oxo-3a,4,6,7-tetrahydro-2H-pyrazolo[4,3-c]pyridin-5(3H)-yl)-4-(4-bromo-2-fluorophenyl)-1-oxobutan-2-yl)amino)-2-methyl-1-oxopropan-2-yl)carbamate The title compound is prepared in 99% yield (0.18 g, colorless oil) from (3aR)-5-(2-amino-4-(4-bromo-2-fluorophenyl)butanoyl)-3a-benzyl-2-methyl-4,5,6,7-tetrahydro-2H-pyrazolo[4,3-c]pyridin-3(3aH)-one (0.13 g, 0.27 mmol) and 2-((tert-butoxycarbonyl)amino)-2-methylpropanoic acid (81 mg, 0.40 mmol) in a similar manner to Step 3 of Example 2.

MS (ESI) m/z: 686 (M+H)$^+$, 684 (M−H)$^-$.

Step 4: ethyl 4-(4-((R)-3a-benzyl-2-methyl-3-oxo-3a,4,6,7-tetrahydro-2H-pyrazolo[4,3-c]pyridin-5(3H)-yl)-3-(2-((tert-butoxycarbonyl)amino)-2-methylpropanamido)-4-oxobutyl)-3-fluorobenzoate The title compound is prepared in >99% yield (0.18 g, oil) from tert-butyl (1-((1-((R)-3a-benzyl-2-methyl-3-oxo-3a,4,6,7-tetrahydro-2H-pyrazolo[4,3-c]pyridin-5(3H)-yl)-4-(4-bromo-2-fluorophenyl)-1-oxobutan-2-yl)amino)-2-methyl-1-oxopropan-2-yl)carbamate (0.18 g, 0.26 mmol) in a similar manner to Step 4 of Example 3.

MS (ESI) m/z: 680 (M+H)$^+$, 678 (M−H)$^-$.

Step 5: 4-(4-((R)-3a-benzyl-2-methyl-3-oxo-3a,4,6,7-tetrahydro-2H-pyrazolo[4,3-c]pyridin-5(3H)-yl)-3-(2-((tert-butoxycarbonyl)amino)-2-methylpropanamido)-4-oxobutyl)-3-fluorobenzoic acid The title compound is prepared in 70% yield (0.18 g, white solid) from ethyl 4-(4-((R)-3a-benzyl-2-methyl-3-oxo-3a,4,6,7-tetrahydro-2H-pyrazolo[4,3-c]pyridin-5(3H)-yl)-3-(2-((tert-butoxycarbonyl)amino)-2-methylpropanamido)-4-oxobutyl)-3-fluorobenzoate (0.18 g, 0.27 mmol) in a similar manner to Step 5 of Example 3.

MS (ESI) m/z: 652 (M+H)$^+$, 650 (M−H)$^-$.

Step 6: tert-butyl (1-((1-((R)-3a-benzyl-2-methyl-3-oxo-3a,4,6,7-tetrahydro-2H-pyrazolo[4,3-c]pyridin-5(3H)-yl)-4-(2-fluoro-4-(hydroxymethyl)phenyl)-1-oxobutan-2-yl)amino)-2-methyl-1-oxopropan-2-yl)carbamate The title compound is prepared in 31% yield (40 mg, colorless oil) from 4-(4-((R)-3a-benzyl-2-methyl-3-oxo-3a,4,6,7-tetrahydro-2H-pyrazolo[4,3-c]pyridin-5(3H)-yl)-3-(2-((tert-butoxycarbonyl)amino)-2-methylpropanamido)-4-oxobutyl)-3-fluorobenzoic acid (0.12 g, 0.19 mmol) in a similar manner to Step 6 of Example 3.

MS (ESI) m/z: 638 (M+H)$^+$, 636 (M−H)$^-$.

Step 7: 2-amino-N—((R)-1-((R)-3a-benzyl-2-methyl-3-oxo-3a,4,6,7-tetrahydro-2H-pyrazolo[4,3-c]pyridin-5(3H)-yl)-4-(2-fluoro-4-(hydroxymethyl)phenyl)-1-oxobutan-2-yl)-2-methylpropanamide The title compound is prepared in 19% yield (6.0 mg) from tert-butyl (1-((1-((R)-3a-benzyl-2-methyl-3-oxo-3a,4,6,7-tetrahydro-2H-pyrazolo[4,3-c]pyridin-5(3H)-yl)-4-(2-fluoro-4-(hydroxymethyl)phenyl)-1-oxobutan-2-yl)amino)-

2-methyl-1-oxopropan-2-yl)carbamate (38 mg, 0.059 mmol) in a similar manner to Step 7 of Example 3.

Example 5

2-amino-N—((R)-1-((R)-3a-benzyl-2-methyl-3-oxo-3a,4,6,7-tetrahydro-2H-pyrazolo[4,3-c]pyridin-5 (3H)-yl)-4-(2-fluoro-5-(hydroxymethyl)phenyl)-1-oxobutan-2-yl)-2-methylpropanamide Step 1: tert-butyl (1-((R)-3a-benzyl-2-methyl-3-oxo-3a,4,6,7-tetrahydro-2H-pyrazolo[4,3-c]pyridin-5(3H)-yl)-4-(5-bromo-2-fluorophenyl)-1-oxobutan-2-yl)carbamate The title compound is prepared in 50% yield (0.22 g, oil) from (R)-3a-benzyl-2-methyl-4,5,6,7-tetrahydro-2H-pyrazolo[4,3-c]pyridin-3(3aH)-one (2R,3R)-2,3-dihydroxysuccinate (0.30 g, 0.75 mmol) and 4-(4-bromo-2-fluorophenyl)-2-((tert-butoxycarbonyl)amino)butanoic acid (0.28 g, 0.75 mmol, Step 3 of Intermediate 4) in a similar manner to Step 1 of Example 1.
MS (ESI) m/z: 601 (M+H)$^+$.

Step 2: (3aR)-5-(2-amino-4-(5-bromo-2-fluorophenyl)butanoyl)-3a-benzyl-2-methyl-4,5,6,7-tetrahydro-2H-pyrazolo[4,3-c]pyridin-3(3aH)-one The title compound is prepared in 98% yield (0.18 g, oil) from tert-butyl (1-((R)-3a-benzyl-2-methyl-3-oxo-3a,4,6,7-tetrahydro-2H-pyrazolo[4,3-c]pyridin-5(3H)-yl)-4-(5-bromo-2-fluorophenyl)-1-oxobutan-2-yl)carbamate (0.22 g, 0.37 mmol) in a similar manner to Step 2 of Example 1.
MS (ESI) m/z: 501 (M+H)$^+$.

Step 3: tert-butyl (1-((1-((R)-3a-benzyl-2-methyl-3-oxo-3a,4,6,7-tetrahydro-2H-pyrazolo[4,3-c]pyridin-5(3H)-yl)-4-(5-bromo-2-fluorophenyl)-1-oxobutan-2-yl)amino)-2-methyl-1-oxopropan-2-yl)carbamate The title compound is prepared in 74% yield (0.19 g, colorless oil) from (3aR)-5-(2-amino-4-(5-bromo-2-fluorophenyl)butanoyl)-3a-benzyl-2-methyl-4,5,6,7-tetrahydro-2H-pyrazolo[4,3-c]pyridin-3(3aH)-one (0.18 g, 0.37 mmol) and 2-((tert-butoxycarbonyl)amino)-2-methylpropanoic acid (110 mg, 0.55 mmol) in a similar manner to Step 3 of Example 2.
MS (ESI) m/z: 686 (M+H)$^+$, 684 (M–H)$^-$.

Step 4: ethyl 3-(4-((R)-3a-benzyl-2-methyl-3-oxo-3a,4,6,7-tetrahydro-2H-pyrazolo[4,3-c]pyridin-5(3H)-yl)-3-(2-((tert-butoxycarbonyl)amino)-2-methylpropanamido)-4-oxobutyl)-4-fluorobenzoate The title compound is prepared in 97% yield (0.18 g, oil) from tert-butyl (1-((1-((R)-3a-benzyl-2-methyl-3-oxo-3a,4,6,7-tetrahydro-2H-pyrazolo[4,3-c]pyridin-5(3H)-yl)-4-(5-bromo-2-fluorophenyl)-1-oxobutan-2-yl)amino)-2-methyl-1-oxopropan-2-yl)carbamate (0.18 g, 0.26 mmol) in a similar manner to Step 4 of Example 3.
MS (ESI) m/z: 697 (M+NH$_4$+H)$^+$, 678 (M–H)$^-$.

Step 5: 3-(4-((R)-3a-benzyl-2-methyl-3-oxo-3a,4,6,7-tetrahydro-2H-pyrazolo[4,3-c]pyridin-5(3H)-yl)-3-(2-((tert-butoxycarbonyl)amino)-2-methylpropanamido)-4-oxobutyl)-4-fluorobenzoic acid The title compound is prepared in 80% yield (0.14 g, brown oil) from ethyl 3-(4-((R)-3a-benzyl-2-methyl-3-oxo-3a,4,6,7-tetrahydro-2H-pyrazolo[4,3-c]pyridin-5(3H)-yl)-3-(2-((tert-butoxycarbonyl)amino)-2-methylpropanamido)-4-oxobutyl)-4-fluorobenzoate (0.18 g, 0.26 mmol) in a similar manner to Step 5 of Example 3.
MS (ESI) m/z: 652 (M+H)$^+$, 650 (M–H)$^-$.

Step 6: tert-butyl (1-((1-((R)-3a-benzyl-2-methyl-3-oxo-3a,4,6,7-tetrahydro-2H-pyrazolo[4,3-c]pyridin-5(3H)-yl)-4-(2-fluoro-5-(hydroxymethyl)phenyl)-1-oxobutan-2-yl)amino)-2-methyl-1-oxopropan-2-yl)carbamate The title compound is prepared in 43% yield (57 mg, colorless oil) from 3-(4-((R)-3a-benzyl-2-methyl-3-oxo-3a,4,6,7-tetrahydro-2H-pyrazolo[4,3-c]pyridin-5(3H)-yl)-3-(2-((tert-butoxycarbonyl)amino)-2-methylpropanamido)-4-oxobutyl)-4-fluorobenzoic acid (0.14 g, 0.21 mmol) in a similar manner to Step 6 of Example 3.
MS (ESI) m/z: 638 (M+H)$^+$, 636 (M–H)$^-$.

Step 7: 2-amino-N—((R)-1-((R)-3a-benzyl-2-methyl-3-oxo-3a,4,6,7-tetrahydro-2H-pyrazolo[4,3-c]pyridin-5(3H)-yl)-4-(2-fluoro-5-(hydroxymethyl)phenyl)-1-oxobutan-2-yl)-2-methylpropanamide The title compound is prepared in 15% yield (8.0 mg) from tert-butyl (1-((1-((R)-3a-benzyl-2-methyl-3-oxo-3a,4,6,7-tetrahydro-2H-pyrazolo[4,3-c]pyridin-5(3H)-yl)-4-(2-fluoro-5-(hydroxymethyl)phenyl)-1-oxobutan-2-yl)amino)-2-methyl-1-oxopropan-2-yl)carbamate (57 mg, 0.090 mmol) in a similar manner to Step 7 of Example 3.

Example 6

2-amino-N—((R)-1-((R)-3a-benzyl-2-methyl-3-oxo-3a,4,6,7-tetrahydro-2H-pyrazolo[4,3-c]pyridin-5(3H)-yl)-4-(2-(hydroxymethyl)phenyl)-1-oxobutan-2-yl)-2-methylpropanamide Step 1: tert-butyl (1-((R)-3a-benzyl-2-methyl-3-oxo-3a,4,6,7-tetrahydro-2H-pyrazolo[4,3-c]pyridin-5(3H)-yl)-4-(2-bromophenyl)-1-oxobutan-2-yl)carbamate The title compound is prepared in 62% yield (0.27 g, beige solid) from (R)-3a-benzyl-2-methyl-4,5,6,7-tetrahydro-2H-pyrazolo[4,3-c]pyridin-3(3aH)-one (2R,3R)-2,3-dihydroxysuccinate (0.30 g, 0.75 mmol) and 4-(2-bromophenyl)-2-((tert-butoxycarbonyl)amino)butanoic acid (0.30 g, 0.83 mmol, Step 2 of Intermediate 5) in a similar manner to Step 1 of Example 1.
MS (ESI) m/z: 583 (M+H)$^+$.

Step 2: (3aR)-5-(2-amino-4-(2-bromophenyl)butanoyl)-3a-benzyl-2-methyl-4,5,6,7-tetrahydro-2H-pyrazolo[4,3-c]pyridin-3(3aH)-one The title compound is prepared in 67% yield (0.15 g, oil) from tert-butyl (1-((R)-3a-benzyl-2-methyl-3-oxo-3a,4,6,7-tetrahydro-2H-pyrazolo[4,3-c]pyridin-5(3H)-yl)-4-(2-bromophenyl)-1-oxobutan-2-yl)carbamate (0.27 g, 0.46 mmol) in a similar manner to Step 2 of Example 1.
MS (ESI) m/z: 483 (M+H)$^+$.

Step 3: tert-butyl (1-((1-((R)-3a-benzyl-2-methyl-3-oxo-3a,4,6,7-tetrahydro-2H-pyrazolo[4,3-c]pyridin-5(3H)-yl)-4-(2-bromophenyl)-1-oxobutan-2-yl)amino)-2-methyl-1-oxopropan-2-yl)carbamate The title compound is prepared in 58% yield (0.12 g, colorless oil) from (3aR)-5-(2-amino-4-(2-bromophenyl)butanoyl)-3a-benzyl-2-methyl-4,5,6,7-tetrahydro-2H-pyrazolo[4,3-c]pyridin-3(3aH)-one (0.15 g, 0.31 mmol) and 2-((tert-butoxycarbonyl)amino)-2-methylpropanoic acid (95 mg, 0.47 mmol) in a similar manner to Step 3 of Example 2.

MS (ESI) m/z: 668 (M+H)$^+$, 666 (M–H)$^-$.

Step 4: ethyl 2-(4-((R)-3a-benzyl-2-methyl-3-oxo-3a,4,6,7-tetrahydro-2H-pyrazolo[4,3-c]pyridin-5(3H)-yl)-3-(2-((tert-butoxycarbonyl)amino)-2-methylpropanamido)-4-oxobutyl)benzoate The title compound is prepared in >99% yield (0.13 g, oil) from tert-butyl (1-((1-((R)-3a-benzyl-2-methyl-3-oxo-3a,4,6,7-tetrahydro-2H-pyrazolo[4,3-c]pyridin-5(3H)-yl)-4-(2-bromophenyl)-1-oxobutan-2-yl)amino)-2-methyl-1-oxopropan-2-yl)carbamate (0.12 g, 0.18 mmol) in a similar manner to Step 4 of Example 3.

MS (ESI) m/z: 662 (M+H)$^+$, 660 (M–H)$^-$.

Step 5: 2-(4-((R)-3a-benzyl-2-methyl-3-oxo-3a,4,6,7-tetrahydro-2H-pyrazolo[4,3-c]pyridin-5(3H)-yl)-3-(2-((tert-butoxycarbonyl)amino)-2-methylpropanamido)-4-oxobutyl)benzoic acid The title compound is prepared in >99% yield (0.13 g, oil) from ethyl 2-(4-((R)-3a-benzyl-2-methyl-3-oxo-3a,4,6,7-tetrahydro-2H-pyrazolo[4,3-c]pyridin-5(3H)-yl)-3-(2-((tert-butoxycarbonyl)amino)-2-methylpropanamido)-4-oxobutyl)benzoate (0.13 g, 0.20 mmol) in a similar manner to Step 5 of Example 3.

MS (ESI) m/z: 634 (M+H)$^+$, 632 (M–H)$^-$.

Step 6: tert-butyl (1-((1-((R)-3a-benzyl-2-methyl-3-oxo-3a,4,6,7-tetrahydro-2H-pyrazolo[4,3-c]pyridin-5(3H)-yl)-4-(2-(hydroxymethyl)phenyl)-1-oxobutan-2-yl)amino)-2-methyl-1-oxopropan-2-yl)carbamate The title compound is prepared in 41% yield (51 mg, colorless oil) from 2-(4-((R)-3a-benzyl-2-methyl-3-oxo-3a,4,6,7-tetrahydro-2H-pyrazolo[4,3-c]pyridin-5(3H)-yl)-3-(2-((tert-butoxycarbonyl)amino)-2-methylpropanamido)-4-oxobutyl)benzoic acid (0.13 g, 0.20 mmol) in a similar manner to Step 6 of Example 3.

MS (ESI) m/z: 620 (M+H)$^+$, 618 (M–H)$^-$.

Step 7: 2-amino-N—((R)-1-((R)-3a-benzyl-2-methyl-3-oxo-3a,4,6,7-tetrahydro-2H-pyrazolo[4,3-c]pyridin-5(3H)-yl)-4-(2-(hydroxymethyl)phenyl)-1-oxobutan-2-yl)-2-methylpropanamide The title compound is prepared in 37% yield (16 mg) from tert-butyl (1-((1-((R)-3a-benzyl-2-methyl-3-oxo-3a,4,6,7-tetrahydro-2H-pyrazolo[4,3-c]pyridin-5(3H)-yl)-4-(2-(hydroxymethyl)phenyl)-1-oxobutan-2-yl)amino)-2-methyl-1-oxopropan-2-yl)carbamate (0.13 g, 0.20 mmol) in a similar manner to Step 7 of Example 3.

Example 7

2-amino-N—((R)-1-((R)-3a-benzyl-2-methyl-3-oxo-3a,4,6,7-tetrahydro-2H-pyrazolo[4,3-c]pyridin-5(3H)-yl)-5-(3-(hydroxymethyl)phenyl)-1-oxopentan-2-yl)-2-methylpropanamide

Step 1: tert-butyl ((R)-1-((R)-3a-benzyl-2-methyl-3-oxo-3a,4,6,7-tetrahydro-2H-pyrazolo[4,3-c]pyridin-5(3H)-yl)-1-oxopent-4-yn-2-yl)carbamate The title compound is prepared in 48% yield (0.65 g, white solid) from (R)-3a-benzyl-2-methyl-4,5,6,7-tetrahydro-2H-pyrazolo[4,3-c]pyridin-3(3aH)-one (2R,3R)-2,3-dihydroxysuccinate (1.2 g, 3.1 mmol) and (R)-2-((tert-butoxycarbonyl)amino)pent-4-ynoic acid (0.72 g, 3.4 mmol) in a similar manner to Step 1 of Example 1.

MS (ESI) m/z: 439 (M+H)$^+$, 437 (M–H)$^-$.

Step 2: (R)-5-((R)-2-aminopent-4-ynoyl)-3a-benzyl-2-methyl-4,5,6,7-tetrahydro-2H-pyrazolo[4,3-c]pyridin-3(3aH)-one A mixture of tert-butyl ((R)-1-((R)-3a-benzyl-2-methyl-3-oxo-3a,4,6,7-tetrahydro-2H-pyrazolo[4,3-c]pyridin-5(3H)-yl)-1-oxopent-4-yn-2-yl)carbamate (0.65 g, 1.5 mmol) and trifluoroacetic acid (2 mL) is stirred for 30 min at room temperature. The mixture is carefully basified by the addition of saturated aqueous NaHCO$_3$, extracted with DCM (50 mL×2), and dried over Na$_2$SO$_4$. After filtration, the filtrate is concentrated in vacuo to give the titled compound as a foam (72 mg, 52% yield).

MS (ESI) m/z: 339 (M+H)$^+$.

Step 3: tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxopent-4-yn-2-yl)amino)-2-methyl-1-oxopropan-2-yl)carbamate The title compound is prepared in 95% yield (0.70 g, foam) from (R)-5-((R)-2-aminopent-4-ynoyl)-3a-benzyl-2-methyl-4,5,6,7-tetrahydro-2H-pyrazolo[4,3-c]pyridin-3(3aH)-one (0.48 g, 1.4 mmol) and 2-((tert-butoxycarbonyl)amino)-2-methylpropanoic acid (0.35 g, 1.7 mmol) in a similar manner to Step 3 of Example 2.

MS (ESI) m/z: 524 (M+H)$^+$, 522 (M–H)$^-$.

Step 4: ethyl 3-((R)-5-((R)-3a-benzyl-2-methyl-3-oxo-3a,4,6,7-tetrahydro-2H-pyrazolo[4,3-c]pyridin-5(3H)-yl)-4-(2-((tert-butoxycarbonyl)amino)-2-methylpropanamido)-5-oxopent-1-yn-1-yl)benzoate A mixture of tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxopent-4-yn-2-yl)amino)-2-methyl-1-oxopropan-2-yl)carbamate (0.10 g, 0.19 mmol), ethyl 3-iodobenzoate (63 mg, 0.23 mmol), dichlorobis(triphenylphosphine) palladium (II) (13 mg, 0.019 mmol) and copper iodide (3.6 mg, 0.019 mmol) in THF (2 mL) is added triethylamine (0.080 mL, 0.57 mmol). The mixture is stirred at 50° C. for 2 hours. After cooled to room temperature, the mixture is concentrated in vacuo and the residue is purified by column chromatography (silica gel, eluted with 30-100% EtOAc in hexane) to give the titled compound as a an oil (69 mg, 54% yield).

MS (ESI) m/z: 672 (M+H)$^+$, 670 (M–H)$^-$.

Step 5: ethyl 3-((R)-5-((R)-3a-benzyl-2-methyl-3-oxo-3a,4,6,7-tetrahydro-2H-pyrazolo[4,3-c]pyridin-5(3H)-yl)-4-(2-((tert-butoxycarbonyl)amino)-2-methylpropanamido)-5-oxopentyl)benzoate To a solution of ethyl 3-((R)-5-((R)-3a-benzyl-2-methyl-3-oxo-3a,4,6,7-tetrahydro-2H-pyrazolo[4,3-c]pyridin-5(3H)-yl)-4-(2-((tert-butoxycarbonyl)amino)-2-methylpropanamido)-5-oxopent-1-yn-1-yl)benzoate (69 mg, 0.10 mmol) in MeOH (2 mL) is added ammonium formate (65 mg, 1.0 mmol), formic acid (0.079 mL, 2.1 mmol) and 10% palladium on carbon (13 mg). The mixture is heated to 50° C. and stirred for 2 hours. The mixture is filtered through a pad of Celite (registered trademark) and the filtrate is concentrated in vacuo. The residue is diluted with water (5 mL) and EtOAc (10 mL) for separation. The aqueous layer is extracted with EtOAc (2 mL×2). The combined organic layers are dried over $Na_2SO_4$. After filtration, the filtrate is concentrated in vacuo to give the titled compound as colorless oil.

MS (ESI) m/z: 676 (M+H)$^+$, 674 (M–H)$^-$.

Step 6: 3-((R)-5-((R)-3a-benzyl-2-methyl-3-oxo-3a,4,6,7-tetrahydro-2H-pyrazolo[4,3-c]pyridin-5(3H)-yl)-4-(2-((tert-butoxycarbonyl)amino)-2-methylpropanamido)-5-oxopentyl)benzoic acid The title compound is prepared in 97% yield (51 mg, white solid) from ethyl 3-((R)-5-((R)-3a-benzyl-2-methyl-3-oxo-3a,4,6,7-tetrahydro-2H-pyrazolo[4,3-c]pyridin-5(3H)-yl)-4-(2-((tert-butoxycarbonyl)amino)-2-methylpropanamido)-5-oxopentyl)benzoate (54 mg, 0.080 mmol) in a similar manner to Step 5 of Example 3.

MS (ESI) m/z: 548 (M+H)$^+$, 546 (M–H)$^-$.

Step 7: tert-butyl (1-(((R)-1-((R)-3a-benzyl-2-methyl-3-oxo-3a,4,6,7-tetrahydro-2H-pyrazolo[4,3-c]pyridin-5(3H)-yl)-5-(3-(hydroxymethyl)phenyl)-1-oxopentan-2-yl)amino)-2-methyl-1-oxopropan-2-yl)carbamate The title compound is prepared in 46% yield (23 mg, colorless oil) from 3-((R)-5-((R)-3a-benzyl-2-methyl-3-oxo-3a,4,6,7-tetrahydro-2H-pyrazolo[4,3-c]pyridin-5(3H)-yl)-4-(2-((tert-butoxycarbonyl)amino)-2-methylpropanamido)-5-oxopentyl)benzoic acid (51 mg, 0.078 mmol) in a similar manner to Step 6 of Example 3.

MS (ESI) m/z: 634 (M+H)$^+$, 632 (M–H)$^-$.

Step 8: 2-amino-N—((R)-1-((R)-3a-benzyl-2-methyl-3-oxo-3a,4,6,7-tetrahydro-2H-pyrazolo[4,3-c]pyridin-5(3H)-yl)-5-(3-(hydroxymethyl)phenyl)-1-oxopentan-2-yl)-2-methylpropanamide The title compound is prepared in 62% yield (12 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-5-(3-(hydroxymethyl)phenyl)-1-oxopentan-2-yl)amino)-2-methyl-1-oxopropan-2-yl)carbamate (23 mg, 0.036 mmol) in a similar manner to Step 7 of Example 3.

Example 8

2-amino-N—((R)-1-((R)-3a-benzyl-2-methyl-3-oxo-3a,4,6,7-tetrahydro-2H-pyrazolo[4,3-c]pyridin-5(3H)-yl)-5-(2-(hydroxymethyl)phenyl)-1-oxopentan-2-yl)-2-methylpropanamide Step 1: Ethyl 2-((R)-5-((R)-3a-benzyl-2-methyl-3-oxo-3a,4,6,7-tetrahydro-2H-pyrazolo[4,3-c]pyridin-5(3H)-yl)-4-(2-((tert-butoxycarbonyl)amino)-2-methylpropanamido)-5-oxopent-1-yn-1-yl)benzoate The title compound is prepared in 63% yield (80 mg, oil) from tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxopent-4-yn-2-yl)amino)-2-methyl-1-oxopropan-2-yl)carbamate (0.10 g, 0.19 mmol, Step 3 of Example 7) and ethyl 2-iodobenzoate (63 mg, 0.23 mmol) in a similar manner to Step 4 of Example 7.

MS (ESI) m/z: 672 (M+H)$^+$, 670 (M–H)$^-$.

Step 2: Ethyl 2-((R)-5-((R)-3a-benzyl-2-methyl-3-oxo-3a,4,6,7-tetrahydro-2H-pyrazolo[4,3-c]pyridin-5(3H)-yl)-4-(2-((tert-butoxycarbonyl)amino)-2-methylpropanamido)-5-oxopentyl)benzoate The title compound is prepared in 71% yield (58 mg, colorless oil) from ethyl 2-((R)-5-((R)-3a-benzyl-2-methyl-3-oxo-3a,4,6,7-tetrahydro-2H-pyrazolo[4,3-c]pyridin-5(3H)-yl)-4-(2-((tert-butoxycarbonyl)amino)-2-methylpropanamido)-5-oxopent-1-yn-1-yl)benzoate (80 mg, 0.12 mmol) in a similar manner to Step 5 of Example 7 in the absence of ammonium formate.

MS (ESI) m/z: 676 (M+H)$^+$, 674 (M–H)$^-$.

Step 3: 2-((R)-5-((R)-3a-benzyl-2-methyl-3-oxo-3a,4,6,7-tetrahydro-2H-pyrazolo[4,3-c]pyridin-5(3H)-yl)-4-(2-((tert-butoxycarbonyl)amino)-2-methylpropanamido)-5-oxopentyl)benzoic acid The title compound is prepared in 78% yield (43 mg, white solid) from ethyl 2-((R)-5-((R)-3a-benzyl-2-methyl-3-oxo-3a,4,6,7-tetrahydro-2H-pyrazolo[4,3-c]pyridin-5(3H)-yl)-4-(2-((tert-butoxycarbonyl)amino)-2-methylpropanamido)-5-oxopentyl)benzoate (58 mg, 0.085 mmol) in a similar manner to Step 5 of Example 3.

MS (ESI) m/z: 648 (M+H)$^+$, 646 (M–H)$^-$.

Step 4: tert-butyl (1-(((R)-1-((R)-3a-benzyl-2-methyl-3-oxo-3a,4,6,7-tetrahydro-2H-pyrazolo[4,3-c]pyridin-5(3H)-yl)-5-(2-(hydroxymethyl)phenyl)-1-oxopentan-2-yl)amino)-2-methyl-1-oxopropan-2-yl)carbamate The title compound is prepared in 53% yield (22 mg, colorless oil) from 2-((R)-5-((R)-3a-benzyl-2-methyl-3-oxo-3a,4,6,7-tetrahydro-2H-pyrazolo[4,3-c]pyridin-5(3H)-yl)-4-(2-((tert-butoxycarbonyl)amino)-2-methylpropanamido)-5-oxopentyl)benzoic acid (43 mg, 0.066 mmol) in a similar manner to Step 6 of Example 3.

MS (ESI) m/z: 634 (M+H)$^+$, 632 (M–H)$^-$.

Step 5: 2-amino-N—((R)-1-((R)-3a-benzyl-2-methyl-3-oxo-3a,4,6,7-tetrahydro-2H-pyrazolo[4,3-c]pyridin-5(3H)-yl)-5-(2-(hydroxymethyl)phenyl)-1-oxopentan-2-yl)-2-methylpropanamide The title compound is prepared in 55% yield (10 mg) from tert-butyl (1-(((R)-1-((R)-3a-benzyl-2-methyl-3-oxo-3a,4,6, 7-tetrahydro-2H-pyrazolo[4,3-c]pyridin-5(3H)-yl)-5-(2-(hydroxymethyl)phenyl)-1-oxopentan-2-yl)amino)-2-methyl-1-oxopropan-2-yl)carbamate (22 mg, 0.035 mmol) in a similar manner to Step 7 of Example 3.

Example 9

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-5-(pyridin-2-yl)pentan-2-yl)-2-methylpropanamide Step 1: tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-5-(pyridin-2-yl)pent-4-yn-2-yl)amino)-2-methyl-1-oxopropan-2-yl) carbamate The title compound is prepared in 72% yield (41 mg, oil) from tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxopent-4-yn-2-yl)amino)-2-methyl-1-oxopropan-2-yl)carbamate (50 mg, 0.095 mmol, Step 3 of Example 7) and 2-iodopyridine (23 mg, 0.12 mmol) in a similar manner to Step 4 of Example 7.
MS (ESI) m/z: 601 (M+H)⁺, 599 (M−H)⁻.

Step 2: tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-5-(pyridin-2-yl)pentan-2-yl)amino)-2-methyl-1-oxopropan-2-yl)carbamate The title compound is prepared in 62% yield (25 mg, colorless oil) from tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-5-(pyridin-2-yl)pent-4-yn-2-yl)amino)-2-methyl-1-oxopropan-2-yl)carbamate (41 mg, 0.068 mmol) in a similar manner to Step 5 of Example 7 in the absence of ammonium formate.
MS (ESI) m/z: 605 (M+H)⁺, 603 (M−H)⁻.

Step 3: 2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-5-(pyridin-2-yl)pentan-2-yl)-2-methylpropanamide The title compound is prepared in 47% yield (10 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-5-(pyridin-2-yl)pentan-2-yl)amino)-2-methyl-1-oxopropan-2-yl)carbamate (41 mg, 0.068 mmol) in a similar manner to Step 7 of Example 3.

Example 10

2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-5-(6-(trifluoromethyl)pyridin-2-yl)pentan-2-yl)-2-methylpropanamide Step 1: tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-5-(6-(trifluoromethyl)pyridin-2-yl)pent-4-yn-2-yl)amino)-2-methyl-1-oxopropan-2-yl)carbamate The title compound is prepared in 65% yield (41 mg, oil) from tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxopent-4-yn-2-yl)amino)-2-methyl-1-oxopropan-2-yl)carbamate (50 mg, 0.095 mmol, Step 3 of Example 7)) and 2-bromo-6-(trifluoromethyl)pyridine (26 mg, 0.12 mmol) in a similar manner to Step 4 of Example 7.
MS (ESI) m/z: 669 (M+H)⁺, 667 (M−H)⁻.

Step 2: tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-5-(6-(trifluoromethyl)pyridin-2-yl)pentan-2-yl)amino)-2-methyl-1-oxoproban-2-yl)carbamate The title compound is prepared in 43% yield (18 mg, colorless oil) from tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-5-(6-(trifluoromethyl)pyridin-2-yl)pent-4-yn-2-yl)amino)-2-methyl-1-oxopropan-2-yl)carbamate (41 mg, 0.061 mmol) in a similar manner to Step 5 of Example 7 in the absence of ammonium formate.
MS (ESI) m/z: 673 (M+H)⁺, 671 (M−H)⁻.

Step 3: 2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-5-(6-(trifluoromethyl)pyridin-2-yl)pentan-2-yl)-2-methylpropanamide The title compound is prepared in 60% yield (9.0 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxo-5-(6-(trifluoromethyl)pyridin-2-yl)pentan-2-yl)amino)-2-methyl-1-oxopropan-2-yl)carbamate (25 mg, 0.041 mmol) in a similar manner to Step 7 of Example 3.

Example 11

2-amino-N—((R)-1-((R)-3a-benzyl-2-methyl-3-oxo-3a,4,6,7-tetrahydro-2H-pyrazolo[4,3-c]pyridin-5(3H)-yl)-5-(5-fluoropyridin-2-yl)-1-oxopentan-2-yl)-2-methylpropanamide Step 1: tert-butyl (1-(((R)-1-((R)-3a-benzyl-2-methyl-3-oxo-3a,4,6,7-tetrahydro-2H-pyrazolo[4,3-c]pyridin-5(3H)-yl)-5-(5-fluoropyridin-2-yl)-1-oxopent-4-yn-2-yl)amino)-2-methyl-1-oxopropan-2-yl) carbamate The title compound is prepared in 31% yield (18 mg, oil) from tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxopent-4-yn-2-yl)amino)-2-methyl-1-oxopropan-2-yl)carbamate (50 mg, 0.095 mmol, Step 3 of Example 7) and 2-bromo-5-fluoropyridine (20 mg, 0.12 mmol) in a similar manner to Step 4 of Example 7.
MS (ESI) m/z: 619 (M+H)⁺, 617 (M−H)⁻.

Step 2: tert-butyl (1-(((R)-1-((R)-3a-benzyl-2-methyl-3-oxo-3a,4,6,7-tetrahydro-2H-pyrazolo[4,3-c]pyridin-5(3H)-yl)-5-(5-fluoropyridin-2-yl)-1-oxopentan-2-yl)amino)-2-methyl-1-oxopropan-2-yl) carbamate The title compound is prepared in 85% yield (16 mg, colorless oil) from tert-butyl (1-(((R)-1-((R)-3a-benzyl-2-methyl-3-oxo-3a,4,6,7-tetrahydro-2H-pyrazolo[4,3-c]pyridin-5(3H)-yl)-5-(5-fluoropyridin-2-yl)-1-oxopent-4-yn-2- yl)amino)-2-methyl-1-oxopropan-2-yl)carbamate (18 mg, 0.029 mmol) in a similar manner to Step 5 of Example 7.
MS (ESI) m/z: 623 (M+H)+.

Step 3: 2-amino-N—((R)-1-((R)-3a-benzyl-2-methyl-3-oxo-3a,4,6,7-tetrahydro-2H-pyrazolo[4,3-c]pyridin-5(3H)-yl)-5-(5-fluoropyridin-2-yl)-1-oxopentan-2-yl)-2-methylpropanamide The title compound is prepared in 17% yield (2 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-5-(5-fluoropyridin-2-yl)-1-oxopentan-2-yl)amino)-2-methyl-1-oxopropan-2-yl)carbamate (18 mg, 0.029 mmol) in a similar manner to Step 7 of Example 3.

Example 12

2-amino-N—((R)-1-((R)-3a-benzyl-2-methyl-3-oxo-3a,4,6,7-tetrahydro-2H-pyrazolo[4,3-c]pyridin-5(3H)-yl)-5-(6-methylpyridin-2-yl)-1-oxopentan-2-yl)-2-methylpropanamide Step 1: tert-butyl (1-(((R)-1-((R)-3a-benzyl-2-methyl-3-oxo-3a,4,6,7-tetrahydro-2H-pyrazolo[4,3-c]pyridin-5(3H)-yl)-5-(6-methylpyridin-2-yl)-1-oxopent-4-yn-2-yl)amino)-2-methyl-1-oxopropan-2-yl)carbamate The title compound is prepared in 65% yield (54 mg, oil) from tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxopent-4-yn-2-yl)amino)-2-methyl-1-oxopropan-2-yl)carbamate (70 mg, 0.13 mmol, Step 3 of Example 7) and 2-bromo-6-methylpyridine (28 mg, 0.16 mmol) in a similar manner to Step 4 of Example 7.
MS (ESI) m/z: 615 (M+H)+, 613 (M−H)−.

Step 2: tert-butyl (1-(((R)-1-((R)-3a-benzyl-2-methyl-3-oxo-3a,4,6,7-tetrahydro-2H-pyrazolo[4,3-c]pyridin-5(3H)-yl)-5-(6-methylpyridin-2-yl)-1-oxopentan-2-yl)amino)-2-methyl-1-oxopropan-2-yl)carbamate The title compound is prepared in >99% yield (55 mg, colorless oil) from tert-butyl (1-(((R)-1-((R)-3a-benzyl-2-methyl-3-oxo-3a,4,6,7-tetrahydro-2H-pyrazolo[4,3-c]pyridin-5(3H)-yl)-5-(6-methylpyridin-2-yl)-1-oxopent-4-yn-2-yl)amino)-2-methyl-1-oxopropan-2-yl)carbamate (54 mg, 0.087 mmol) in a similar manner to Step 5 of Example 7.
MS (ESI) m/z: 619 (M+H)+, 617 (M−H)−.

Step 3: 2-amino-N—((R)-1-((R)-3a-benzyl-2-methyl-3-oxo-3a,4,6,7-tetrahydro-2H-pyrazolo[4,3-c]pyridin-5(3H)-yl)-5-(6-methylpyridin-2-yl)-1-oxopentan-2-yl)-2-methylpropanamide The title compound is prepared in 30% yield (14 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-5-(6-methylpyridin-2-yl)-1-oxopentan-2-yl)amino)-2-methyl-1-oxopropan-2-yl)carbamate (55 mg, 0.089 mmol) in a similar manner to Step 7 of Example 3.

Example 13

2-amino-N—((R)-1-((R)-3a-benzyl-2-methyl-3-oxo-3a,4,6,7-tetrahydro-2H-pyrazolo[4,3-c]pyridin-5(3H)-yl)-5-(6-(difluoromethyl)pyridin-2-yl)-1-oxopentan-2-yl)-2-methylpropanamide Step 1: tert-butyl (1-(((R)-1-((R)-3a-benzyl-2-methyl-3-oxo-3a,4,6,7-tetrahydro-2H-pyrazolo[4,3-c]pyridin-5(3H)-yl)-5-(6-(difluoromethyl)pyridin-2-yl)-1-oxopent-4-yn-2-yl)amino)-2-methyl-1-oxopropan-2-yl)carbamate The title compound is prepared in 90% yield (0.17 g, oil) from tert-butyl (1-(((R)-1-((R)-3a-benzyl-2-methyl-3-oxo-3a,4,6,7-tetrahydro-2H-pyrazolo[4,3-c]pyridin-5(3H)-yl)-1-oxopent-4-yn-2-yl)amino)-2-methyl-1-oxopropan-2-yl)carbamate (0.15 g, 0.29 mmol, Step 3 of Example 7) and 2-bromo-6-(difluoromethyl)pyridine (72 mg, 0.34 mmol) in a similar manner to Step 4 of Example 7.
MS (ESI) m/z: 651 (M+H)+, 649 (M−H)−.

Step 2: tert-butyl (1-(((R)-1-((R)-3a-benzyl-2-methyl-3-oxo-3a,4,6,7-tetrahydro-2H-pyrazolo[4,3-c]pyridin-5(3H)-yl)-5-(6-(difluoromethyl)pyridin-2-yl)-1-oxopentan-2-yl)amino)-2-methyl-1-oxopropan-2-yl)carbamate A mixture of tert-butyl (1-(((R)-1-((R)-3a-benzyl-2-methyl-3-oxo-3a,4,6,7-tetrahydro-2H-pyrazolo[4,3-c]pyridin-5(3H)-yl)-5-(6-(difluoromethyl)pyridin-2-yl)-1-oxopent-4-yn-2-yl)amino)-2-methyl-1-oxopropan-2-yl)carbamate (92 mg, 0.14 mmol) and platinum (IV) oxide (18 mg, 0.079 mmol) in MeOH is stirred under hydrogen atmosphere at room temperature for 1 hour. The mixture is filtered through a pad of Celite (registered trademark). The filtrate is concentrated in vacuo to give the titled compound as a mixture with an impurity (0.10 g, >99% yield).
MS (ESI) m/z: 655 (M+H)+, 653 (M−H)−.

Step 3: 2-amino-N—((R)-1-((R)-3a-benzyl-2-methyl-3-oxo-3a,4,6,7-tetrahydro-2H-pyrazolo[4,3-c]pyridin-5(3H)-yl)-5-(6-(difluoromethyl)pyridin-2-yl)-1-oxopentan-2-yl)-2-methylpropanamide The title compound is prepared in 31% yield (12 mg) from tert-butyl (1-(((R)-1-((R)-3a-benzyl-2-methyl-3-oxo-3a,4,6,7-tetrahydro-2H-pyrazolo[4,3-c]pyridin-5(3H)-yl)-5-(6-(difluoromethyl)pyridin-2-yl)-1-oxopentan-2-yl)amino)-2-methyl-1-oxopropan-2-yl)carbamate (46 mg, 0.070 mmol) in a similar manner to Step 7 of Example 3.

Example 14

2-amino-2-methyl-N—((R)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)-4-phenylbutan-2-yl) propanamide Step 1: tert-butyl (2-methyl-1-oxo-1-(((R)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)-4-phenylbutan-2-yl)amino)propan-2-yl)carbamate The title compound is prepared in 90% yield (64 mg, foam) from (R)-3a-(pyridin-2-ylmethyl)-2-(2,2,2-trifluoroethyl)-4,5,6,7-tetrahydro-2H-pyrazolo[4,3-c]pyridin-3 (3aH)-one (2S,3S)-2,3-dihydroxysuccinate (50 mg, 0.11 mmol) and (R)-2-(2-((tert-butoxycarbonyl)amino)-2-methylpropanamido)-4-phenylbutanoic acid (47 mg, 0.13 mmol, Step 2 of Intermediate 6) in a similar manner to Step 1 of Example 1.

MS (ESI) m/z: 659 (M+H)$^+$, 657 (M−H)$^-$.

Step 2: 2-amino-2-methyl-N—((R)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5 (3H)-yl)-4-phenylbutan-2-yl) propanamide The title compound is prepared in 11% yield (6.0 mg) from tert-butyl (2-methyl-1-oxo-1-(((R)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)-4-phenylbutan-2-yl)amino)propan-2-yl)carbamate (61 mg, 0.093 mmol) in a similar manner to Step 7 of Example 3.

Example 15

2-amino-2-methyl-N—((R)-4-(2-(methylsulfonyl) phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl) propanamide Step 1: tert-butyl (4-(2-(methylsulfonyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)carbamate The title compound is prepared in 39% yield (64 mg, foam) from (R)-3a-(pyridin-2-ylmethyl)-2-(2,2,2-trifluoroethyl)-4,5,6,7-tetrahydro-2H-pyrazolo[4,3-c]pyridin-3 (3aH)-one (2S,3S)-2,3-dihydroxysuccinate (0.12 g, 0.25 mmol) and 2-((tert-butoxycarbonyl)amino)-4-(2-(methylsulfonyl)phenyl)butanoic acid (0.11 g, 0.30 mmol, Step 3 of Intermediate 1) in a similar manner to Step 1 of Example 1.

MS (ESI) m/z: 652 (M+H)$^+$.

Step 2: (3aR)-5-(2-amino-4-(2-(methylsulfonyl)phenyl) butanoyl)-3a-(pyridin-2-ylmethyl)-2-(2,2,2-trifluoroethyl)-4,5,6,7-tetrahydro-2H-pyrazolo[4,3-c]pyridin-3(3aH)-one The title compound is prepared in 85% yield (46 mg, oil) from tert-butyl (4-(2-(methylsulfonyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)carbamate (64 mg, 0.098 mmol) in a similar manner to Step 2 of Example 1.

MS (ESI) m/z: 552 (M+H)$^+$.

Step 3: tert-butyl (2-methyl-1-((4-(2-(methylsulfonyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl) amino)-1-oxopropan-2-yl)carbamate The title compound is prepared in >99% yield (61 mg) from (3aR)-5-(2-amino-4-(2-(methylsulfonyl)phenyl)butanoyl)-3a-(pyridin-2-ylmethyl)-2-(2,2,2-trifluoroethyl)-4,5,6,7-tetrahydro-2H-pyrazolo[4,3-c]pyridin-3(3aH)-one (46 mg, 0.083 mmol) and 2-((tert-butoxycarbonyl)amino)-2-methylpropanoic acid (25 mg, 0.12 mmol) in a similar manner to Step 3 of Example 2.

MS (ESI) m/z: 737 (M+H)$^+$.

Step 4: 2-amino-2-methyl-N—((R)-4-(2-(methylsulfonyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)propanamide The title compound is prepared in 16% yield (8.0 mg) from tert-butyl (2-methyl-1-((4-(2-(methylsulfonyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)amino)-1-oxopropan-2-yl)carbamate (61 mg, 0.083 mmol) in a similar manner to Step 7 of Example 3.

Example 16

2-amino-N—((R)-4-(4-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide Step 1: tert-butyl (4-(4-bromophenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)carbamate The title compound is prepared in 38% yield (0.15 g, white solid) from (R)-3a-(pyridin-2-ylmethyl)-2-(2,2,2-trifluoroethyl)-4,5,6,7-tetrahydro-2H-pyrazolo[4,3-c]pyridin-3 (3aH)-one (2S,3S)-2,3-dihydroxysuccinate (0.12 g, 0.25 mmol) and 4-(4-bromophenyl)-2-((tert-butoxycarbonyl) amino)butanoic acid (0.24 g, 0.66 mmol, Step 2 of Intermediate 7) in a similar manner to Step 1 of Example 1.

MS (ESI) m/z: 652 (M+H)$^+$, 650 (M−H)$^-$.

Step 2: ethyl 4-(3-((tert-butoxycarbonyl)amino)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)benzoate The title compound is prepared in 91% yield (0.13 g, colorless oil) from tert-butyl (4-(4-bromophenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5 (3H)-yl)butan-2-yl)carbamate (0.15 g, 0.23 mmol) in a similar manner to Step 4 of Example 3.

MS (ESI) m/z: 656 (M+H)$^+$.

Step 3: ethyl 4-(3-amino-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl) butyl)benzoate The title compound is prepared in 78% yield (88 mg, colorless oil) from ethyl 4-(3-((tert-butoxycarbonyl)amino)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)benzoate (0.13 g, 0.21 mmol) in a similar manner to Step 2 of Example 7.

MS (ESI) m/z: 546 (M+H)$^+$.

Step 4: ethyl 4-(3-(2-((tert-butoxycarbonyl)amino)-2-methylpropanamido)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)benzoate The title compound is prepared in >99% yield (0.12 g, oil) from ethyl 4-(3-amino-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)benzoate (87 mg, 0.16 mmol) and 2-((tert-butoxycarbonyl)amino)-2-methylpropanoic acid (49 mg, 0.24 mmol) in a similar manner to Step 3 of Example 2.

MS (ESI) m/z: 731 (M+H)$^+$, 729 (M−H)$^-$.

Step 5: 4-(3-(2-((tert-butoxycarbonyl)amino)-2-methylpropanamido)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)benzoic acid The title compound is prepared in 62% yield (70 mg, white solid) from ethyl 4-(3-(2-((tert-butoxycarbonyl)amino)-2-methylpropanamido)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)benzoate (0.12 g, 0.16 mmol) in a similar manner to Step 5 of Example 3.

MS (ESI) m/z: 703 (M+H)$^+$, 701 (M−H)$^-$.

Step 6: tert-butyl (1-((4-(4-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)amino)-2-methyl-1-oxopropan-2-yl)carbamate The title compound is prepared in >99% yield (71 mg, oil) from 4-(3-(2-((tert-butoxycarbonyl)amino)-2-methylpropanamido)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)benzoic acid (70 mg, 0.10 mmol) in a similar manner to Step 6 of Example 3.

MS (ESI) m/z: 689 (M+H)$^+$, 687 (M−H)$^-$.

Step 7: 2-amino-N—((R)-4-(4-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide The title compound is prepared in 11% yield (6.0 mg) from tert-butyl (1-((4-(4-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)amino)-2-methyl-1-oxopropan-2-yl)carbamate (70 mg, 0.10 mmol) in a similar manner to Step 7 of Example 3.

Example 17

2-amino-N—((R)-4-(4-fluoro-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide

Step 1: tert-butyl (4-(2-bromo-4-fluorophenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)carbamate The title compound is prepared in 75% yield (0.22 g, white solid) from (R)-3a-(pyridin-2-ylmethyl)-2-(2,2,2-trifluoroethyl)-4,5,6,7-tetrahydro-2H-pyrazolo[4,3-c]pyridin-3(3aH)-one (2S,3S)-2,3-dihydroxysuccinate (0.23 g, 0.50 mmol) and 4-(2-bromo-4-fluorophenyl)-2-((tert-butoxycarbonyl)amino)butanoic acid (0.23 g, 0.60 mmol, Step 3 of Intermediate 8) in a similar manner to Step 1 of Example 1.

MS (ESI) m/z: 670 (M+H)$^+$.

Step 2: (3aR)-5-(2-amino-4-(2-bromo-4-fluorophenyl)butanoyl)-3a-(pyridin-2-ylmethyl)-2-(2,2,2-trifluoroethyl)-4,5,6,7-tetrahydro-2H-pyrazolo[4,3-c]pyridin-3(3aH)-one The title compound is prepared in 81% yield (0.17 g, white solid) from tert-butyl (4-(2-bromo-4-fluorophenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)carbamate (0.25 g, 0.37 mmol) in a similar manner to Step 2 of Example 1.

MS (ESI) m/z: 570 (M+H)$^+$.

Step 3: tert-butyl (1-((4-(2-bromo-4-fluorophenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)amino)-2-methyl-1-oxopropan-2-yl)carbamate The title compound is prepared in >99% yield (0.23 g, oil) from (3aR)-5-(2-amino-4-(2-bromo-4-fluorophenyl)butanoyl)-3a-(pyridin-2-ylmethyl)-2-(2,2,2-trifluoroethyl)-4,5,6,7-tetrahydro-2H-pyrazolo[4,3-c]pyridin-3(3aH)-one (0.17 g, 0.30 mmol) and 2-((tert-butoxycarbonyl)amino)-2-methylpropanoic acid (92 mg, 0.45 mmol) in a similar manner to Step 3 of Example 2.

MS (ESI) m/z: 755 (M+H)$^+$, 753 (M−H)$^-$.

Step 4: ethyl 2-(3-(2-((tert-butoxycarbonyl)amino)-2-methylpropanamido)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)-5-fluorobenzoate The title compound is prepared in >99% yield (0.28 g, oil) from tert-butyl (1-((4-(2-bromo-4-fluorophenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)amino)-2-methyl-1-oxopropan-2-yl)carbamate (0.23 g, 0.30 mmol) in a similar manner to Step 4 of Example 3.

MS (ESI) m/z: 749 (M+H)$^+$.

Step 5: 2-(3-(2-((tert-butoxycarbonyl)amino)-2-methylpropanamido)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)-5-fluorobenzoic acid The title compound is prepared in 39% yield (84 mg, white solid) from ethyl 2-(3-(2-((tert-butoxycarbonyl)amino)-2-methylpropanamido)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)-5-fluorobenzoate (0.23 g, 0.30 mmol) in a similar manner to Step 5 of Example 3.

MS (ESI) m/z: 721 (M+H)$^+$, 719 (M−H)$^−$.

Step 6: tert-butyl (1-((4-(4-fluoro-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)amino)-2-methyl-1-oxopropan-2-yl)carbamate The title compound is prepared in 57% yield (47 mg, oil) from 2-(3-(2-((tert-butoxycarbonyl)amino)-2-methylpropanamido)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)-5-fluorobenzoic acid (84 mg, 0.12 mmol) in a similar manner to Step 6 of Example 3.

MS (ESI) m/z: 707 (M+H)$^+$, 705 (M−H)$^−$.

Step 7: 2-amino-N—((R)-4-(4-fluoro-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide The title compound is prepared in 17% yield (7.0 mg) from tert-butyl (1-((4-(4-fluoro-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)amino)-2-methyl-1-oxopropan-2-yl)carbamate (47 mg, 0.067 mmol) in a similar manner to Step 7 of Example 3.

Example 18

2-amino-N—((R)-4-(3-fluoro-4-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide Step 1: tert-butyl (4-(4-bromo-3-fluorophenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)carbamate The title compound is prepared in 60% yield (0.20 g, white solid) from (R)-3a-(pyridin-2-ylmethyl)-2-(2,2,2-trifluoroethyl)-4,5,6,7-tetrahydro-2H-pyrazolo[4,3-c]pyridin-3(3aH)-one (2S,3S)-2,3-dihydroxysuccinate (0.20 g, 0.50 mmol) and 4-(4-bromo-3-fluorophenyl)-2-((tert-butoxycarbonyl)amino)butanoic acid (0.23 g, 0.60 mmol, Step 3 of Intermediate 9) in a similar manner to Step 1 of Example 1.

MS (ESI) m/z: 670 (M+H)$^+$.

Step 2: (3aR)-5-(2-amino-4-(4-bromo-3-fluorophenyl)butanoyl)-3a-(pyridin-2-ylmethyl)-2-(2,2,2-trifluoroethyl)-4,5,6,7-tetrahydro-2H-pyrazolo[4,3-c]pyridin-3(3aH)-one The title compound is prepared in 71% yield (0.12 g, oil) from tert-butyl (4-(4-bromo-3-fluorophenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)carbamate (0.25 g, 0.37 mmol) in a similar manner to Step 2 of Example 1.

MS (ESI) m/z: 570 (M+H)$^+$.

Step 3: tert-butyl (1-((4-(4-bromo-3-fluorophenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)amino)-2-methyl-1-oxopropan-2-yl)carbamate The title compound is prepared in >99% yield (0.18 g, colorless oil) from (3aR)-5-(2-amino-4-(4-bromo-3-fluorophenyl)butanoyl)-3a-(pyridin-2-ylmethyl)-2-(2,2,2-trifluoroethyl)-4,5,6,7-tetrahydro-2H-pyrazolo[4,3-c]pyridin-3(3aH)-one (0.12 g, 0.21 mmol) and 2-((tert-butoxycarbonyl)amino)-2-methylpropanoic acid (65 mg, 0.32 mmol) in a similar manner to Step 3 of Example 2.

MS (ESI) m/z: 755 (M+H)$^+$, 753 (M−H)$^−$.

Step 4: ethyl 4-(3-(2-((tert-butoxycarbonyl)amino)-2-methylpropanamido)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)-2-fluorobenzoate The title compound is prepared in >99% yield (0.18 g, brown solid) from tert-butyl (1-((4-(4-bromo-3-fluorophenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)amino)-2-methyl-1-oxopropan-2-yl)carbamate (0.18 g, 0.23 mmol) in a similar manner to Step 4 of Example 3.

MS (ESI) m/z: 749 (M+H)$^+$.

Step 5: 4-(3-(2-((tert-butoxycarbonyl)amino)-2-methylpropanamido)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)-2-fluorobenzoic acid The title compound is prepared in 64% yield (0.11 g, oil) from ethyl 4-(3-(2-((tert-butoxycarbonyl)amino)-2-methylpropanamido)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)-2-fluorobenzoate (0.18 g, 0.23 mmol) in a similar manner to Step 5 of Example 3.

MS (ESI) m/z: 721 (M+H)$^+$, 719 (M−H)$^−$.

Step 6: tert-butyl (1-((4-(3-fluoro-4-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)amino)-2-methyl-1-oxopropan-2-yl)carbamate The title compound is prepared in 22% yield (24 mg, oil) from 4-(3-(2-((tert-butoxycarbonyl)amino)-2-methylpropanamido)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)-2-fluorobenzoic acid (0.11 g, 0.15 mmol) in a similar manner to Step 6 of Example 3.

MS (ESI) m/z: 707 (M+H)$^+$, 705 (M−H)$^−$.

Step 7: 2-amino-N—((R)-4-(3-fluoro-4-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide The title compound is prepared in 17% yield (4.0 mg) from tert-butyl (1-((4-(3-fluoro-4-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)amino)-2-methyl-1-oxopropan-2-yl)carbamate (24 mg, 0.033 mmol) in a similar manner to Step 7 of Example 3.

Example 19

2-amino-N—((R)-4-(5-fluoro-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide Step 1: tert-butyl (4-(2-bromo-5-fluorophenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)carbamate The title compound is prepared in 69% yield (0.23 g, yellow solid) from (R)-3a-(pyridin-2-ylmethyl)-2-(2,2,2-trifluoroethyl)-4,5,6,7-tetrahydro-2H-pyrazolo[4,3-c]pyridin-3(3aH)-one (2S,3S)-2,3-dihydroxysuccinate (0.20 g, 0.50 mmol) and 4-(2-bromo-5-fluorophenyl)-2-((tert-butoxycarbonyl)amino)butanoic acid (0.23 g, 0.60 mmol, Step 2 of Intermediate 1) in a similar manner to Step 1 of Example 1.

MS (ESI) m/z: 670 (M+H)$^+$, 668 (M−H)$^−$.

Step 2: (3aR)-5-(2-amino-4-(2-bromo-5-fluorophenyl)butanoyl)-3a-(pyridin-2-ylmethyl)-2-(2,2,2-trifluoroethyl)-4,5,6,7-tetrahydro-2H-pyrazolo[4,3-c]pyridin-3(3aH)-one The title compound is prepared in 95% yield (0.19 g, white solid) from tert-butyl (4-(4-bromo-3-fluorophenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)carbamate (0.23 g, 0.34 mmol) in a similar manner to Step 2 of Example 1.

MS (ESI) m/z: 570 (M+H)$^+$.

Step 3: tert-butyl (1-((4-(2-bromo-5-fluorophenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)amino)-2-methyl-1-oxopropan-2-yl)carbamate The title compound is prepared in 98% yield (0.24 g, colorless gum) from (3aR)-5-(2-amino-4-(2-bromo-5-fluorophenyl)butanoyl)-3a-(pyridin-2-ylmethyl)-2-(2,2,2-trifluoroethyl)-4,5,6,7-tetrahydro-2H-pyrazolo[4,3-c]pyridin-3(3aH)-one (0.19 g, 0.33 mmol) and 2-((tert-butoxycarbonyl)amino)-2-methylpropanoic acid (99 mg, 0.49 mmol) in a similar manner to Step 3 of Example 2.

MS (ESI) m/z: 755 (M+H)$^+$, 753 (M−H)$^−$.

Step 4: ethyl 2-(3-(2-((tert-butoxycarbonyl)amino)-2-methylpropanamido)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)-4-fluorobenzoate The title compound is prepared in >99% yield (0.24 g, brown solid) from tert-butyl (1-((4-(2-bromo-5-fluorophenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)amino)-2-methyl-1-oxopropan-2-yl)carbamate (0.24 g, 0.32 mmol) in a similar manner to Step 4 of Example 3.

MS (ESI) m/z: 749 (M+H)$^+$, 747 (M−H)$^−$.

Step 5: 2-(3-(2-((tert-butoxycarbonyl)amino)-2-methylpropanamido)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)-4-fluorobenzoic acid The title compound is prepared in 94% yield (0.22 g, yellow gum) from ethyl 2-(3-(2-((tert-butoxycarbonyl)amino)-2-methylpropanamido)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)-4-fluorobenzoate (0.24 g, 0.32 mmol) in a similar manner to Step 5 of Example 3.

MS (ESI) m/z: 721 (M+H)$^+$, 719 (M−H)$^−$.

Step 6: tert-butyl (1-((4-(5-fluoro-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)amino)-2-methyl-1-oxopropan-2-yl)carbamate The title compound is prepared in 46% yield (98 mg, white solid) from 2-(3-(2-((tert-butoxycarbonyl)amino)-2-methylpropanamido)-4-oxo-4-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butyl)-4-fluorobenzoic acid (0.22 g, 0.30 mmol) in a similar manner to Step 6 of Example 3.

MS (ESI) m/z: 707 (M+H)$^+$, 705 (M−H)$^−$.

Step 7: 2-amino-N—((R)-4-(5-fluoro-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide The title compound is prepared in 11% yield (9.0 mg) from tert-butyl (1-((4-(5-fluoro-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)amino)-2-methyl-1-oxopropan-2-yl)carbamate (98 mg, 0.14 mmol) in a similar manner to Step 7 of Example 3.

TABLE 5-1

| Example | Name | Structure | tR (min) | m/z | Ion mode | Condition | Method |
|---|---|---|---|---|---|---|---|
| 1 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(2-(methylsulfonyl)phenyl)-1-oxobutan-2-yl)-2-methylpropanamide | 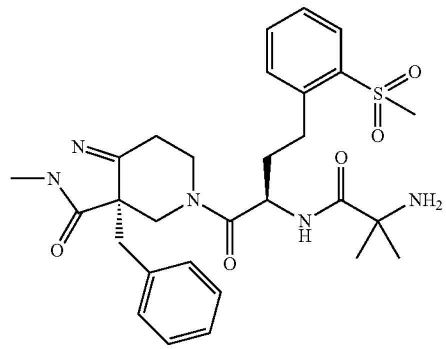 | 1.31 | 566.3 | (M − H)⁻ | B | QC1 |
| 2 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-4-phenylbutan-2-yl)-2-methylpropanamide | 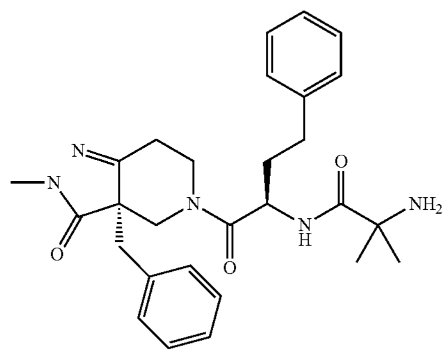 [SMILES: CNC(=O)[C@]1(Cc2ccccc2)CN(C(=O)[C@@H](CCc2ccccc2)NC(=O)C(C)(C)N)CCC1=N] | 1.47 | 490.3 | (M − H)⁻ | A | QC1 |
| 3 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(2-chloro-4-(hydroxymethyl)phenyl)-1-oxobutan-2-yl)-2-methylpropanamide | 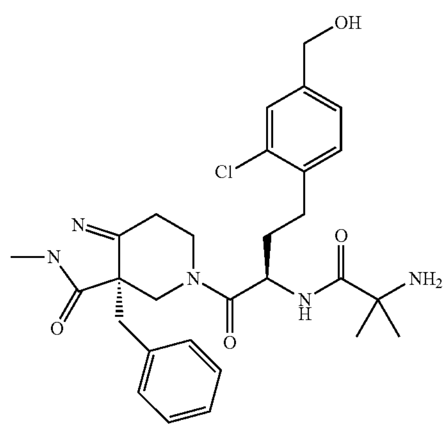 [SMILES: CNC(=O)[C@]1(Cc2ccccc2)CN(C(=O)[C@@H](CCc2ccc(CO)cc2Cl)NC(=O)C(C)(C)N)CCC1=N] | 1.79 | 552.3 | (M − H)⁻ | A | QC2 |
| 4 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(2-fluoro-4-(hydroxymethyl)phenyl)-1-oxobutan-2-yl)-2-methylpropanamide | 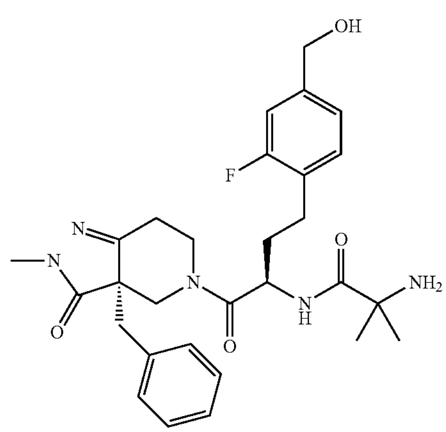 [SMILES: CNC(=O)[C@]1(Cc2ccccc2)CN(C(=O)[C@@H](CCc2ccc(CO)cc2F)NC(=O)C(C)(C)N)CCC1=N] | 1.25 | 536.4 | (M − H)⁻ | A | QC1 |

TABLE 5-1-continued

| Example | Name | Structure | tR (min) | m/z | Ion mode | Condition | Method |
|---|---|---|---|---|---|---|---|
| 5 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(2-fluoro-5-(hydroxymethyl)phenyl)-1-oxobutan-2-yl)-2-methylpropanamide | 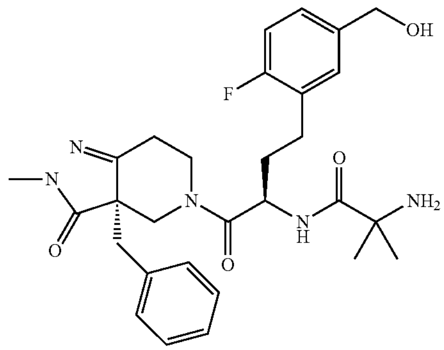 [SMILES: CNC(=O)[C@]1(Cc2ccccc2)CN(C(=O)[C@@H](CCc2cc(CO)ccc2F)NC(=O)C(C)(C)N)CCC1=N] | 1.28 | 536.4 | (M − H)⁻ | A | QC1 |
| 6 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(2-(hydroxymethyl)phenyl)-1-oxobutan-2-yl)-2-methylpropanamide | 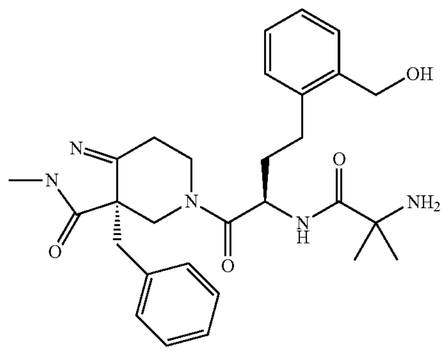 [SMILES: CNC(=O)[C@]1(Cc2ccccc2)CN(C(=O)[C@@H](CCc2ccccc2CO)NC(=O)C(C)(C)N)CCC1=N] | 1.28 | 520.3 | (M + H)⁺ | B | QC2 |
| 7 | 2-amino-N-((R)-1-((R)-3a-benzyl-2-methyl-3-oxo-3a,4,6,7-tetrahydro-2H-pyrazolo[4,3-c]pyridin-5(3H)-yl)-5-(3-(hydroxymethyl)phenyl)-1-oxopentan-2-yl)-2-methylpropanamide | 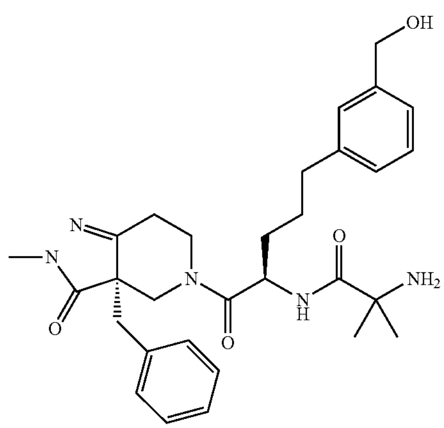 [SMILES: CNC(=O)[C@]1(Cc2ccccc2)CN(C(=O)[C@@H](CCCc2cccc(CO)c2)NC(=O)C(C)(C)N)CCC1=N] | 1.30 | 532.5 | (M − H)⁻ | A | QC2 |
| 8 | 2-amino-N-((R)-1-((R)-3a-benzyl-2-methyl-3-oxo-3a,4,6,7-tetrahydro-2H-pyrazolo[4,3-c]pyridin-5(3H)-yl)-5-(2-(hydroxymethyl)phenyl)-1-oxopentan-2-yl)-2-methylpropanamide | 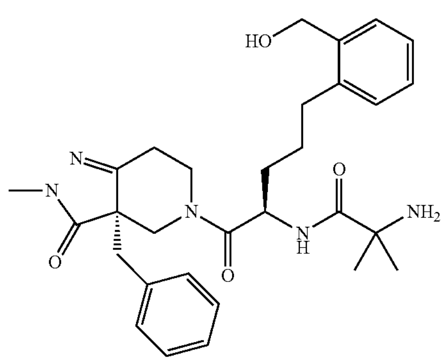 [SMILES: CNC(=O)[C@]1(Cc2ccccc2)CN(C(=O)[C@@H](CCCc2ccccc2CO)NC(=O)C(C)(C)N)CCC1=N] | 1.33 | 534.3 | (M + H)⁺ | A | QC2 |

TABLE 5-1-continued

| Example | Name | Structure | tR (min) | m/z | Ion mode | Condition | Method |
|---|---|---|---|---|---|---|---|
| 9 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-5-(pyridin-2-yl)pentan-2-yl)-2-methylpropanamide | 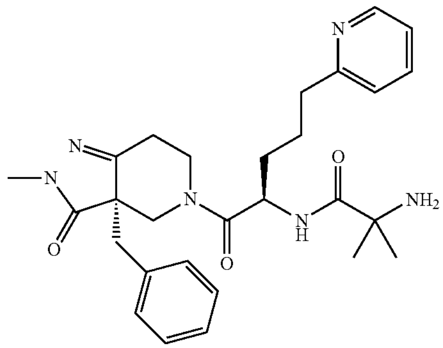 [SMILES: CNC(=O)[C@]1(Cc2ccccc2)CN(C(=O)[C@@H](CCCc2ccccn2)NC(=O)C(C)(C)N)CCC1=N] | 1.24 | 503.4 | (M − H)− | A | QC2 |

TABLE 5-2

| Example | Name | Structure | tR (min) | m/z | Ion mode | Condition | Method |
|---|---|---|---|---|---|---|---|
| 10 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-5-(6-(trifluoromethyl)pyridin-2-yl)pentan-2-yl)-2-methylpropanamide | 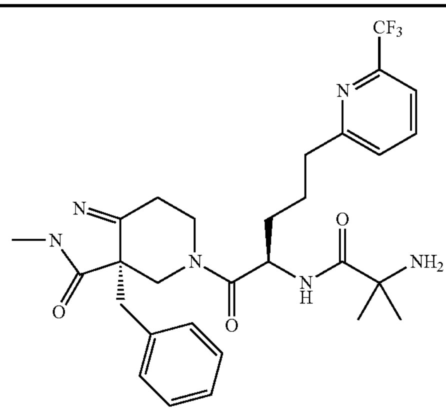 | 1.48 | 571.4 | (M − H)− | A | QC1 |
| 11 | 2-amino-N-((R)-1-((R)-3a-benzyl-2-methyl-3-oxo-3a,4,6,7-tetrahydro-2H-pyrazolo[4,3-c]pyridin-5(3H)-yl)-5-(5-fluoropyridin-2-yl)-1-oxopentan-2-yl)-2-methylpropanamide | 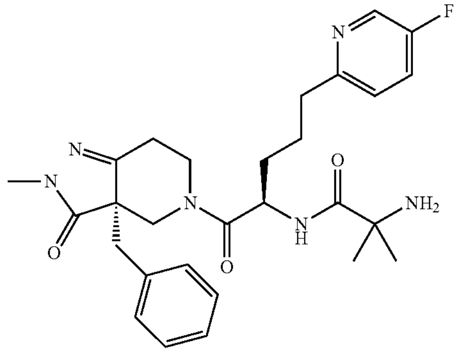 [SMILES: CNC(=O)[C@]1(Cc2ccccc2)CN(C(=O)[C@@H](CCCc2ccc(F)cn2)NC(=O)C(C)(C)N)CCC1=N] | 1.32 | 523.2 | (M + H)+ | A | QC1 |

TABLE 5-2-continued

| # | Name | Structure | RT | MS | | | |
|---|---|---|---|---|---|---|---|
| 12 | 2-amino-N-((R)-1-((R)-3a-benzyl-2-methyl-3-oxo-3a,4,6,7-tetrahydro-2H-pyrazolo[4,3-c]pyridin-5(3H)-yl)-5-(6-methylpyridin-2-yl)-1-oxopentan-2-yl)-2-methylpropanamide | 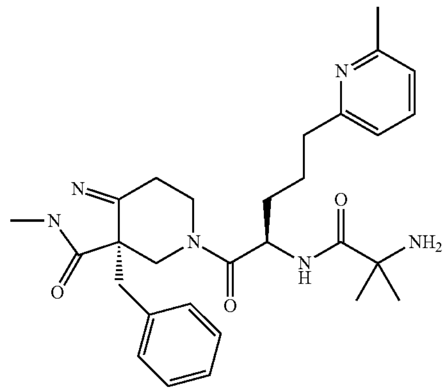 [SMILES: CNC(=O)[C@]1(Cc2ccccc2)CN(C(=O)[C@@H](CCCc2cccc(C)n2)NC(=O)C(C)(C)N)CCC1=N] | 1.31 | 519.3 | (M + H)+ | A | QC1 |
| 13 | 2-amino-N-((R)-1-((R)-3a-benzyl-2-methyl-3-oxo-3a,4,6,7-tetrahydro-2H-pyrazolo[4,3-c]pyridin-5(3H)-yl)-5-(6-(difluoromethyl)pyridin-2-yl)-1-oxopentan-2-yl)-2-methylpropanamide | 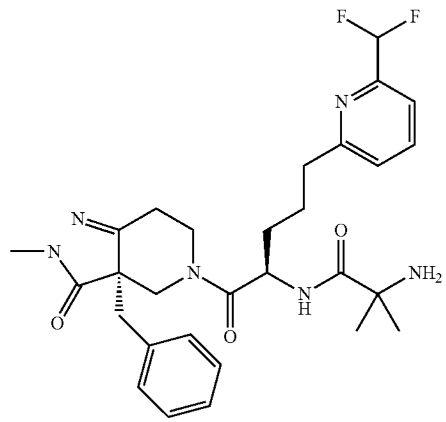 [SMILES: CNC(=O)[C@]1(Cc2ccccc2)CN(C(=O)[C@@H](CCCc2cccc(C(F)F)n2)NC(=O)C(C)(C)N)CCC1=N] | 1.40 | 555.2 | (M + H)+ | A | QC1 |
| 14 | 2-amino-2-methyl-N-((R)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)-4-phenylbutan-2-yl)propanamide | 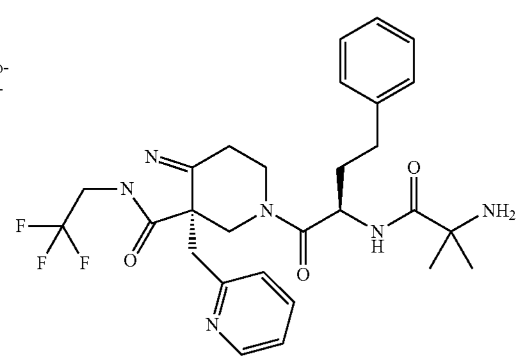 | 1.51 | 559.3 | (M + H)+ | A | QC1 |
| 15 | 2-amino-2-methyl-N-((R)-4-(2-(methylsulfonyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)propanamide | 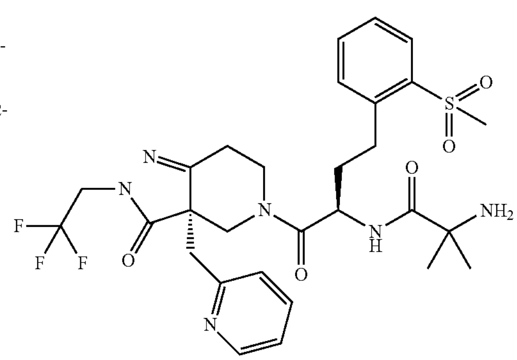 | 1.35 | 635.2 | (M − H)− | B | QC1 |

TABLE 5-2-continued

| | | | | | | | |
|---|---|---|---|---|---|---|---|
| 16 | 2-amino-N-((R)-4-(4-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide | 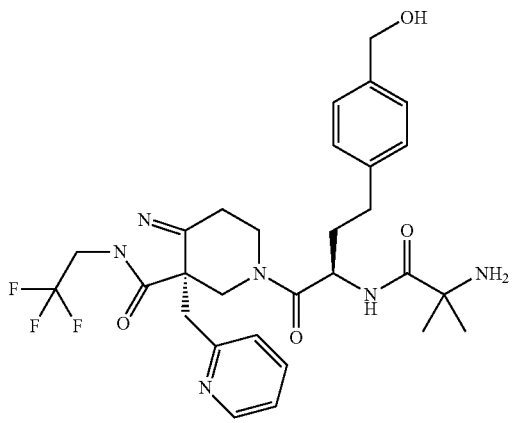 [SMILES: CC(C)(N)C(=O)N[C@H](CCc1ccc(CO)cc1)C(=O)N1CCC(=N)[C@](Cc2ccccn2)(C(=O)NCC(F)(F)F)C1] | 1.26 | 587.4 | (M − H)⁻ | A | QC1 |
| 17 | 2-amino-N-((R)-4-(4-(fluoromethyl)-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide | 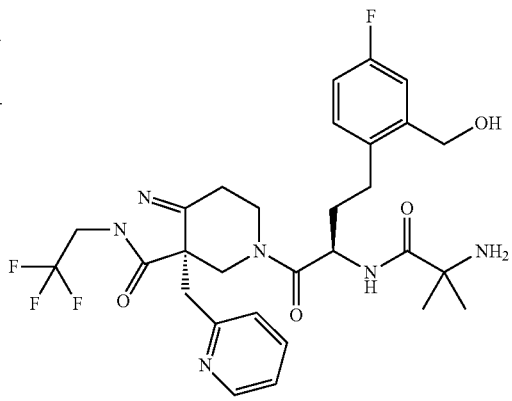 | 1.37 | 605.3 | (M − H)⁻ | A | QC1 |
| 18 | 2-amino-N-((R)-4-(3-fluoro-4-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide | 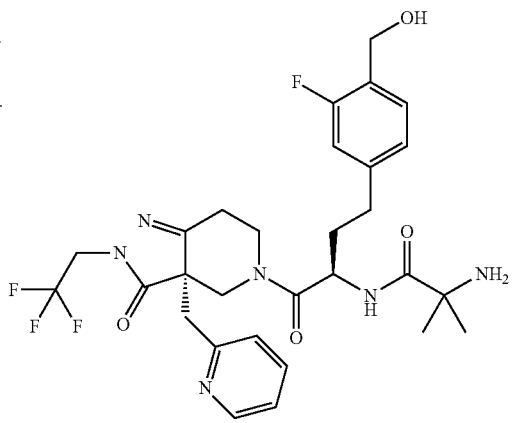 | 1.30 | 605.3 | (M − H)⁻ | A | QC1 |
| 18 | 2-amino-N-((R)-4-(5-fluoro-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide | 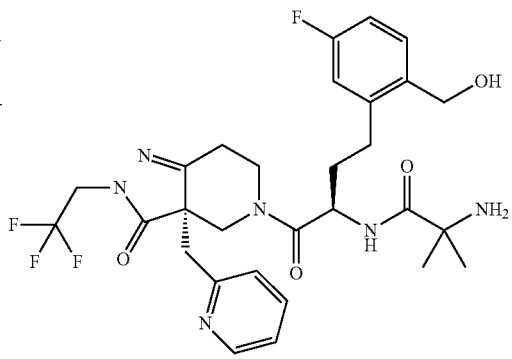 | 1.84 | 605.3 | (M − H)⁻ | A | QC2 |

Comparison Example 1

The comparison compound is synthesized according to the method disclosed in the example 180 in WO97/24369.

Half-Life in Human Liver Microsomes (HLM)

Test compounds (1 microM) are incubated with 1 mM $MgCl_2$ and 0.61 mg protein/mL HLM (XTreme 200) in 100 mM phosphate buffer (pH 7.4) at 37° C. on the 96-deep well plate. An aliquot of samples is collected at 0, 10, 30, and 60 mM time point, where 0 mM time point indicated the time when NADPH is added into the reaction mixture. Collected aliquots are extracted with acetonitrile solution containing an internal standard. The precipitated protein is spun down in centrifuge (2000 rpm, 15 mM). The compound concentration in supernatant is measured by LC/MS/MS system.

The half-life value is obtained by plotting the natural logarithm of the peak area ratio of compound/internal standard versus time. The slope of the line of the best fit through the points yields the elimination rate constant ($k_{el}$). This is converted to a half-life value using a following equation: Half-life=$ln2/k_{el}$.

In vitro Pharmacological Assays

Measurement of the ghrelin receptor agonistic activity induced $Ca^{2+}$ influx in HEK293 cells stably expressing human ghrelin receptor HEK293 cells stably expressing human ghrelin receptor are maintained in Dulbecco's modified Eagle medium (high glucose) supplemented with 10% fetal bovine serum, 100 units/mL penicillin, 100 microg/mL streptomycin and 500 microg/mL G418 at 37° C. in a humidified incubator with 5% $CO_2$ and grown to 60-80% confluence. The day before the assay, the cells are seeded on poly-D-lysine coated 384-well plates (BD FALCON) at a density of 10,000 cells per well and incubated overnight in incubator.

On the day of the assay, the cells are washed at three times with assay buffer (Hanks' balanced salt solution with 20 mM HEPES, pH7.4), and are incubated for 1 hour at room temperature to load 0.5 microM Fluo-4 AM reagent (Invitrogen).

After removing Fluo-4, and washing with assay buffer, the cells are added with various concentrations of the compounds. The changes in intracellular calcium concentration are monitored with the fluorescence imaging plate reader, FDSS6000 (Hamamatsu Photonics).

The $EC_{50}$ values for compounds of the present invention are determined from 11-point dose-response studies. Curves are generated using the average of duplicate wells for each data point. Finally, the $EC_{50}$ values are calculated using the best-fit dose curve determined by XLfit (ID Business Solutions Ltd).

All tested compounds show less than about 500 nanoM of $EC_{50}$ in the above assays. Preferable compounds show less than about 50 nanoM of $EC_{50}$ in the above assays.

More preferable compounds show less than about 20 nanoM of $EC_{50}$ in the above assays.

More preferable compounds in the above assays are: Examples 2, 3, 4, 5, 7, 8, 9, 10, 13, 14, and 17.

Table 6: Ratio of HLM CLint between compounds of the present invention and comparison compound 1.

TABLE 6

| Comparison | Structure | HLM CLint[1] (mL/min/kg) |
|---|---|---|
| 1 | 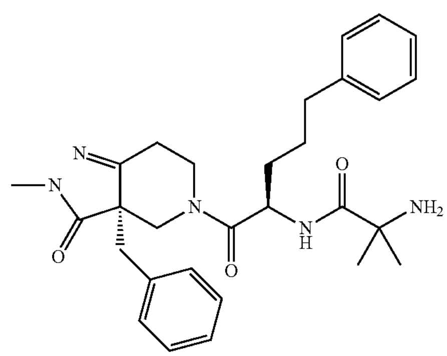 [SMILES: CNC(=O)[C@]1(Cc2ccccc2)CN(C(=O)[C@@H](CCCc2ccccc2)NC(=O)C(C)(C)N)CCC1=N] | 130.0 |

| Example | Structure | HLM CLint[1] (mL/min/kg) | ratio[2] |
|---|---|---|---|
| 2 | 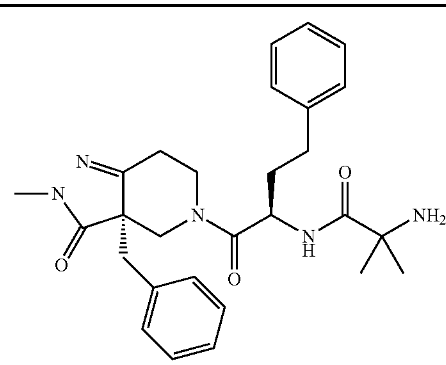 | 54.5 | 2.4 |

TABLE 6-continued
| | | | | |
|---|---|---|---|---|
| 3 | 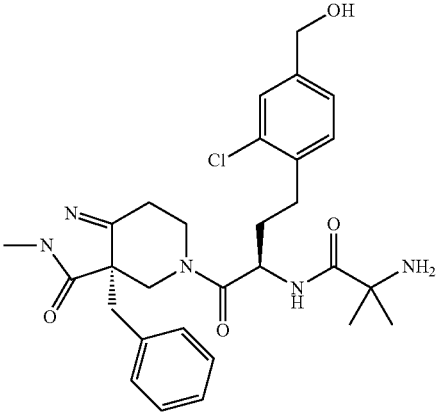 [SMILES: CNC(=O)[C@]1(Cc2ccccc2)CN(C(=O)[C@@H](CCc2ccc(CO)cc2Cl)NC(=O)C(C)(C)N)CCC1=N] | 43.5 | 3.0 | |
| 4 | 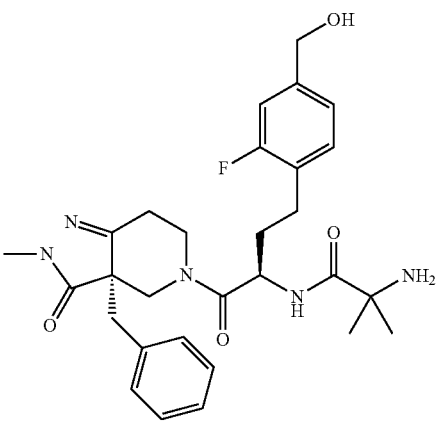 [SMILES: CNC(=O)[C@]1(Cc2ccccc2)CN(C(=O)[C@@H](CCc2ccc(CO)cc2F)NC(=O)C(C)(C)N)CCC1=N] | 21.7 | 6.0 | |
| 5 | 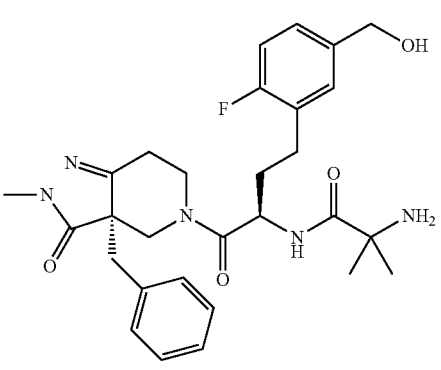 [SMILES: CNC(=O)[C@]1(Cc2ccccc2)CN(C(=O)[C@@H](CCc2cc(CO)ccc2F)NC(=O)C(C)(C)N)CCC1=N] | 44.6 | 2.9 | |
| 7 | 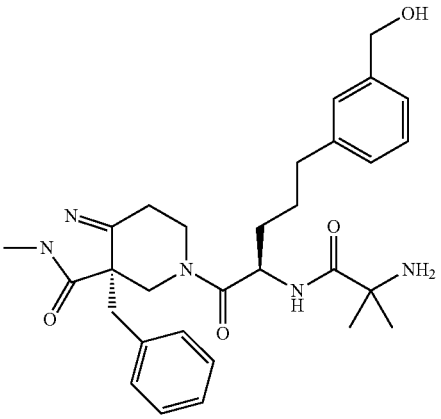 [SMILES: CNC(=O)[C@]1(Cc2ccccc2)CN(C(=O)[C@@H](CCCc2cccc(CO)c2)NC(=O)C(C)(C)N)CCC1=N] | 53.5 | 2.4 | |

TABLE 6-continued

| | | | |
|---|---|---|---|
| 8 | (structure) | 48.5 | 2.7 |
| 9 | (structure) | 19.7 | 6.6 |
| 10 | (structure) | 44.2 | 2.9 |
| 13 | (structure) | 36.0 | 3.6 |

TABLE 6-continued

| # | Structure | HLM CLint[1] | Ratio[2] |
|---|---|---|---|
| 14 | (structure) | 51.5 | 2.5 |
| 17 | (structure) | 56.7 | 2.3 |

[1] Clearance in human liver microsome
[2] Ratio of HLM CLint over comparison 1

In Vivo Pharmacological Assays

Growth Hormone (GH) Response in Conscious Mice

Female BALB/c mice (7 weeks old) are purchased from Charles River Japan and housed four or five animals per cage. After overnight fasting, test compounds are administered orally to the mice. Blood samples are collected at 5, 10, 30 min after drug administration. Two or three animals are used at each time point. Plasma concentration of mouse GH is measured using EIA kit (Rat Growth Hormone EIA KIT, SPI-Bio, France).

The compounds of the present invention show more than equal to 15 ng/mL of plasma concentration of mouse GH in the above assay.

In general, anesthetized rats have been used for investigating ghrelin compounds (Conventional method referred: Endocrinol Japon 31 (1984) 539-547, Journal of Endocrinology 171 (2001) 481-489, Gastroenterology 123 (2002) 1120-1128, Peptides 32 (2011)1001-1007). As the conventional assays require intravenous administration of the test compounds, they are not suitable for exploratory research of oral drugs. However the assay described above can be applied for oral administration in the fasted state, which is useful for evaluating growth hormone release of the test compounds in drug discovery. This is the first example of assay process for Growth hormone (GH) response in conscious fasting mice evaluating growth hormone release.

Effect on Cisplatin-Induced Cachexia/Anorexia in Rats

Male Wistar rats (7-8 weeks old) are purchased from Japan SLC, Inc., and housed individually in a room with controlled temperature and humidity under 12-h light and 12-h dark cycles (lights on at 08:00 o'clock). Rats are adapted to the experimental environment for at least 5 days and handled two times. Food and water are given ad libitum. Rats are divided into two groups, namely sham controls and cisplatin-treated groups. From day 0 to day 2, cisplatin (0.6 mg/kg/day, Wako Pure Chemical) is administered intraperitoneally at the end of light phase. Sham rats are given saline only. Test compounds are administered orally to the rats for 3 days (from day 0 to day 2) immediately before the administration of cisplatin to the rats. To prevent cisplatin-induced nephrotoxicity, 2-3 mL of saline is injected subcutaneously to the rats immediately after saline or cisplatin administration. Body weight and food consumption are assessed daily from day 0 to day 4.

The statistically significant decrease of the body weight and food consumption in the rat treated with cisplatin is observed. Oral administration of compounds significantly increased body weight and food intake in the cisplatin-treated rats.

There are some reports that ghrelin shows an effect on reducing food intake in the short period (Conventional method referred: Endocrinology 149 (2008) 455-460, Endocrinology 151 (2010) 3773-3782, Neurogastroenterol Motil 25 (2013) 373-382, e292, Peptides 46 (2013) 13-19, Vitamins and Hormones 92 (2013) 301-317). There is no report that ghrelin agonists show the suppression of sustainable weight loss, and suppression of reducing food intake as much as 5 days study. When the conventional assay methods are applied for as much as 5 days, they resulted in failure because of cisplatin-induced nephrotoxicity in rats. Grate efforts have made on working out the issue. Finally changing condition: 1) administration in the evening; 2) using well-handled rats adapted to the experimental environment for at least 5 days and handled at least twice; and 3) saline loading, surprisingly, leads to successful results, which is useful for evaluating cachexia/anorexia in drug discovery. This is the first example of assay process for cisplatin-induced cachexia/anorexia in rats.

Effect on Cachexia in Rats Bearing the AH-130 Cells

Male Wistar rats (4 weeks old) are purchased from Japan SLC, Inc., and housed individually in a room with controlled temperature and humidity under 12-h light and 12-h dark cycles (lights on at 08:00 o'clock). Rats are adapted to the experimental environment for at least 5 days and handled two times. Food and water are given ad libitum. Rats are divided into two groups, namely sham controls and tumor bearers. The latter is injected intraperitoneally with more than $1\times10^8$ AH-130 ascites hepatoma cells (Tohoku University, Sendai, Japan) on day 0. Sham rats are given PBS only. Tumor bearers group is further divided into treated and untreated, the former being administered test compounds orally for 7-9 days (from day 0 to days 6-8) at the end of light phase. Body weight is measured twice a week. At the end of the experiment, rats are sacrificed with $CO_2$ and greater pectoral muscle tissue is dissected and weighted.

Body weight is markedly reduced 4-5 days after inoculation of AH-130 ascites hepatoma cells compared with sham group. In rats administered compounds of the present invention, body weight and greater pectoral muscle weight at days 7-9 is significantly greater compared with control group.

There are no reports that ghrelin agonists suppress the sustainable weight loss. Grate efforts have made on working out the issue. Finally changing condition: 1) using immature rats instead of mature rats, 2) increase of the cell number (more than $1\times10^8$ AH-130 ascites hepatoma cells), and 3) administration in the evening, surprisingly, leads to successful results. The assay process above is useful for evaluating cachexia in drug discovery. This is the first successful example of assay process for cachexia (weight loss and muscle wasting) in rats bearing the AH-130 cells.

The invention claimed is:
1. A compound of the following formula (I):

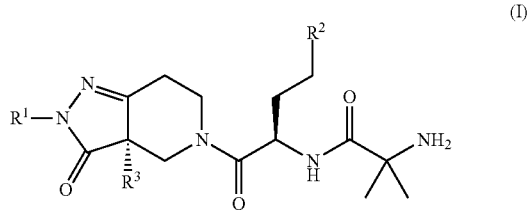

(I)

wherein:
$R^1$ is $C_{1-6}$ alkyl, where the alkyl is unsubstituted or substituted with one to three substituents independently selected from halogen;
$R^2$ is selected from the group consisting of (1) phenyl, (2) $CH_2$-phenyl($CH_2OH$), and (3) $CH_2$-pyridyl; where the benzene ring or the pyridine ring is unsubstituted or substituted with one to two substituents independently selected from the group consisting of (1) halogen, (2) $C_{1-6}$ alkyl, which may have substituents selected from the group consisting of halogen and hydroxyl, and (3) $C_{1-6}$ alkylsulfonyl;
$R^3$ is (1) benzyl, or (2) $CH_2$-(2-pyridyl); where the benzene ring or the pyridine ring is unsubstituted or substituted with one to two substituents independently selected from the group consisting of (1) halogen and (2) $C_{1-6}$ alkyl, which may have substituents selected from the group consisting of halogen, hydroxyl, and $C_{1-6}$ alkylsulfonyl;
or a pharmaceutically acceptable salt thereof.

2. The compound of formula (I) according to claim 1, wherein:
$R^1$ is methyl or trifluoroethyl;
or a pharmaceutically acceptable salt thereof.

3. The compound of formula (I) according to claim 1, wherein:
$R^1$ is methyl or trifluoroethyl;
$R^2$ is selected from the group consisting of (1) phenyl, (2) $CH_2$-phenyl($CH_2OH$), and (3) $CH_2$-pyridyl; where the benzene ring or the pyridine ring is unsubstituted or substituted with one to two substituents independently selected from the group consisting of (1) halogen, (2) methyl, (3) difluoromethyl, (4) trifluoromethyl, (5) hydroxymethyl, and (6) methanesulfonyl;
$R^3$ is (1) benzyl or (2) $CH_2$-(2-pyridyl), where the benzene ring or the pyridine ring is unsubstituted;
or a pharmaceutically acceptable salt thereof.

4. The compound of formula (I) according to claim 1, wherein:
$R^1$ is methyl or trifluoroethyl;
when $R^2$ is (1) phenyl, a compound where the benzene ring is unsubstituted or substituted with one to two substituents independently selected from the group consisting of halogen and hydroxymethyl; when $R^2$ is (2) $CH_2$-phenyl($CH_2OH$), a compound where the benzene ring is unsubstituted; when $R^2$ is (3) $CH_2$-pyridyl, a compound where the pyridine ring is unsubstituted or substituted with one to two substituents independently selected from the group consisting of difluoromethyl and trifluoromethyl;
$R^3$ is (1) benzyl or (2) $CH_2$-(2-pyridyl) where the benzene ring or the pyridine ring is unsubstituted;
or a pharmaceutically acceptable salt thereof.

5. The compound of formula (I) according to claim 1, wherein HLM Clint of the compound is lower than 65 mL/min/kg
or a pharmaceutically acceptable salt thereof.

6. The compound of formula (I) according to claim 1, which is selected from the group consisting of:
2-amino-N—((R)-1-((R)-3a-benzyl-2-methyl-3-oxo-3a, 4,6,7-tetrahydro-2H-pyrazolo[4,3-c]pyridin-5(3H)-yl)-4-(2-(methylsulfonyl)phenyl)-1-oxobutan-2-yl)-2-methylpropanamide;
2-amino-N—((R)-1-((R)-3a-benzyl-2-methyl-3-oxo-3a, 4,6,7-tetrahydro-2H-pyrazolo[4,3-c]pyridin-5(3H)-yl)-1-oxo-4-phenylbutan-2-yl)-2-methylpropanamide;
2-amino-N—((R)-1-((R)-3a-benzyl-2-methyl-3-oxo-3a, 4,6,7-tetrahydro-2H-pyrazolo[4,3-c]pyridin-5(3H)-yl)-4-(2-chloro-4-(hydroxymethyl)phenyl)-1-oxobutan-2-yl)-2-methylpropanamide;
2-amino-N—((R)-1-((R)-3a-benzyl-2-methyl-3-oxo-3a, 4,6,7-tetrahydro-2H-pyrazolo[4,3-c]pyridin-5(3H)-yl)-4-(2-fluoro-4-(hydroxymethyl)phenyl)-1-oxobutan-2-yl)-2-methylpropanamide;
2-amino-N—((R)-1-((R)-3a-benzyl-2-methyl-3-oxo-3a, 4,6,7-tetrahydro-2H-pyrazolo[4,3-c]pyridin-5(3H)-yl)-4-(2-fluoro-5-(hydroxymethyl)phenyl)-1-oxobutan-2-yl)-2-methylpropanamide;
2-amino-N—((R)-1-((R)-3a-benzyl-2-methyl-3-oxo-3a, 4,6,7-tetrahydro-2H-pyrazolo[4,3-c]pyridin-5(3H)-yl)-4-(2-(hydroxymethyl)phenyl)-1-oxobutan-2-yl)-2-methylpropanamide;

2-amino-N—((R)-1-((R)-3a-benzyl-2-methyl-3-oxo-3a,4,6,7-tetrahydro-2H-pyrazolo[4,3-c]pyridin-5(3H)-yl)-5-(3-(hydroxymethyl)phenyl)-1-oxopentan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-5-(2-(hydroxymethyl)phenyl)-1-oxopentan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-5-(pyridin-2-yl)pentan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-5-(6-(trifluoromethyl)pyridin-2-yl)pentan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-5-(5-fluoropyridin-2-yl)-1-oxopentan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-5-(6-methylpyridin-2-yl)-1-oxopentan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-5-(6-(difluoromethyl)pyridin-2-yl)-1-oxopentan-2-yl)-2-methylpropanamide;
2-amino-2-methyl-N—((R)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)-4-phenylbutan-2-yl)propanamide;
2-amino-2-methyl-N—((R)-4-(2-(methylsulfonyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)propanamide;
2-amino-N—((R)-4-(4-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide;
2-amino-N—((R)-4-(4-(fluoromethyl)-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide;
2-amino-N—((R)-4-(3-fluoro-4-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide; and
2-amino-N—((R)-4-(5-fluoro-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide;
or a pharmaceutically acceptable salt thereof.

7. The compound of formula (I) according to claim 1, which is selected from the group consisting of:
2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-4-phenylbutan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-4-(2-chloro-4-(hydroxymethyl)phenyl)-1-oxobutan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-4-(2-fluoro-4-(hydroxymethyl)phenyl)-1-oxobutan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-4-(2-fluoro-5-(hydroxymethyl)phenyl)-1-oxobutan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-5-(3-(hydroxymethyl)phenyl)-1-oxopentan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-5-(2-(hydroxymethyl)phenyl)-1-oxopentan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-5-(pyridin-2-yl)pentan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-1-oxo-5-(6-(trifluoromethyl)pyridin-2-yl)pentan-2-yl)-2-methylpropanamide;
2-amino-N—((R)-1-((R)-3a-benzyl-2-methyl-3-oxo-3a,4,6,7-tetrahydro-2H-pyrazolo[4,3-c]pyridin-5(3H)-yl)-5-(6-(difluoromethyl)pyridin-2-yl)-1-oxopentan-2-yl)-2-methylpropanamide;
2-amino-2-methyl-N—((R)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)-4-phenylbutan-2-yl)propanamide; and
2-amino-N—((R)-4-(4-(fluoromethyl)-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide;
or a pharmaceutically acceptable salt thereof.

8. A pharmaceutical composition comprising a compound of formula (I) or a pharmaceutically acceptable salt thereof, according to claim 1, and a pharmaceutically acceptable carrier.

9. The pharmaceutical composition according to claim 8, further comprising another pharmacologically active agent.

10. A method of treatment of an animal or human suffering from a condition or disorder mediated by the ghrelin receptor, which comprises administering to the animal or human an effective amount of a compound of formula (I) or a pharmaceutically acceptable salt according to claim 1,
wherein the condition or disorder is at least one selected from the group consisting of: cancer anorexia/cachexia; cachexia and anorexia by an anti-cancer drug; hyperalgesia by an anti-cancer drug; chronic obstructive pulmonary disease; chronic obstructive pulmonary disease cachexia; sarcopenia; an eating disorder; weight loss suppression; early postoperative recovery of a cancer patient; a chronic respiratory tract infection; inflammation; inflammatory bowel disease; functional dyspepsia; constipation; gastroparesis; heart failure; myocardial infarction; diabetic neuropathy; Parkinson's disease; multiple sclerosis; diagnosis and treatment of growth hormone deficiency; elderly quality of life improvement; a bowel movement disturbance of a spinal cord injury patient; postoperative ileus; and morphine induced ileus.

11. A process for preparing a pharmaceutical composition comprising mixing a compound of formula (I) according to claim 1 or a pharmaceutically acceptable salt thereof with a pharmaceutically acceptable carrier, diluent or excipient.

* * * * *

UNITED STATES PATENT AND TRADEMARK OFFICE
CERTIFICATE OF CORRECTION

PATENT NO. : 9,901,571 B2
APPLICATION NO. : 15/520491
DATED : February 27, 2018
INVENTOR(S) : Yasuhiro Iwata It is certified that error appears in the above-identified patent and that said Letters Patent is hereby corrected as shown below:

In the Specification

In Columns 23-26:

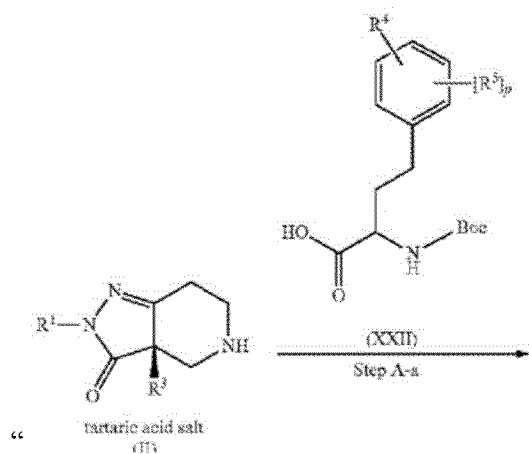

Signed and Sealed this
Fourth Day of December, 2018

Andrei Iancu
*Director of the United States Patent and Trademark Office*

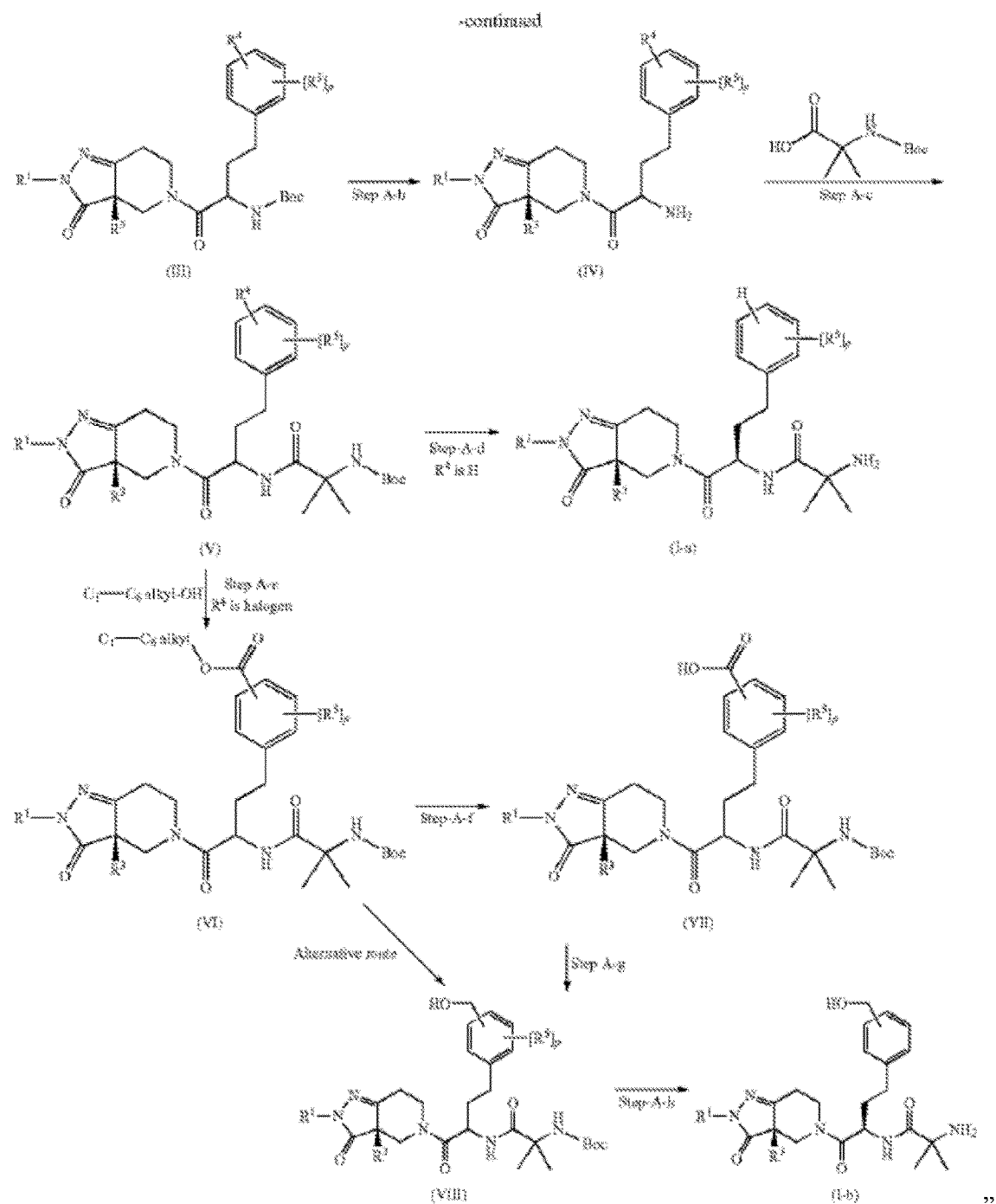

Should read:
[Chem.4]
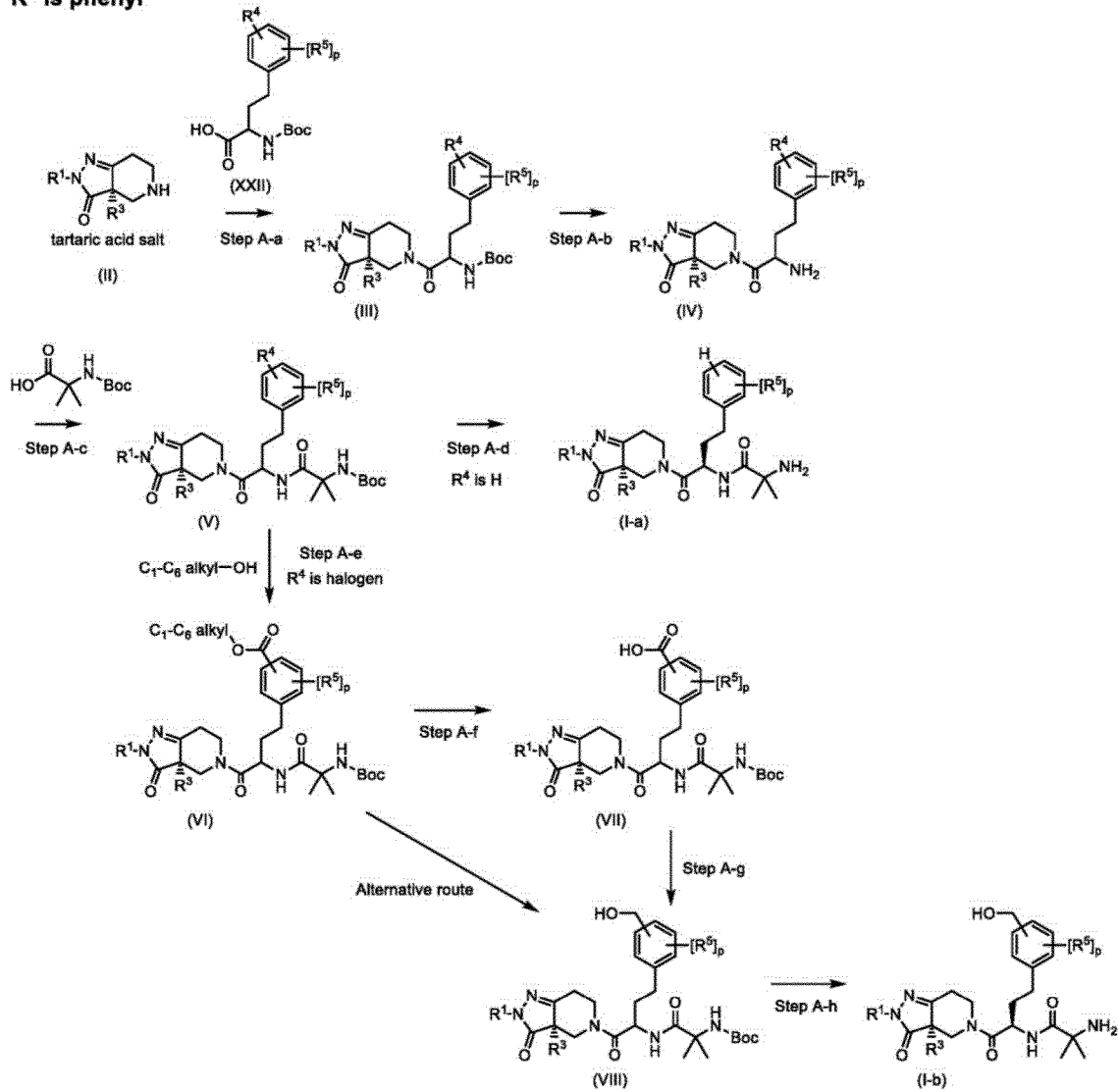
--                                                                                                              --.

CERTIFICATE OF CORRECTION (continued)
U.S. Pat. No. 9,901,571 B2

In Columns 27 to 30:

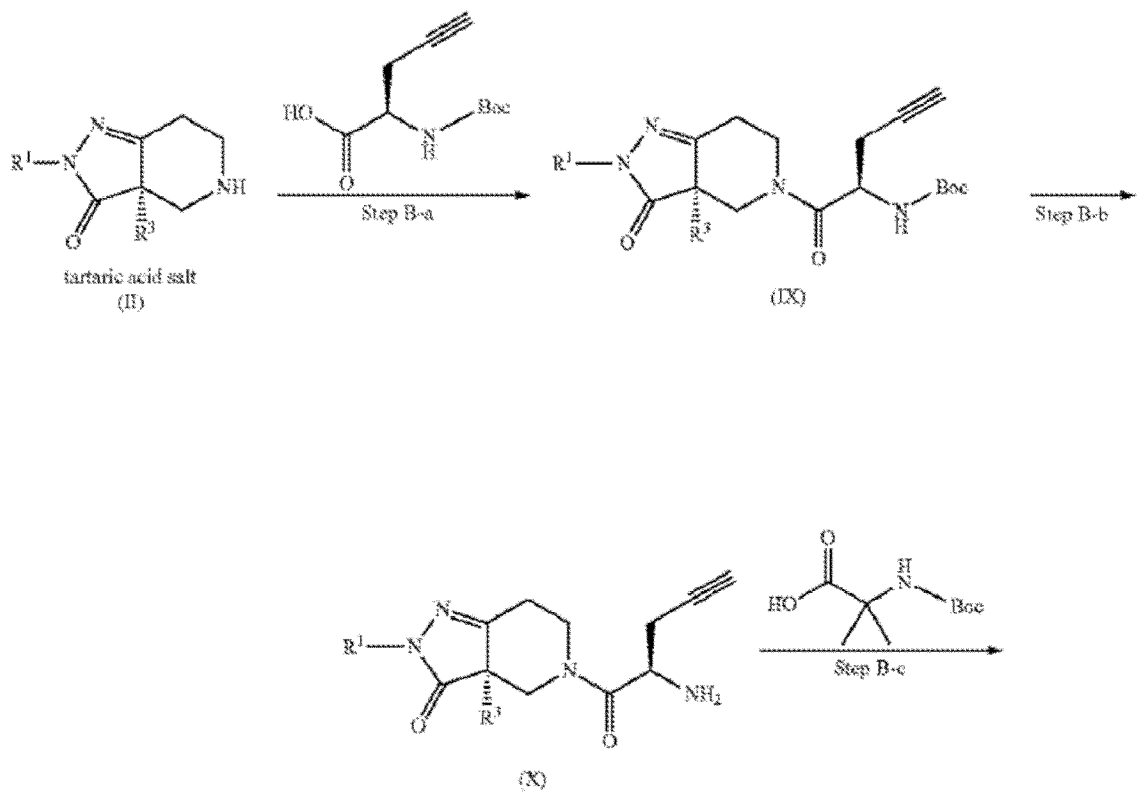

"

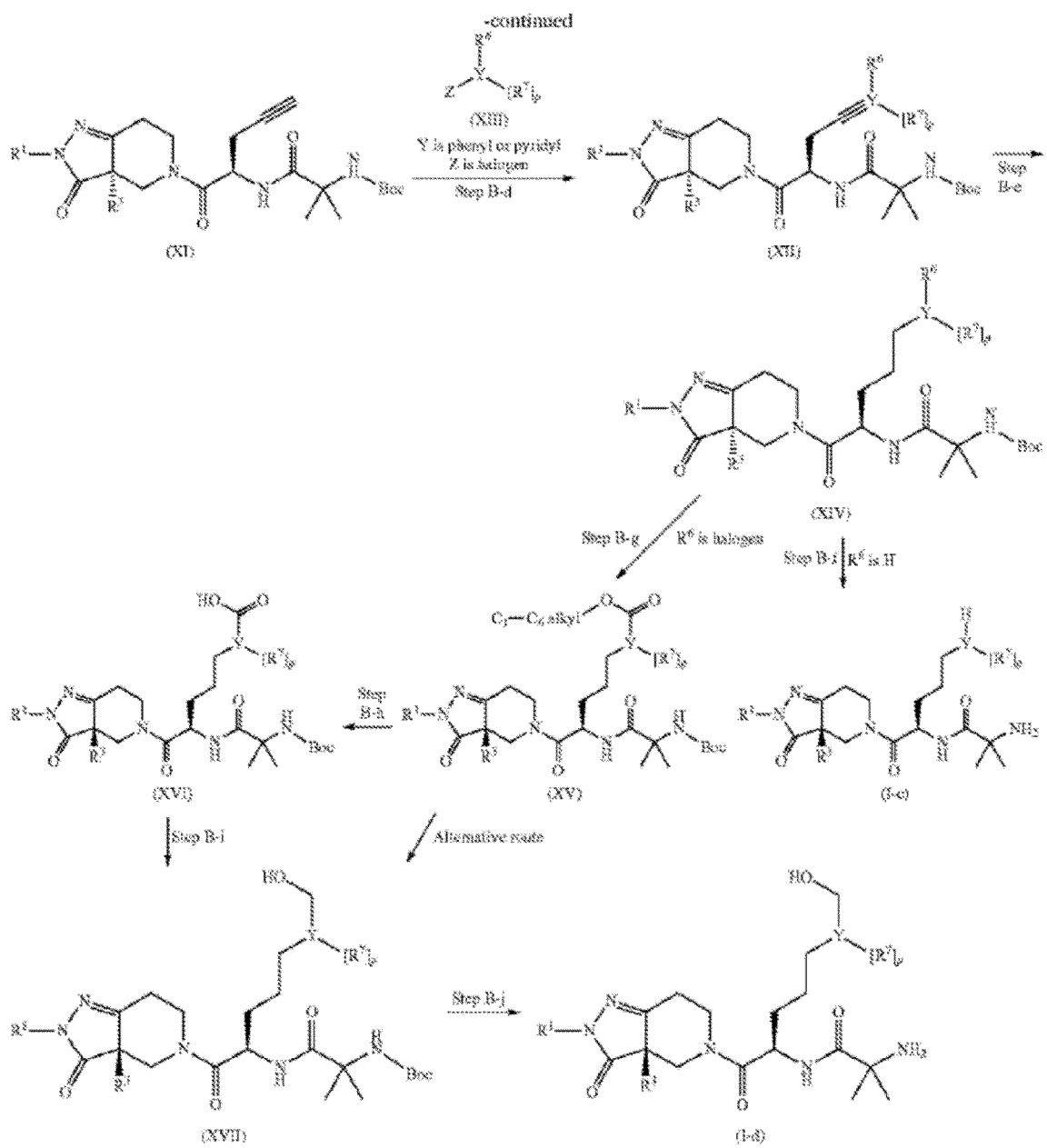

Should read:
[Chem. 5]
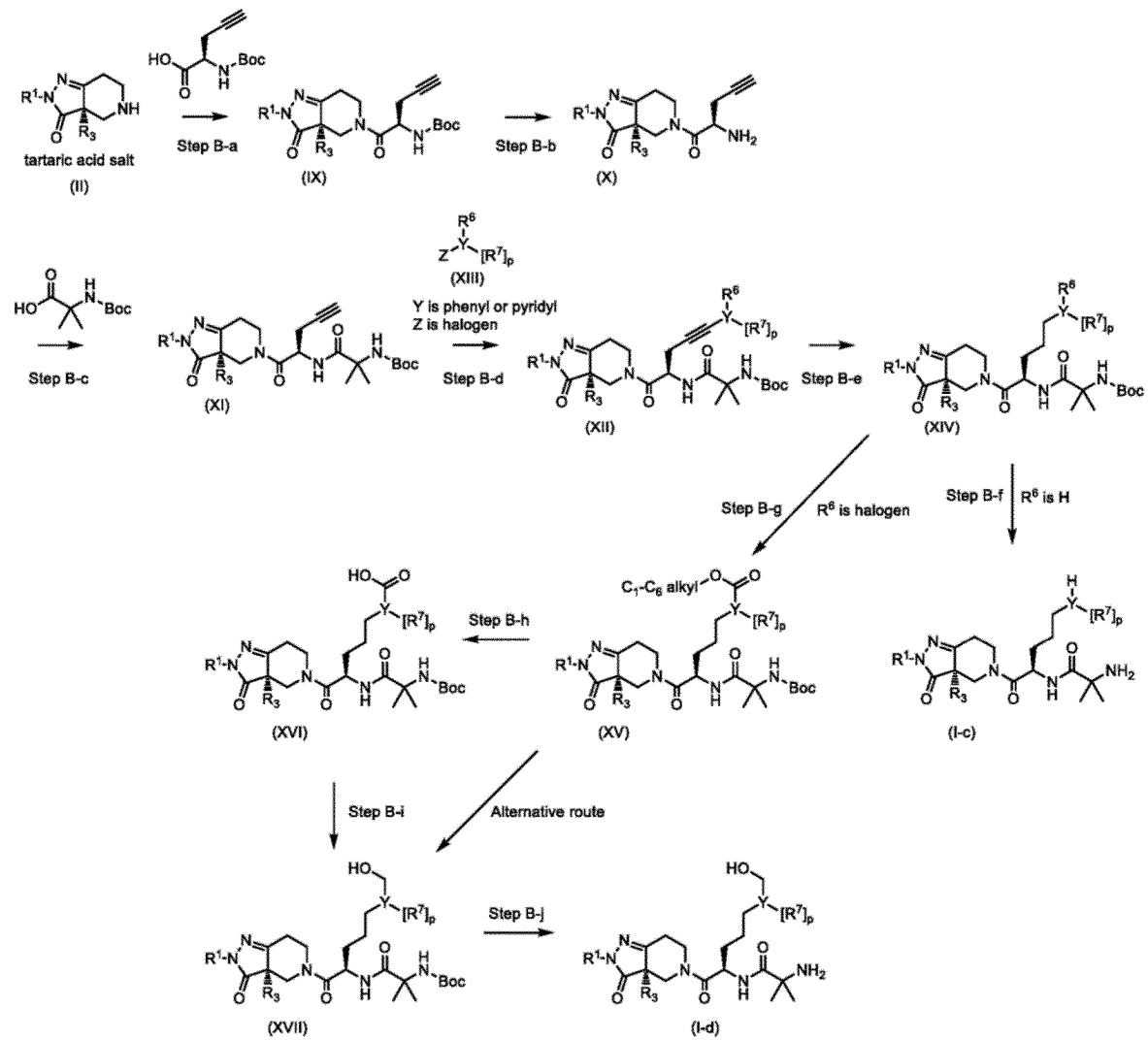

CERTIFICATE OF CORRECTION (continued)
U.S. Pat. No. 9,901,571 B2

In Column 33, Lines 40-62, Table 3:

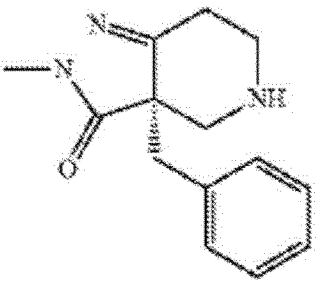

"

Should read:

TABLE 3

| Nucleus | Name | Structure |
|---|---|---|
| 1 | (R)-3a-benzyl-2-methyl-4,5,6,7-tetrahydro-2H-pyrazolo[4,3-c]pyridin-3(3aH)-one (2R,3R)-2,3-dihydroxysuccinate | 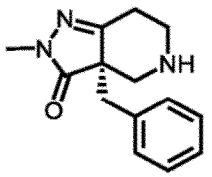<br>L-tartaric acid salt |
| 2 | (R)-3a-(pyridin-2-ylmethyl)-2-(2,2,2-trifluoroethyl)-4,5,6,7-tetrahydro-2H-pyrazolo[4,3-c]pyridin-3(3aH)-one (2S,3S)-2,3-dihydroxysuccinate | 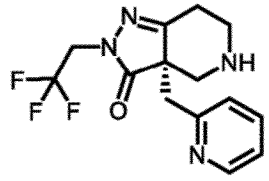<br>D-tartaric acid salt |

In Columns 67 to 72, Table 5-1:

| Example | Name | Structure | tR (min) | m/z | Ion mode | Condition | Method |
|---|---|---|---|---|---|---|---|
| 5 | 2-amino-N-((R)-1-((R)-3a-benzyl-3-methyl-3-oxo-3a,4,6,7-tetrahydro-2H-pyrazolo[4,3-c]pyridin-5(3H)-yl)-4-(2-fluoro-5-(hydroxymethyl)phenyl)-1-oxobutan-2-yl)-2-methylpropanamide | 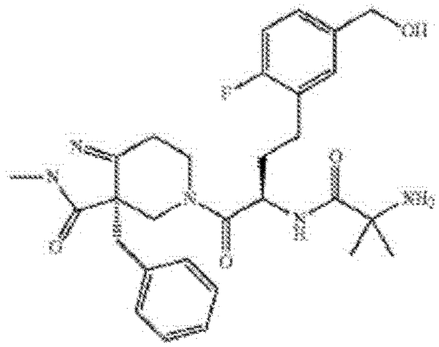 | 1.28 | 536.4 | (M + H)+ | A | QC1 |
| 6 | 2-amino-N-((R)-1-((R)-3a-benzyl-3-methyl-3-oxo-3a,4,6,7-tetrahydro-2H-pyrazolo[4,3-c]pyridin-5(3H)-yl)-4-(2-(hydroxymethyl)phenyl)-1-oxobutan-2-yl)-2-methylpropanamide | 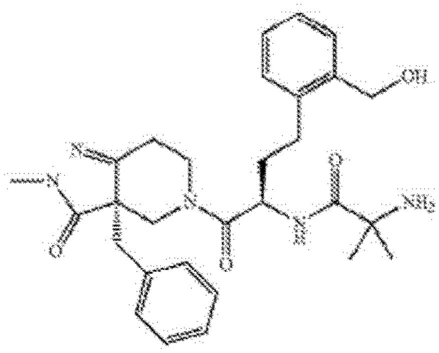 | 1.28 | 520.3 | (M + H)+ | B | QC2 |
| 7 | 2-amino-N-((R)-1-((R)-3a-benzyl-3-methyl-3-oxo-3a,4,6,7-tetrahydro-2H-pyrazolo[4,3-c]pyridin-5(3H)-yl)-5-(3-(hydroxymethyl)phenyl)-1-oxopentan-2-yl)-2-methylpropanamide | 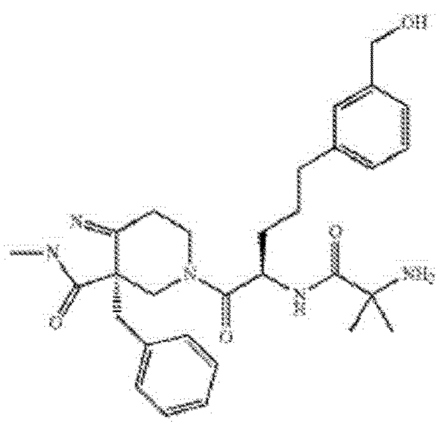 | 1.30 | 532.5 | (M + H)+ | A | QC2 |
| 8 | 2-amino-N-((R)-1-((R)-3a-benzyl-3-methyl-3-oxo-3a,4,6,7-tetrahydro-2H-pyrazolo[4,3-c]pyridin-5(3H)-yl)-5-(2-(hydroxymethyl)phenyl)-1-oxopentan-2-yl)-2-methylpropanamide | 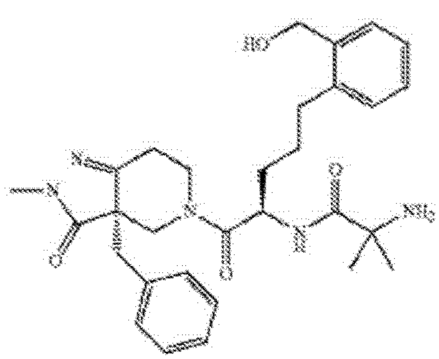 | 1.33 | 534.3 | (M + H)+ | A | QC2 |

CERTIFICATE OF CORRECTION (continued)
U.S. Pat. No. 9,901,571 B2

Should read:

TABLE 5-1

| Example | Name | Structure | tR (min) | m/z | Ion mode | Condition | Method |
|---|---|---|---|---|---|---|---|
| 1 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(2-(methylsulfonyl)phenyl)-1-oxobutan-2-yl)-2-methylpropanamide | 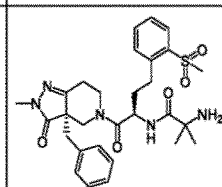 | 1.31 | 566.3 | (M-H)⁻ | B | QC1 |
| 2 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-4-phenylbutan-2-yl)-2-methylpropanamide | 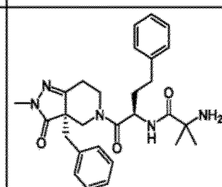 | 1.47 | 490.3 | (M-H)⁻ | A | QC1 |
| 3 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(2-chloro-4-(hydroxymethyl)phenyl)-1-oxobutan-2-yl)-2-methylpropanamide | 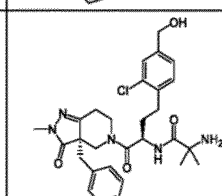 | 1.79 | 552.3 | (M-H)⁻ | A | QC2 |
| 4 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(2-fluoro-4-(hydroxymethyl)phenyl)-1-oxobutan-2-yl)-2-methylpropanamide | 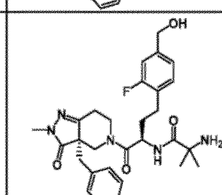 | 1.25 | 536.4 | (M-H)⁻ | A | QC1 |
| 5 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(2-fluoro-5-(hydroxymethyl)phenyl)-1-oxobutan-2-yl)-2-methylpropanamide | 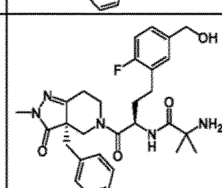 | 1.28 | 536.4 | (M-H)⁻ | A | QC1 |

| | | | | | | | |
|---|---|---|---|---|---|---|---|
| 6 | 2-amino-N-((R)-1-((R)-3a-benzyl-2-methyl-3-oxo-3a,4,6,7-tetrahydro-2H-pyrazolo[4,3-c]pyridin-5(3H)-yl)-4-(2-(hydroxymethyl)phenyl)-1-oxobutan-2-yl)-2-methylpropanamide | 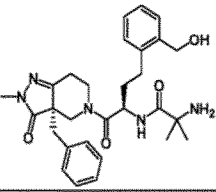 | 1.28 | 520.3 | (M+H)⁺ | B | QC2 |
| 7 | 2-amino-N-((R)-1-((R)-3a-benzyl-2-methyl-3-oxo-3a,4,6,7-tetrahydro-2H-pyrazolo[4,3-c]pyridin-5(3H)-yl)-5-(3-(hydroxymethyl)phenyl)-1-oxopentan-2-yl)-2-methylpropanamide | 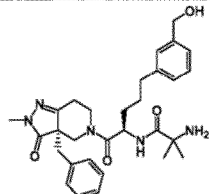 | 1.30 | 532.5 | (M-H)⁻ | A | QC2 |
| 8 | 2-amino-N-((R)-1-((R)-3a-benzyl-2-methyl-3-oxo-3a,4,6,7-tetrahydro-2H-pyrazolo[4,3-c]pyridin-5(3H)-yl)-5-(2-(hydroxymethyl)phenyl)-1-oxopentan-2-yl)-2-methylpropanamide | 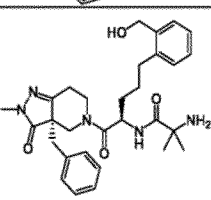 | 1.33 | 534.3 | (M+H)⁺ | A | QC2 |
| 9 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-5-(pyridin-2-yl)pentan-2-yl)-2-methylpropanamide | 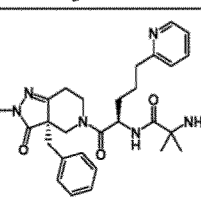 | 1.24 | 503.4 | (M-H)⁻ | A | QC2 |

CERTIFICATE OF CORRECTION (continued)
U.S. Pat. No. 9,901,571 B2

In Columns 71-76, Table 5-2:

| 10 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-5-(6-(trifluoromethyl)pyridin-2-yl)pentan-2-yl)-2-methylpropanamide | | CF₃ | 1.48 | 571.4 (M+H)⁺ | A | QC1 |

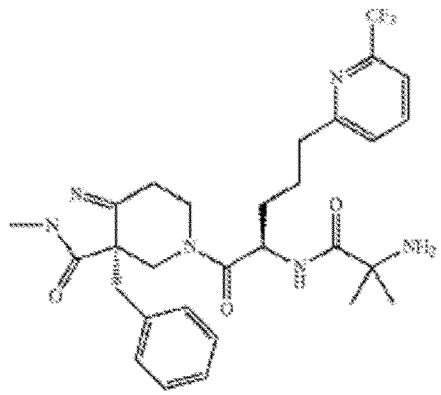 [SMILES: CNC(=O)[C@]1(Cc2ccccc2)CN(C(=O)[C@@H](CCCc2cccc(C(F)(F)F)n2)NC(=O)C(C)(C)N)CCC1=N]

| 11 | 2-amino-N-((R)-1-((R)-3a-benzyl-2-methyl-3-oxo-3a,4,6,7-tetrahydro-2H-pyrazolo[4,3-c]pyridin-5(3H)-yl)-5-(5-fluoropyridin-2-yl)-1-oxopentan-2-yl)-2-methylpropanamide | | F | 1.32 | 523.2 (M+H)⁺ | A | QC1 |

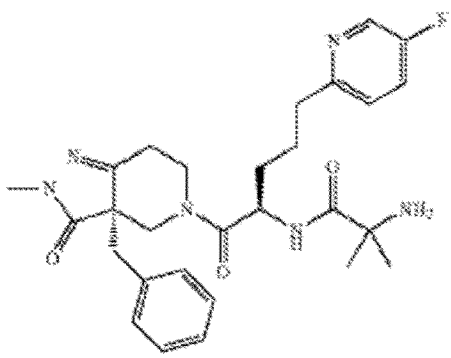

"

| | | | | | | |
|---|---|---|---|---|---|---|
| 12 | 2-amino-N-((R)-1-((R)-3a-benzyl-2-methyl-3-oxo-3a,4,6,7-tetrahydro-2H-pyrazolo[4,3-c]pyridin-5(3H)-yl)-8-(6-methylpyridin-2-yl)-1-oxooctan-2-yl)-2-methylpropanamide | | 1.31 | 589.3 (M + H)⁺ | A | QC1 |
| 13 | 2-amino-N-((R)-1-((R)-3a-benzyl-2-methyl-3-oxo-3a,4,6,7-tetrahydro-2H-pyrazolo[4,3-c]pyridin-5(3H)-yl)-5-(6-(difluoromethyl)pyridin-2-yl)-1-oxopentan-2-yl)-2-methylpropanamide | | 1.46 | 555.2 (M + H)⁺ | A | QC1 |
| 14 | 2-amino-2-methyl-N-((R)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)-4-phenylbutan-2-yl)propanamide | | 1.51 | 589.3 (M + H)⁺ | A | QC1 |
| 15 | 2-amino-2-methyl-N-((R)-4-(2-(methylsulfonyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)propanamide | | 1.35 | 635.2 (M + H)⁺ | B | QC1 |

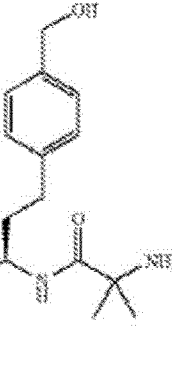

Should read:

TABLE 5-2

| | | | | | | | |
|---|---|---|---|---|---|---|---|
| 10 | 2-amino-N-((R)-1-((R)-3a-benzyl-2-methyl-3-oxo-3a,4,6,7-tetrahydro-2H-pyrazolo[4,3-c]pyridin-5(3H)-yl)-1-oxo-5-(6-(trifluoromethyl)pyridin-2-yl)pentan-2-yl)-2-methylpropanamide | | 1.48 | 571.4 | (M-H)⁻ | A | QC1 |
| 11 | 2-amino-N-((R)-1-((R)-3a-benzyl-2-methyl-3-oxo-3a,4,6,7-tetrahydro-2H-pyrazolo[4,3-c]pyridin-5(3H)-yl)-5-(5-fluoropyridin-2-yl)-1-oxopentan-2-yl)-2-methylpropanamide | | 1.32 | 523.2 | (M+H)⁺ | A | QC1 |
| 12 | 2-amino-N-((R)-1-((R)-3a-benzyl-2-methyl-3-oxo-3a,4,6,7-tetrahydro-2H-pyrazolo[4,3-c]pyridin-5(3H)-yl)-5-(6-methylpyridin-2-yl)-1-oxopentan-2-yl)-2-methylpropanamide | | 1.31 | 519.3 | (M+H)⁺ | A | QC1 |
| 13 | 2-amino-N-((R)-1-((R)-3a-benzyl-2-methyl-3-oxo-3a,4,6,7-tetrahydro-2H-pyrazolo[4,3-c]pyridin-5(3H)-yl)-5-(6-(difluoromethyl)pyridin-2-yl)-1-oxopentan-2-yl)-2-methylpropanamide | | 1.40 | 555.2 | (M+H)⁺ | A | QC1 |
| 14 | 2-amino-2-methyl-N-((R)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)-4-phenylbutan-2-yl)propanamide | | 1.51 | 559.3 | (M+H)⁺ | A | QC1 |
| 15 | 2-amino-2-methyl-N-((R)-4-(2-(methylsulfonyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)propanamide | | 1.35 | 635.2 | (M-H)⁻ | B | QC1 |
| 16 | 2-amino-N-((R)-4-(4-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide | | 1.26 | 587.4 | (M-H)⁻ | A | QC1 |

--

| | | | | | | | |
|---|---|---|---|---|---|---|---|
| 17 | 2-amino-N-((R)-4-(4-(fluoromethyl)-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide | | 1.37 | 605.3 | (M-H)⁻ | A | QC1 |
| 18 | 2-amino-N-((R)-4-(3-fluoro-4-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide | | 1.30 | 605.3 | (M-H)⁻ | A | QC1 |
| 19 | 2-amino-N-((R)-4-(5-fluoro-2-(hydroxymethyl)phenyl)-1-oxo-1-((R)-3-oxo-3a-(pyridin-2-ylmethyl)-2-(2,2,2-trifluoroethyl)-3a,4,6,7-tetrahydro-2H-pyrazolo[4,3-c]pyridin-5(3H)-yl)butan-2-yl)-2-methylpropanamide | | 1.84 | 605.3 | (M-H)⁻ | A | QC2 |

--.

In Columns 77 to 83, Table 6:

TABLE 6

| Comparison | Structure | BLM CLint[b] (mL/min/kg) |
|---|---|---|
| 1 | | 131.0 |

| Example | Structure | BLM CLint[b] (mL/min/kg) | ratio[c] |
|---|---|---|---|
| 2 | 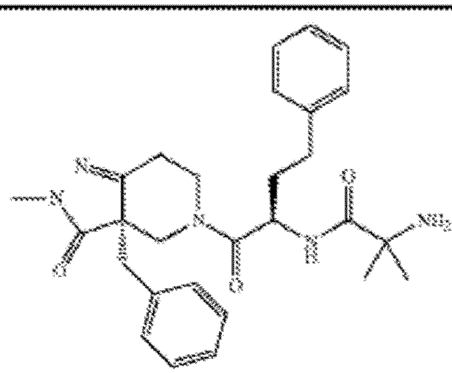 | 54.5 | 2.4 |

``

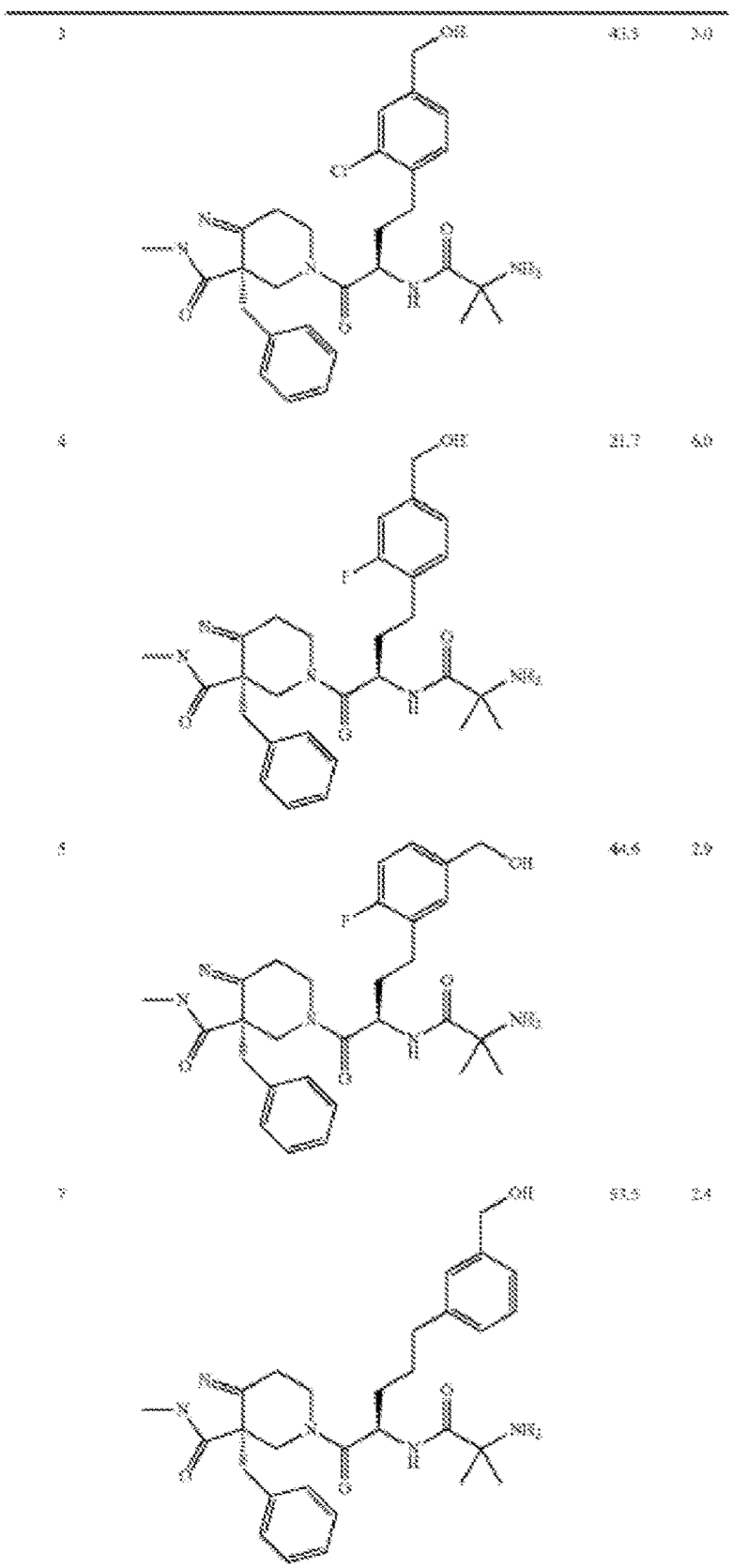

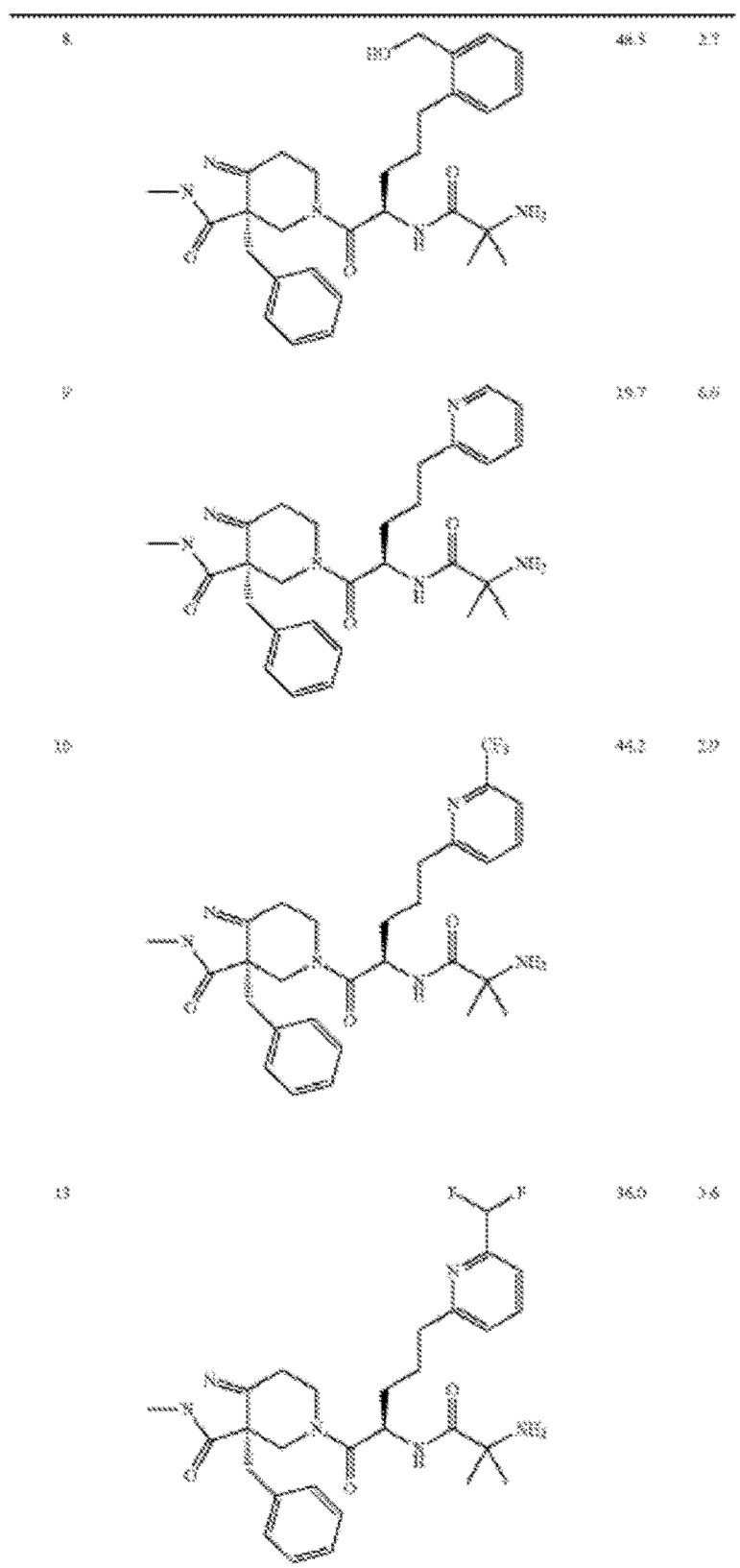

CERTIFICATE OF CORRECTION (continued)
U.S. Pat. No. 9,901,571 B2

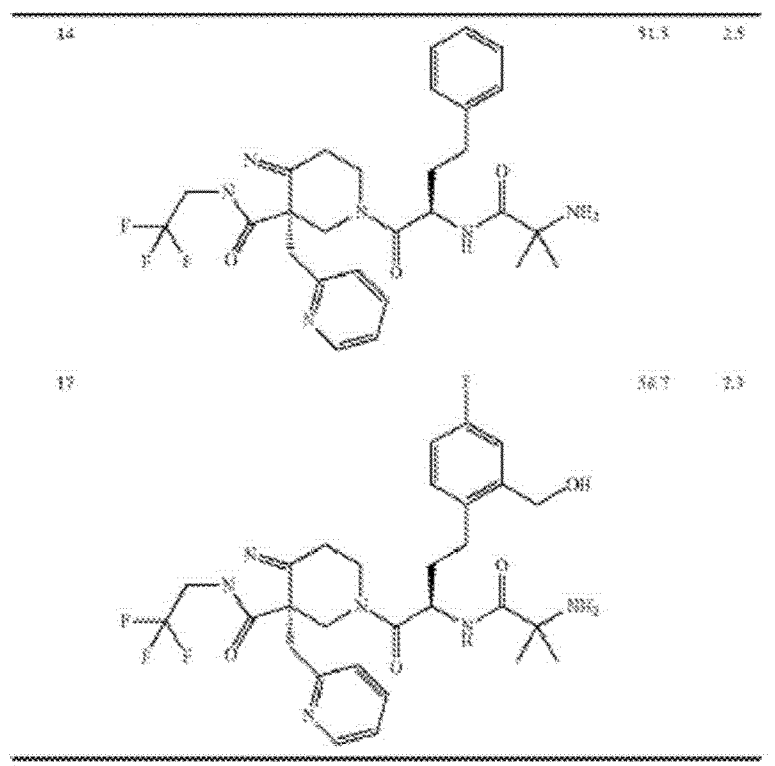

Should read:

TABLE 6

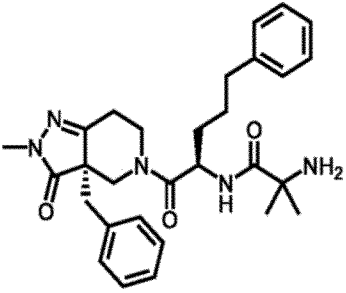

| Comparison | Structure | HLM CLint[1] (mL/min/kg) |
|---|---|---|
| 1 | 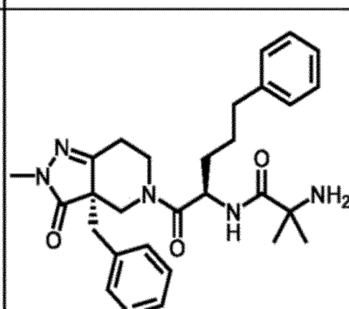 | 130.0 |
| -- | | |

| Example | Structure | HLM CLint[1] (mL/min/kg) | ratio[2] |
|---|---|---|---|
| 2 | 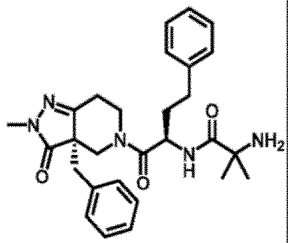 | 54.5 | 2.4 |
| 3 | 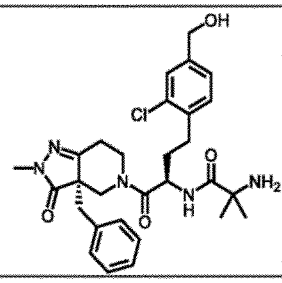 | 43.5 | 3.0 |
| 4 | 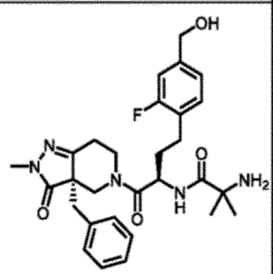 | 21.7 | 6.0 |
| 5 | 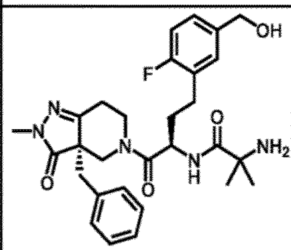 | 44.6 | 2.9 |
| 7 | 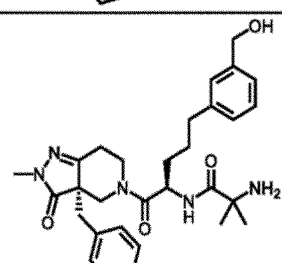 | 53.5 | 2.4 |
| 8 | 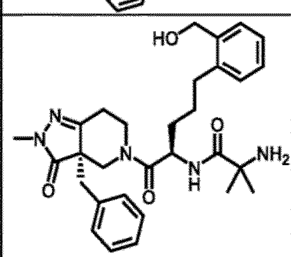 | 48.5 | 2.7 |

| Example | Structure | HLM CLint[1] (mL/min/kg) | ratio[2] |
|---|---|---|---|
| 9 | 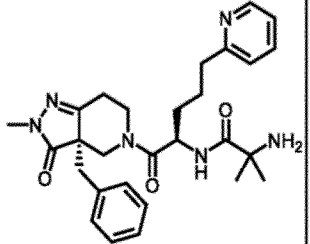 | 19.7 | 6.6 |
| 10 | 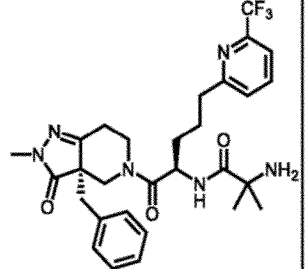 | 44.2 | 2.9 |
| 13 | 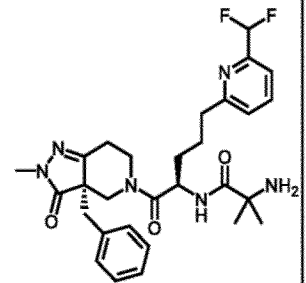 | 36.0 | 3.6 |
| 14 | 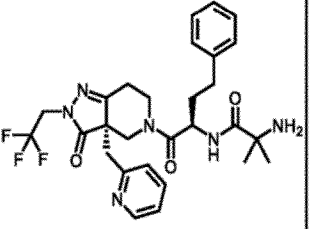 | 51.5 | 2.5 |
| 17 | 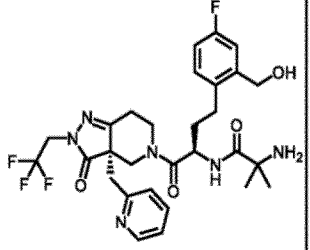 | 56.7 | 2.3 |
1) Clearance in human liver microsome
2) Ratio of HLM CLint over comparision 1